(12) United States Patent
Glenn et al.

(10) Patent No.: US 10,940,281 B2
(45) Date of Patent: Mar. 9, 2021

(54) VENTILATION TRIGGERING

(71) Applicant: Covidien LP, Masnfield, MA (US)

(72) Inventors: Gregory J. Glenn, Irving, CA (US);
Matthew Tyson Grant, San Marcos, CA (US)

(73) Assignee: COVIDIEN LP, Mansfield, MA (US)

( * ) Notice: Subject to any disclaimer, the term of this patent is extended or adjusted under 35 U.S.C. 154(b) by 414 days.

(21) Appl. No.: 15/914,372

(22) Filed: Mar. 7, 2018

(65) Prior Publication Data
US 2018/0193578 A1    Jul. 12, 2018

Related U.S. Application Data

(62) Division of application No. 14/524,881, filed on Oct. 27, 2014, now Pat. No. 9,950,129.

(51) Int. Cl.
*A61M 16/00* (2006.01)
*G16H 40/63* (2018.01)
(Continued)

(52) U.S. Cl.
CPC ......... *A61M 16/0069* (2014.02); *A61B 5/087* (2013.01); *A61M 16/0003* (2014.02); *A61M 16/026* (2017.08); *A61M 16/04* (2013.01); *A61M 16/06* (2013.01); *A61M 16/20* (2013.01); *G06F 19/00* (2013.01); *G16H 40/63* (2018.01); *A61M 2016/0015* (2013.01); *A61M 2016/0027* (2013.01); *A61M 2205/3331* (2013.01); *A61M 2205/52* (2013.01); *A61M 2230/005* (2013.01);
(Continued)

(58) Field of Classification Search
CPC ........ G16H 40/60; G16H 40/63; G16H 20/40; G16Z 99/00; G06F 19/00; G06F 19/3481; A61M 16/0003; A61M 16/0069; A61M 16/024; A61M 16/026; A61M 2016/0015; A61M 2016/0018; A61M 2016/0027; A61M 2016/003; A61M 2230/005; A61M 2205/52; G06Q 50/22–24
See application file for complete search history.

(56) References Cited

U.S. PATENT DOCUMENTS 1,202,125 A    10/1916    Tullar
1,202,126 A    10/1916    Tullar
(Continued)

FOREIGN PATENT DOCUMENTS

EP    0414777    3/1991
EP    521515     1/1993
(Continued)

OTHER PUBLICATIONS

US 7,284,551 B2, 10/2007, Jones et al. (withdrawn)
7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1998, pp. 1-32.
(Continued)

*Primary Examiner* — Kathryn E Ditmer

(57) ABSTRACT

The systems and methods provide for novel a triggering mode that allows the patient to trigger or initiate the delivery of a breath during ventilation on a ventilator. Further, the systems and methods provide for triggering ventilation utilizing a statistical trigger mode. Additionally, the systems and methods provide for analyzing and/or displaying information related to a potential change in a triggering threshold for a currently utilized breath type.

18 Claims, 15 Drawing Sheets

(51) Int. Cl.
  *A61B 5/087* (2006.01)
  *G06F 19/00* (2018.01)
  *G16H 20/40* (2018.01)
  *G16H 50/30* (2018.01)
  *A61M 16/04* (2006.01)
  *A61M 16/06* (2006.01)
  *A61M 16/20* (2006.01)

(52) U.S. Cl.
  CPC ......... *G06F 19/3481* (2013.01); *G16H 20/40* (2018.01); *G16H 50/30* (2018.01)

(56) References Cited

U.S. PATENT DOCUMENTS

| | | |
|---|---|---|
| 1,241,056 A | 9/1917 | Tullar |
| 2,914,067 A | 11/1959 | Meidenbauer |
| 3,339,545 A | 9/1967 | Barnett |
| 3,575,167 A | 4/1971 | Michielsen |
| 3,577,984 A | 5/1971 | Levy et al. |
| 3,584,618 A | 6/1971 | Reinhard et al. |
| 3,584,621 A | 6/1971 | Bird et al. |
| 3,586,021 A | 6/1971 | McGuinness |
| 3,628,531 A | 12/1971 | Harris |
| 3,633,576 A | 1/1972 | Gorsuch |
| 3,643,652 A | 2/1972 | Beltran |
| 3,659,590 A | 5/1972 | Jones et al. |
| 3,662,751 A | 5/1972 | Barkalow et al. |
| 3,664,370 A | 5/1972 | Warnow |
| 3,669,108 A | 6/1972 | Sundblom et al. |
| 3,677,267 A | 7/1972 | Richards |
| 3,695,263 A | 10/1972 | Kipling |
| 3,722,510 A | 3/1973 | Parker |
| 3,739,776 A | 6/1973 | Bird et al. |
| 3,741,208 A | 6/1973 | Jonsson et al. |
| 3,753,436 A | 8/1973 | Bird et al. |
| 3,756,229 A | 9/1973 | Ollivier |
| 3,759,249 A | 9/1973 | Fletcher et al. |
| 3,768,468 A | 10/1973 | Cox |
| 3,789,837 A | 2/1974 | Philips et al. |
| 3,834,382 A | 9/1974 | Lederman et al. |
| 3,871,371 A | 3/1975 | Weigl |
| 3,889,669 A | 6/1975 | Weigl |
| 3,896,800 A | 7/1975 | Cibulka |
| 3,903,881 A | 9/1975 | Weigl |
| 3,905,362 A | 9/1975 | Eyrick et al. |
| 3,908,704 A | 9/1975 | Clement et al. |
| 3,910,261 A | 10/1975 | Ragsdale et al. |
| 3,911,899 A | 10/1975 | Hattes |
| 3,940,742 A | 2/1976 | Hudspeth et al. |
| 3,952,739 A | 4/1976 | Cibulka |
| 3,957,044 A | 5/1976 | Fletcher et al. |
| 3,961,624 A | 6/1976 | Weigl |
| 3,961,627 A | 6/1976 | Ernst et al. |
| 3,968,794 A | 7/1976 | O'Neill |
| 3,968,795 A | 7/1976 | O'Neill et al. |
| 3,976,052 A | 8/1976 | Junginger et al. |
| 3,977,394 A | 8/1976 | Jones et al. |
| 3,981,301 A | 9/1976 | Warnow et al. |
| 3,985,131 A | 10/1976 | Buck et al. |
| 3,991,304 A | 11/1976 | Hillsman |
| 3,996,928 A | 12/1976 | Marx |
| 4,003,377 A | 1/1977 | Dahl |
| 4,029,120 A | 6/1977 | Christianson |
| 4,034,743 A | 7/1977 | Greenwood et al. |
| 4,036,217 A | 7/1977 | Ito et al. |
| 4,044,763 A | 8/1977 | Bird |
| 4,050,458 A | 9/1977 | Friend |
| 4,053,951 A | 10/1977 | Hudspeth et al. |
| 4,060,078 A | 11/1977 | Bird |
| 4,090,513 A | 5/1978 | Togawa |
| 4,095,592 A | 6/1978 | Delphia |
| 4,112,931 A | 9/1978 | Burns |
| 4,121,578 A | 10/1978 | Torzala |
| 4,155,357 A | 5/1979 | Dahl |
| 4,164,219 A | 8/1979 | Bird |
| 4,187,842 A | 2/1980 | Schreiber |
| 4,197,856 A | 4/1980 | Northrop |
| 4,211,221 A | 7/1980 | Schwanbom et al. |
| 4,215,409 A | 7/1980 | Strowe |
| 4,241,739 A | 12/1980 | Elson |
| 4,258,718 A | 3/1981 | Goldman |
| 4,275,722 A | 6/1981 | Sorensen |
| 4,281,651 A | 8/1981 | Cox |
| 4,284,075 A | 8/1981 | Krasberg |
| 4,294,242 A | 10/1981 | Cowans |
| 4,296,756 A | 10/1981 | Dunning et al. |
| 4,299,236 A | 11/1981 | Poirier |
| 4,308,872 A | 1/1982 | Watson et al. |
| 4,316,182 A | 2/1982 | Hodgson |
| 4,323,064 A | 4/1982 | Hoenig et al. |
| 4,326,513 A | 4/1982 | Schulz et al. |
| 4,340,044 A | 7/1982 | Levy et al. |
| 4,351,344 A | 9/1982 | Stenzler |
| 4,366,821 A | 1/1983 | Wittmaier et al. |
| 4,391,283 A | 7/1983 | Sharpless et al. |
| 4,401,115 A | 8/1983 | Monnier |
| 4,401,116 A | 8/1983 | Fry et al. |
| 4,407,295 A | 10/1983 | Steuer et al. |
| 4,421,113 A | 12/1983 | Gedeon et al. |
| 4,433,693 A | 2/1984 | Hochstein |
| 4,440,166 A | 4/1984 | Winkler et al. |
| 4,440,177 A | 4/1984 | Anderson et al. |
| 4,442,835 A | 4/1984 | Carnegie |
| 4,444,201 A | 4/1984 | Itoh |
| 4,459,982 A | 7/1984 | Fry |
| 4,459,983 A | 7/1984 | Beyreuther et al. |
| 4,463,764 A | 8/1984 | Anderson et al. |
| 4,473,081 A | 9/1984 | Dioguardi et al. |
| 4,495,944 A | 1/1985 | Brisson et al. |
| 4,498,471 A | 2/1985 | Kranz et al. |
| 4,503,850 A | 3/1985 | Pasternak |
| 4,506,667 A | 3/1985 | Ansite |
| 4,522,639 A | 6/1985 | Ansite et al. |
| 4,537,190 A | 8/1985 | Caillot et al. |
| 4,539,984 A | 9/1985 | Kiszel et al. |
| 4,550,726 A | 11/1985 | McEwen |
| 4,554,916 A | 11/1985 | Watt |
| 4,558,710 A | 12/1985 | Eichler |
| 4,566,450 A | 1/1986 | Brossman, Jr. |
| 4,579,115 A | 4/1986 | Wallroth et al. |
| 4,598,706 A | 7/1986 | Darowski et al. |
| 4,606,340 A | 8/1986 | Ansite |
| 4,612,928 A | 9/1986 | Tiep et al. |
| 4,630,605 A | 12/1986 | Pasternack |
| 4,637,385 A | 1/1987 | Rusz |
| 4,640,277 A | 2/1987 | Meyer et al. |
| 4,648,407 A | 3/1987 | Sackner |
| 4,653,493 A | 3/1987 | Hoppough |
| 4,654,029 A | 3/1987 | D'Antonio |
| 4,702,240 A | 10/1987 | Chaoui |
| 4,721,060 A | 1/1988 | Cannon et al. |
| 4,736,750 A | 4/1988 | Valdespino et al. |
| 4,752,089 A | 6/1988 | Carter |
| 4,757,824 A | 7/1988 | Chaumet |
| 4,766,894 A | 8/1988 | Legrand et al. |
| 4,790,327 A | 12/1988 | Despotis |
| 4,790,832 A | 12/1988 | Lopez |
| 4,796,618 A | 1/1989 | Garraffa |
| 4,796,639 A | 1/1989 | Snow et al. |
| 4,813,409 A | 3/1989 | Ismach |
| 4,852,582 A | 8/1989 | Pell |
| 4,867,152 A | 9/1989 | Kou et al. |
| 4,870,960 A | 10/1989 | Hradek |
| 4,870,961 A | 10/1989 | Barnard |
| 4,876,903 A | 10/1989 | Budinger |
| 4,889,116 A | 12/1989 | Taube |
| 4,917,108 A | 4/1990 | Mault |
| 4,921,642 A | 5/1990 | LaTorraca |
| 4,954,799 A | 9/1990 | Kumar |
| 4,981,295 A | 1/1991 | Belman et al. |
| 4,982,735 A | 1/1991 | Yagata et al. |
| 4,984,158 A | 1/1991 | Hillsman |
| 4,990,894 A | 2/1991 | Loescher et al. |
| 5,003,985 A | 4/1991 | White et al. |

(56) References Cited

U.S. PATENT DOCUMENTS

| | | |
|---|---|---|
| 5,004,472 A | 4/1991 | Wallace |
| 5,007,420 A | 4/1991 | Bird |
| 5,009,662 A | 4/1991 | Wallace et al. |
| 5,016,626 A | 5/1991 | Jones |
| 5,020,527 A | 6/1991 | Dessertine |
| 5,021,046 A | 6/1991 | Wallace |
| 5,022,393 A | 6/1991 | McGrady et al. |
| 5,048,515 A | 9/1991 | Sanso |
| 5,057,822 A | 10/1991 | Hoffman |
| 5,058,601 A | 10/1991 | Riker |
| 5,072,737 A | 12/1991 | Goulding |
| 5,074,297 A | 12/1991 | Venegas |
| 5,080,093 A | 1/1992 | Raabe et al. |
| 5,086,767 A | 2/1992 | Legal |
| 5,099,837 A | 3/1992 | Russel, Sr. et al. |
| 5,107,831 A | 4/1992 | Halpern et al. |
| 5,117,818 A | 6/1992 | Palfy |
| 5,127,398 A | 7/1992 | Stone |
| 5,129,390 A | 7/1992 | Chopin et al. |
| 5,134,994 A | 8/1992 | Say |
| 5,137,026 A | 8/1992 | Waterson et al. |
| 5,148,802 A | 9/1992 | Sanders et al. |
| 5,150,291 A | 9/1992 | Cummings et al. |
| 5,154,167 A | 10/1992 | Hepburn |
| 5,156,145 A | 10/1992 | Flood et al. |
| 5,161,525 A | 11/1992 | Kimm et al. |
| 5,163,423 A | 11/1992 | Suzuki |
| 5,165,397 A | 11/1992 | Arp |
| 5,165,398 A | 11/1992 | Bird |
| 5,167,506 A | 12/1992 | Kilis et al. |
| 5,174,284 A | 12/1992 | Jackson |
| 5,195,512 A | 3/1993 | Rosso |
| 5,203,343 A | 4/1993 | Axe et al. |
| 5,211,170 A | 5/1993 | Press |
| 5,224,487 A | 7/1993 | Bellofatto et al. |
| 5,231,981 A | 8/1993 | Schreiber et al. |
| 5,235,973 A | 8/1993 | Levinson |
| 5,237,987 A | 8/1993 | Anderson et al. |
| 5,239,995 A | 8/1993 | Estes et al. |
| 5,246,010 A | 9/1993 | Gazzara et al. |
| 5,251,632 A | 10/1993 | Delpy |
| 5,259,374 A | 11/1993 | Miller et al. |
| 5,261,397 A | 11/1993 | Grunstein |
| 5,261,415 A | 11/1993 | Dussault |
| 5,271,389 A | 12/1993 | Isaza et al. |
| 5,273,031 A | 12/1993 | Olsson et al. |
| 5,273,032 A | 12/1993 | Borody |
| 5,277,195 A | 1/1994 | Williams |
| 5,279,304 A | 1/1994 | Einhorn et al. |
| 5,279,549 A | 1/1994 | Ranford |
| 5,293,875 A | 3/1994 | Stone |
| 5,299,568 A | 4/1994 | Forare et al. |
| 5,301,921 A | 4/1994 | Kumar |
| 5,303,698 A | 4/1994 | Tobia et al. |
| 5,303,699 A | 4/1994 | Bonassa et al. |
| 5,303,700 A | 4/1994 | Weismann et al. |
| 5,307,794 A | 5/1994 | Rauterkus et al. |
| 5,307,795 A | 5/1994 | Whitwam et al. |
| 5,316,009 A | 5/1994 | Yamada |
| 5,318,017 A | 6/1994 | Ellison |
| 5,318,487 A | 6/1994 | Golen et al. |
| 5,319,355 A | 6/1994 | Russek |
| 5,319,540 A | 6/1994 | Isaza et al. |
| 5,320,093 A | 6/1994 | Raemer |
| 5,322,057 A | 6/1994 | Raabe et al. |
| 5,322,059 A | 6/1994 | Walther |
| 5,323,772 A | 6/1994 | Linden et al. |
| 5,325,861 A | 7/1994 | Goulding |
| 5,333,106 A | 7/1994 | Lanpher et al. |
| 5,333,606 A | 8/1994 | Schneider et al. |
| 5,335,650 A | 8/1994 | Shaffer et al. |
| 5,335,654 A | 8/1994 | Rapoport |
| 5,339,807 A | 8/1994 | Carter |
| 5,339,825 A | 8/1994 | McNaughton et al. |
| 5,343,857 A | 9/1994 | Schneider et al. |
| 5,351,522 A | 10/1994 | Lura |
| 5,355,893 A | 10/1994 | Mick et al. |
| 5,357,946 A | 10/1994 | Kee et al. |
| 5,357,975 A | 10/1994 | Kraemer et al. |
| 5,363,842 A | 11/1994 | Mishelevich et al. |
| 5,365,922 A | 11/1994 | Raemer |
| 5,368,019 A | 11/1994 | LaTorraca |
| 5,373,842 A | 12/1994 | Olsson et al. |
| 5,373,851 A | 12/1994 | Reinhold, Jr. et al. |
| 5,383,448 A | 1/1995 | Tkatchouk et al. |
| 5,383,449 A | 1/1995 | Forare et al. |
| 5,383,470 A | 1/1995 | Kolbly |
| 5,385,142 A | 1/1995 | Brady et al. |
| 5,390,666 A | 2/1995 | Kimm et al. |
| 5,395,301 A | 3/1995 | Russek |
| 5,398,676 A | 3/1995 | Press et al. |
| 5,398,682 A | 3/1995 | Lynn |
| 5,401,135 A | 3/1995 | Stoen et al. |
| 5,402,796 A | 4/1995 | Packer et al. |
| 5,404,871 A | 4/1995 | Goodman et al. |
| 5,407,174 A | 4/1995 | Kumar |
| 5,413,110 A | 5/1995 | Cummings et al. |
| 5,419,314 A | 5/1995 | Christopher |
| 5,429,123 A | 7/1995 | Shaffer et al. |
| 5,429,124 A | 7/1995 | Yoshida et al. |
| 5,433,193 A | 7/1995 | Sanders et al. |
| 5,435,305 A | 7/1995 | Rankin, Sr. |
| 5,438,980 A | 8/1995 | Phillips |
| 5,442,940 A | 8/1995 | Secker et al. |
| 5,443,075 A | 8/1995 | Holscher |
| 5,445,160 A | 8/1995 | Culver et al. |
| 5,446,449 A | 8/1995 | Lhomer et al. |
| 5,448,996 A | 9/1995 | Bellin et al. |
| 5,452,714 A | 9/1995 | Anderson et al. |
| 5,456,264 A | 10/1995 | Series et al. |
| 5,458,137 A | 10/1995 | Axe et al. |
| 5,464,410 A | 11/1995 | Skeens et al. |
| 5,471,977 A | 12/1995 | Olsson et al. |
| 5,474,062 A | 12/1995 | DeVires et al. |
| 5,477,860 A | 12/1995 | Essen Moller |
| 5,479,920 A | 1/1996 | Piper et al. |
| 5,479,939 A | 1/1996 | Ogino |
| 5,485,833 A | 1/1996 | Dietz |
| 5,487,383 A | 1/1996 | Levinson |
| 5,487,731 A | 1/1996 | Denton |
| 5,494,028 A | 2/1996 | DeVries et al. |
| 5,495,848 A | 3/1996 | Aylsworth et al. |
| 5,497,767 A | 3/1996 | Olsson et al. |
| 5,501,231 A | 3/1996 | Kaish |
| 5,503,146 A | 4/1996 | Froehlich et al. |
| 5,507,291 A | 4/1996 | Stirbl et al. |
| 5,513,631 A | 5/1996 | McWilliams |
| 5,517,983 A | 5/1996 | Deighan et al. |
| 5,517,985 A | 5/1996 | Kirk et al. |
| 5,518,002 A | 5/1996 | Wolf et al. |
| 5,520,071 A | 5/1996 | Jones |
| 5,522,382 A | 6/1996 | Sullivan et al. |
| 5,524,615 A | 6/1996 | Power |
| 5,524,616 A | 6/1996 | Smith et al. |
| 5,531,221 A | 7/1996 | Power |
| 5,534,851 A | 7/1996 | Russek |
| 5,535,738 A | 7/1996 | Estes et al. |
| 5,537,992 A | 7/1996 | Bjoernstijerna et al. |
| 5,537,999 A | 7/1996 | Dearman et al. |
| 5,540,218 A | 7/1996 | Jones et al. |
| 5,540,220 A | 7/1996 | Gropper et al. |
| 5,542,410 A | 8/1996 | Goodman et al. |
| 5,542,415 A | 8/1996 | Brody |
| 5,542,416 A | 8/1996 | Chalvignac |
| 5,544,674 A | 8/1996 | Kelly |
| 5,549,106 A | 8/1996 | Gruenke et al. |
| 5,549,117 A | 8/1996 | Tacklind et al. |
| 5,549,655 A | 8/1996 | Erickson |
| 5,551,418 A | 9/1996 | Estes et al. |
| 5,551,419 A | 9/1996 | Froehlich et al. |
| 5,553,620 A | 9/1996 | Snider et al. |
| 5,558,086 A | 9/1996 | Smith et al. |
| 5,560,353 A | 10/1996 | Willemot et al. |
| 5,562,918 A | 10/1996 | Stimpson |

(56) References Cited

U.S. PATENT DOCUMENTS

| | | |
|---|---|---|
| 5,564,414 A | 10/1996 | Walker et al. |
| 5,564,416 A | 10/1996 | Jones |
| 5,564,432 A | 10/1996 | Thomson |
| 5,571,142 A | 11/1996 | Brown et al. |
| 5,575,283 A | 11/1996 | Sjoestrand |
| 5,582,163 A | 12/1996 | Bonassa |
| 5,582,167 A | 12/1996 | Joseph |
| 5,582,182 A | 12/1996 | Hillsman |
| 5,590,648 A | 1/1997 | Mitchell et al. |
| 5,590,651 A | 1/1997 | Shaffer et al. |
| 5,591,130 A | 1/1997 | Denton |
| 5,596,983 A | 1/1997 | Zander et al. |
| 5,596,984 A | 1/1997 | O'Mahony et al. |
| 5,603,315 A | 2/1997 | Sasso, Jr. |
| 5,603,316 A | 2/1997 | Coufal et al. |
| 5,606,968 A | 3/1997 | Mang |
| 5,606,976 A | 3/1997 | Marshall et al. |
| 5,608,647 A | 3/1997 | Rubsamen et al. |
| 5,611,335 A | 3/1997 | Makhoul et al. |
| 5,626,144 A | 5/1997 | Tacklind et al. |
| 5,630,411 A | 5/1997 | Holscher |
| 5,632,269 A | 5/1997 | Zdrojkowski |
| 5,632,270 A | 5/1997 | O'Mahony et al. |
| 5,632,281 A | 5/1997 | Rayburn |
| 5,634,461 A | 6/1997 | Faithfull et al. |
| 5,634,471 A | 6/1997 | Fairfax et al. |
| 5,642,726 A | 7/1997 | Owens et al. |
| 5,642,735 A | 7/1997 | Kolbly |
| 5,645,048 A | 7/1997 | Brodsky et al. |
| 5,645,053 A | 7/1997 | Remmers et al. |
| 5,647,345 A | 7/1997 | Saul |
| 5,647,346 A | 7/1997 | Holscher |
| 5,647,351 A | 7/1997 | Weismann et al. |
| 5,651,264 A | 7/1997 | Lo et al. |
| 5,651,361 A | 7/1997 | Dearman et al. |
| 5,655,516 A | 8/1997 | Goodman et al. |
| 5,655,519 A | 8/1997 | Alfery |
| 5,660,168 A | 8/1997 | Ottosson et al. |
| 5,660,171 A | 8/1997 | Kimm et al. |
| 5,662,099 A | 9/1997 | Tobia et al. |
| 5,664,560 A | 9/1997 | Merrick et al. |
| 5,664,562 A | 9/1997 | Bourdon |
| 5,669,379 A | 9/1997 | Somerson et al. |
| 5,671,734 A | 9/1997 | Pugh |
| 5,671,767 A | 9/1997 | Kelly |
| 5,672,041 A | 9/1997 | Ringdahl et al. |
| 5,673,689 A | 10/1997 | Power |
| 5,676,129 A | 10/1997 | Rocci, Jr. et al. |
| 5,676,132 A | 10/1997 | Tillotson et al. |
| 5,678,539 A | 10/1997 | Schubert et al. |
| 5,683,424 A | 11/1997 | Brown et al. |
| 5,685,318 A | 11/1997 | Elghazzawi |
| 5,687,713 A | 11/1997 | Bahr et al. |
| 5,692,497 A | 12/1997 | Schnitzer et al. |
| 5,694,924 A | 12/1997 | Cewers |
| 5,704,346 A | 1/1998 | Inoue |
| 5,704,366 A | 1/1998 | Tacklind et al. |
| 5,704,367 A | 1/1998 | Ishikawa et al. |
| 5,706,799 A | 1/1998 | Imai et al. |
| 5,706,801 A | 1/1998 | Remes et al. |
| 5,715,812 A | 2/1998 | Deighan et al. |
| 5,720,276 A | 2/1998 | Kobatake et al. |
| 5,720,277 A | 2/1998 | Olsson et al. |
| 5,724,962 A | 3/1998 | Vidgren et al. |
| 5,724,990 A | 3/1998 | Ogino |
| 5,727,562 A | 3/1998 | Beck |
| 5,730,121 A | 3/1998 | Hawkins, Jr. et al. |
| 5,730,140 A | 3/1998 | Fitch |
| 5,730,145 A | 3/1998 | Defares et al. |
| 5,735,267 A | 4/1998 | Tobia |
| 5,735,287 A | 4/1998 | Thomson |
| 5,738,090 A | 4/1998 | Lachmann et al. |
| 5,738,092 A | 4/1998 | Mock et al. |
| 5,740,792 A | 4/1998 | Ashley et al. |
| 5,740,796 A | 4/1998 | Skog |
| 5,740,797 A | 4/1998 | Dickson |
| 5,743,267 A | 4/1998 | Nikolic et al. |
| 5,752,506 A | 5/1998 | Richardson |
| 5,752,509 A | 5/1998 | Lachmann et al. |
| 5,755,218 A | 5/1998 | Johansson et al. |
| 5,758,652 A | 6/1998 | Nikolic |
| 5,762,480 A | 6/1998 | Adahan |
| 5,765,558 A | 6/1998 | Psaros et al. |
| 5,771,884 A | 6/1998 | Yarnall et al. |
| 5,778,874 A | 7/1998 | Maguire et al. |
| 5,791,339 A | 8/1998 | Winter |
| 5,794,612 A | 8/1998 | Wachter et al. |
| 5,794,615 A | 8/1998 | Estes |
| 5,794,986 A | 8/1998 | Gansel et al. |
| 5,800,361 A | 9/1998 | Rayburn |
| 5,803,065 A | 9/1998 | Zdrojkowski et al. |
| 5,803,066 A | 9/1998 | Rapoport et al. |
| 5,806,512 A | 9/1998 | Abramov et al. |
| 5,806,514 A | 9/1998 | Mock et al. |
| 5,807,245 A | 9/1998 | Aldestam et al. |
| 5,809,997 A | 9/1998 | Wolf |
| 5,810,000 A | 9/1998 | Stevens |
| 5,810,741 A | 9/1998 | Essen Moller |
| 5,813,397 A | 9/1998 | Goodman et al. |
| 5,813,399 A | 9/1998 | Isaza et al. |
| 5,813,401 A | 9/1998 | Radcliff et al. |
| 5,814,086 A | 9/1998 | Hirschberg et al. |
| 5,819,723 A | 10/1998 | Joseph |
| 5,822,715 A | 10/1998 | Worthington et al. |
| 5,826,570 A | 10/1998 | Goodman et al. |
| 5,826,575 A | 10/1998 | Lall |
| 5,827,179 A | 10/1998 | Lichter et al. |
| 5,829,441 A | 11/1998 | Kidd et al. |
| 5,832,916 A | 11/1998 | Lundberg |
| 5,832,919 A | 11/1998 | Kano et al. |
| 5,839,430 A | 11/1998 | Cama |
| 5,860,418 A | 1/1999 | Lundberg |
| 5,864,938 A | 2/1999 | Gansel et al. |
| 5,865,168 A | 2/1999 | Isaza |
| 5,865,171 A | 2/1999 | Cinquin |
| 5,865,173 A | 2/1999 | Froehlich |
| 5,865,174 A | 2/1999 | Kloeppel |
| 5,868,133 A | 2/1999 | DeVries et al. |
| 5,875,777 A | 3/1999 | Eriksson |
| 5,876,352 A | 3/1999 | Weismann |
| 5,876,353 A | 3/1999 | Riff |
| 5,878,744 A | 3/1999 | Pfeiffer |
| 5,881,717 A | 3/1999 | Isaza |
| 5,881,723 A | 3/1999 | Wallace et al. |
| 5,881,725 A | 3/1999 | Hoffman et al. |
| 5,884,622 A | 3/1999 | Younes |
| 5,884,623 A | 3/1999 | Winter |
| 5,891,023 A | 4/1999 | Lynn |
| 5,899,203 A | 5/1999 | Defares et al. |
| 5,906,203 A | 5/1999 | Klockseth et al. |
| 5,909,731 A | 6/1999 | O'Mahony et al. |
| 5,911,218 A | 6/1999 | DiMarco |
| 5,915,379 A | 6/1999 | Wallace et al. |
| 5,915,380 A | 6/1999 | Wallace et al. |
| 5,915,381 A | 6/1999 | Nord |
| 5,915,382 A | 6/1999 | Power |
| 5,918,597 A | 7/1999 | Jones et al. |
| 5,921,238 A | 7/1999 | Bourdon |
| 5,921,920 A | 7/1999 | Marshall et al. |
| 5,924,418 A | 7/1999 | Lewis |
| 5,927,274 A | 7/1999 | Servidio et al. |
| 5,931,160 A | 8/1999 | Gilmore et al. |
| 5,931,162 A | 8/1999 | Christian |
| 5,932,812 A | 8/1999 | Delsing |
| 5,934,274 A | 8/1999 | Merrick et al. |
| 5,937,853 A | 8/1999 | Strom |
| 5,937,854 A | 8/1999 | Stenzler |
| 5,944,680 A | 8/1999 | Christopherson |
| 5,956,501 A | 9/1999 | Brown |
| 5,957,861 A | 9/1999 | Combs et al. |
| 5,964,218 A | 10/1999 | Smith et al. |
| 5,970,975 A | 10/1999 | Estes et al. |
| 5,971,937 A | 10/1999 | Ekstrom |
| 5,975,081 A | 11/1999 | Hood et al. |

(56) References Cited

U.S. PATENT DOCUMENTS

| | | |
|---|---|---|
| 5,979,440 A | 11/1999 | Honkonen et al. |
| 5,980,466 A | 11/1999 | Thomson |
| 5,996,580 A | 12/1999 | Swann |
| 6,000,396 A | 12/1999 | Melker et al. |
| 6,012,450 A | 1/2000 | Rubsamen |
| 6,015,388 A | 1/2000 | Sackner et al. |
| 6,016,442 A * | 1/2000 | Hsu .............. A61N 1/37247 600/518 |
| 6,017,315 A | 1/2000 | Starr et al. |
| 6,019,100 A | 2/2000 | Alving et al. |
| 6,024,089 A | 2/2000 | Wallace et al. |
| 6,026,323 A | 2/2000 | Skladnev et al. |
| 6,029,660 A | 2/2000 | Calluaud et al. |
| 6,029,664 A | 2/2000 | Zdrojkowski et al. |
| 6,032,119 A | 2/2000 | Brown et al. |
| 6,041,780 A | 3/2000 | Richard et al. |
| 6,044,841 A | 4/2000 | Verdun et al. |
| 6,047,860 A | 4/2000 | Sanders |
| 6,055,506 A | 4/2000 | Frasca, Jr. |
| 6,055,981 A | 5/2000 | Laswick et al. |
| 6,066,101 A | 5/2000 | Johnson et al. |
| 6,068,602 A | 5/2000 | Tham et al. |
| 6,073,110 A | 6/2000 | Rhodes et al. |
| 6,076,519 A | 6/2000 | Johnson |
| 6,076,523 A | 6/2000 | Jones et al. |
| 6,085,747 A | 7/2000 | Axe |
| 6,095,140 A | 8/2000 | Poon et al. |
| 6,099,481 A | 8/2000 | Daniels et al. |
| 6,106,481 A | 8/2000 | Cohen |
| 6,109,259 A | 8/2000 | Fitzgerald |
| 6,109,260 A | 8/2000 | Bathe |
| 6,112,744 A | 9/2000 | Hognelid |
| 6,116,240 A | 9/2000 | Merrick et al. |
| 6,116,464 A | 9/2000 | Sanders |
| 6,118,847 A | 9/2000 | Hernandez-Guerra et al. |
| 6,119,684 A | 9/2000 | Nohl et al. |
| 6,123,073 A | 9/2000 | Schlawin et al. |
| 6,131,571 A | 10/2000 | Lampotang et al. |
| 6,131,572 A | 10/2000 | Heinonen |
| 6,135,105 A | 10/2000 | Lampotang et al. |
| 6,135,106 A | 10/2000 | Dirks et al. |
| 6,138,675 A | 10/2000 | Berthon-Jones |
| 6,139,506 A | 10/2000 | Heinonen |
| 6,142,150 A | 11/2000 | O'Mahoney |
| 6,148,814 A | 11/2000 | Clemmer et al. |
| 6,148,815 A | 11/2000 | Wolf |
| 6,152,129 A | 11/2000 | Berthon Jones |
| 6,152,133 A | 11/2000 | Psaros et al. |
| 6,152,135 A | 11/2000 | DeVries et al. |
| 6,155,257 A | 12/2000 | Lurie et al. |
| 6,158,432 A | 12/2000 | Biondi et al. |
| 6,158,433 A | 12/2000 | Ong et al. |
| 6,159,147 A | 12/2000 | Lichter et al. |
| 6,161,539 A | 12/2000 | Winter |
| 6,162,183 A | 12/2000 | Hoover |
| 6,167,362 A | 12/2000 | Brown et al. |
| 6,168,568 B1 | 1/2001 | Gavriely |
| 6,171,264 B1 | 1/2001 | Bader |
| 6,176,833 B1 | 1/2001 | Thomson |
| 6,186,956 B1 | 2/2001 | McNamee |
| 6,190,326 B1 | 2/2001 | McKinnon et al. |
| 6,192,876 B1 | 2/2001 | Denyer et al. |
| 6,192,885 B1 | 2/2001 | Jalde |
| 6,196,222 B1 | 3/2001 | Heinonen et al. |
| 6,198,963 B1 | 3/2001 | Haim et al. |
| 6,199,550 B1 | 3/2001 | Wiesmann et al. |
| 6,202,642 B1 | 3/2001 | McKinnon et al. |
| 6,213,119 B1 | 4/2001 | Brydon et al. |
| 6,213,120 B1 | 4/2001 | Block et al. |
| 6,213,955 B1 | 4/2001 | Karakasoglu et al. |
| 6,216,690 B1 | 4/2001 | Keitel et al. |
| 6,220,244 B1 | 4/2001 | McLaughlin |
| 6,220,245 B1 | 4/2001 | Takabayashi et al. |
| 6,223,744 B1 | 5/2001 | Garon |
| 6,224,553 B1 | 5/2001 | Nevo |
| 6,227,197 B1 | 5/2001 | Fitzgerald |
| 6,230,708 B1 | 5/2001 | Radko |
| 6,233,539 B1 | 5/2001 | Brown |
| 6,234,963 B1 | 5/2001 | Blike et al. |
| 6,240,920 B1 | 6/2001 | Ström |
| 6,251,082 B1 | 6/2001 | Rayburn |
| 6,257,234 B1 | 7/2001 | Sun |
| 6,258,039 B1 | 7/2001 | Okamoto et al. |
| 6,260,549 B1 | 7/2001 | Sosiak |
| 6,261,238 B1 | 7/2001 | Gavriely |
| 6,269,810 B1 | 8/2001 | Brooker et al. |
| 6,269,812 B1 | 8/2001 | Wallace et al. |
| 6,273,088 B1 | 8/2001 | Hillsman |
| 6,273,444 B1 | 8/2001 | Power |
| 6,279,569 B1 | 8/2001 | Berthon Jones |
| 6,279,574 B1 | 8/2001 | Richardson et al. |
| 6,283,119 B1 | 9/2001 | Bourdon |
| 6,283,923 B1 | 9/2001 | Finkelstein et al. |
| 6,287,264 B1 | 9/2001 | Hoffman |
| 6,301,497 B1 | 10/2001 | Neustadter |
| 6,302,106 B1 | 10/2001 | Lewis |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,308,703 B1 | 10/2001 | Alving et al. |
| 6,308,706 B1 | 10/2001 | Lammers et al. |
| 6,318,365 B1 | 11/2001 | Vogele et al. |
| 6,321,748 B1 | 11/2001 | O'Mahoney |
| 6,322,502 B1 | 11/2001 | Schoenberg et al. |
| 6,325,785 B1 | 12/2001 | Babkes et al. |
| 6,339,410 B1 | 1/2002 | Milner et al. |
| 6,340,348 B1 | 1/2002 | Krishnan et al. |
| 6,341,604 B1 | 1/2002 | Kellon |
| 6,342,040 B1 | 1/2002 | Starr et al. |
| 6,343,603 B1 | 2/2002 | Tuck et al. |
| 6,345,619 B1 | 2/2002 | Finn |
| 6,349,722 B1 | 2/2002 | Gradon et al. |
| 6,349,724 B1 | 2/2002 | Burton et al. |
| 6,355,002 B1 | 3/2002 | Faram et al. |
| 6,357,438 B1 | 3/2002 | Hansen |
| 6,360,740 B1 | 3/2002 | Ward et al. |
| 6,360,745 B1 | 3/2002 | Wallace et al. |
| 6,362,620 B1 | 3/2002 | Debbins et al. |
| 6,367,475 B1 | 4/2002 | Kofoed et al. |
| 6,369,838 B1 | 4/2002 | Wallace et al. |
| 6,370,419 B1 | 4/2002 | Lampotang et al. |
| 6,377,046 B1 | 4/2002 | Debbins et al. |
| 6,379,301 B1 | 4/2002 | Worthington et al. |
| 6,390,088 B1 | 5/2002 | Nohl et al. |
| 6,390,091 B1 | 5/2002 | Banner et al. |
| 6,390,092 B1 | 5/2002 | Leenhoven |
| 6,390,977 B1 | 5/2002 | Faithfull et al. |
| 6,390,988 B1 | 5/2002 | Robinson |
| 6,397,838 B1 | 6/2002 | Zimlich, Jr. et al. |
| 6,402,698 B1 | 6/2002 | Mault |
| 6,408,043 B1 | 6/2002 | Hu et al. |
| 6,408,847 B1 | 6/2002 | Nuckols et al. |
| 6,412,482 B1 | 7/2002 | Rowe |
| 6,412,483 B1 | 7/2002 | Jones et al. |
| 6,415,792 B1 | 7/2002 | Schoolman |
| 6,416,471 B1 | 7/2002 | Kumar et al. |
| 6,421,650 B1 | 7/2002 | Goetz et al. |
| 6,425,392 B1 | 7/2002 | Sosiak |
| 6,427,687 B1 | 8/2002 | Kirk |
| 6,435,175 B1 | 8/2002 | Stenzler |
| 6,436,053 B1 | 8/2002 | Knapp, II et al. |
| 6,439,229 B1 | 8/2002 | Du et al. |
| 6,446,630 B1 | 9/2002 | Todd, Jr. |
| 6,450,163 B1 | 9/2002 | Blacker et al. |
| 6,450,164 B1 | 9/2002 | Banner et al. |
| 6,450,968 B1 | 9/2002 | Wallen et al. |
| 6,454,708 B1 | 9/2002 | Ferguson et al. |
| 6,457,472 B1 | 10/2002 | Schwartz et al. |
| 6,459,933 B1 | 10/2002 | Lurie et al. |
| 6,461,315 B1 | 10/2002 | Gattinoni |
| 6,463,930 B2 | 10/2002 | Biondi et al. |
| 6,467,477 B1 | 10/2002 | Frank et al. |
| 6,467,478 B1 | 10/2002 | Merrick et al. |
| 6,467,479 B1 | 10/2002 | Albert et al. |

(56) References Cited

U.S. PATENT DOCUMENTS

| | | |
|---|---|---|
| 6,467,481 B1 | 10/2002 | Eswarappa |
| 6,471,658 B1 | 10/2002 | Daniels et al. |
| 6,484,719 B1 | 11/2002 | Berthon Jones |
| 6,488,029 B1 | 12/2002 | Hood et al. |
| 6,488,629 B1 | 12/2002 | Saetre et al. |
| 6,488,634 B1 | 12/2002 | Rapoport |
| 6,494,201 B1 | 12/2002 | Welik |
| RE37,970 E | 1/2003 | Costello, Jr. |
| 6,510,851 B2 | 1/2003 | Rydin |
| 6,511,426 B1 | 1/2003 | Hossack et al. |
| 6,512,938 B2 | 1/2003 | Claure et al. |
| 6,515,683 B1 | 2/2003 | Wright |
| 6,516,800 B1 | 2/2003 | Bowden |
| 6,517,497 B2 | 2/2003 | Rymut et al. |
| 6,523,538 B1 | 2/2003 | Wikfeldt |
| 6,526,970 B2 | 3/2003 | DeVries et al. |
| 6,532,956 B2 | 3/2003 | Hill |
| 6,532,957 B2 | 3/2003 | Berthon Jones |
| 6,532,959 B1 | 3/2003 | Berthon Jones |
| 6,533,723 B1 | 3/2003 | Lockery et al. |
| 6,533,730 B2 | 3/2003 | Strom |
| 6,536,433 B1 | 3/2003 | Cewers |
| 6,537,228 B1 | 3/2003 | Lambert |
| 6,539,938 B2 | 4/2003 | Weinstein et al. |
| 6,539,940 B2 | 4/2003 | Zdrojkowski et al. |
| 6,543,449 B1 | 4/2003 | Woodring et al. |
| 6,543,701 B1 | 4/2003 | Ho |
| 6,544,192 B2 | 4/2003 | Starr et al. |
| 6,546,930 B1 | 4/2003 | Emerson et al. |
| 6,547,728 B1 | 4/2003 | Cornuejols |
| 6,547,743 B2 | 4/2003 | Brydon |
| 6,553,991 B1 | 4/2003 | Isaza |
| 6,553,992 B1 | 4/2003 | Berthon Jones et al. |
| 6,557,553 B1 | 5/2003 | Borrello |
| 6,557,554 B1 | 5/2003 | Sugiura |
| 6,564,798 B1 | 5/2003 | Jalde |
| 6,566,875 B1 | 5/2003 | Hasson et al. |
| 6,571,122 B2 | 5/2003 | Schroeppel et al. |
| 6,571,795 B2 | 6/2003 | Bourdon |
| 6,571,796 B2 | 6/2003 | Banner et al. |
| 6,575,163 B1 | 6/2003 | Berthon Jones |
| 6,575,164 B1 | 6/2003 | Jaffe et al. |
| 6,577,884 B1 | 6/2003 | Boas |
| 6,578,575 B1 | 6/2003 | Jonson |
| 6,581,592 B1 | 6/2003 | Bathe et al. |
| 6,581,599 B1 | 6/2003 | Stenzler |
| 6,584,973 B1 | 7/2003 | Biondi et al. |
| 6,588,423 B1 | 7/2003 | Sinderby |
| 6,589,188 B1 | 7/2003 | Street |
| 6,595,212 B1 | 7/2003 | Arnott |
| 6,595,213 B2 | 7/2003 | Bennarsten |
| 6,597,939 B1 | 7/2003 | Lampotang et al. |
| 6,599,252 B2 | 7/2003 | Starr |
| 6,601,583 B2 | 8/2003 | Pessala et al. |
| 6,603,494 B1 | 8/2003 | Banks et al. |
| 6,606,993 B1 | 8/2003 | Wiesmann et al. |
| 6,607,481 B1 | 8/2003 | Clawson |
| 6,609,517 B1 | 8/2003 | Estes et al. |
| 6,609,518 B1 | 8/2003 | Lamb |
| 6,620,106 B2 | 9/2003 | Mault |
| 6,621,917 B1 | 9/2003 | Vilser |
| 6,622,725 B1 | 9/2003 | Fisher et al. |
| 6,622,726 B1 | 9/2003 | Du |
| 6,626,175 B2 | 9/2003 | Jafari et al. |
| 6,626,176 B1 | 9/2003 | Madaus |
| 6,629,934 B2 | 10/2003 | Mault et al. |
| 6,630,176 B2 | 10/2003 | Li et al. |
| 6,631,716 B1 | 10/2003 | Robinson et al. |
| 6,631,717 B1 | 10/2003 | Rich et al. |
| 6,644,310 B1 | 11/2003 | Delache et al. |
| 6,644,312 B2 | 11/2003 | Berthon-Jones et al. |
| 6,645,158 B2 | 11/2003 | Mault |
| 6,650,346 B1 | 11/2003 | Jaeger et al. |
| 6,651,652 B1 | 11/2003 | Ward |
| 6,651,653 B1 | 11/2003 | Honkonen et al. |
| 6,651,657 B1 | 11/2003 | Manigel et al. |
| 6,655,383 B1 | 12/2003 | Lundberg |
| 6,656,129 B2 | 12/2003 | Niles et al. |
| 6,659,101 B2 | 12/2003 | Berthon Jones |
| 6,659,961 B2 | 12/2003 | Robinson |
| 6,663,574 B2 | 12/2003 | Faram |
| 6,668,824 B1 | 12/2003 | Isaza et al. |
| 6,668,829 B2 | 12/2003 | Biondi et al. |
| 6,671,529 B2 | 12/2003 | Claure et al. |
| 6,673,018 B2 | 1/2004 | Friedman |
| 6,675,801 B2 | 1/2004 | Wallace et al. |
| 6,679,258 B1 | 1/2004 | Strom |
| 6,681,643 B2 | 1/2004 | Heinonen |
| 6,681,764 B1 | 1/2004 | Honkonen et al. |
| 6,688,307 B2 | 2/2004 | Berthon Jones |
| 6,689,091 B2 | 2/2004 | Bui et al. |
| 6,694,978 B1 | 2/2004 | Bennarsten |
| 6,698,423 B1 | 3/2004 | Honkonen et al. |
| 6,707,476 B1 | 3/2004 | Hochstedler |
| 6,708,688 B1 | 3/2004 | Rubin et al. |
| 6,709,405 B2 | 3/2004 | Jonson |
| 6,712,762 B1 | 3/2004 | Lichter et al. |
| 6,718,974 B1 | 4/2004 | Moberg |
| 6,718,975 B2 | 4/2004 | Blomberg |
| 6,722,360 B2 | 4/2004 | Doshi |
| 6,725,077 B1 | 4/2004 | Balloni et al. |
| 6,725,447 B1 | 4/2004 | Gilman et al. |
| 6,725,860 B2 | 4/2004 | Wallroth et al. |
| 6,726,598 B1 | 4/2004 | Jarvis et al. |
| 6,733,449 B1 | 5/2004 | Krishnamurthy et al. |
| 6,738,079 B1 | 5/2004 | Kellerman et al. |
| 6,739,336 B1 | 5/2004 | Jalde |
| 6,739,337 B2 | 5/2004 | Isaza |
| 6,740,046 B2 | 5/2004 | Knapp, II et al. |
| 6,743,172 B1 | 6/2004 | Blike |
| 6,744,374 B1 | 6/2004 | Kuenzner |
| 6,745,764 B2 | 6/2004 | Hickle |
| 6,745,771 B2 | 6/2004 | Castor et al. |
| 6,745,773 B1 | 6/2004 | Gobel |
| 6,752,766 B2 | 6/2004 | Kowallik et al. |
| 6,752,772 B2 | 6/2004 | Kahn |
| 6,755,193 B2 | 6/2004 | Berthon Jones et al. |
| 6,755,787 B2 | 6/2004 | Hossack et al. |
| 6,758,216 B1 | 7/2004 | Berthon Jones et al. |
| 6,760,610 B2 | 7/2004 | Tschupp et al. |
| 6,761,167 B1 | 7/2004 | Nadjafizadeh et al. |
| 6,761,168 B1 | 7/2004 | Nadjafizadeh et al. |
| 6,763,829 B2 | 7/2004 | Jaffe et al. |
| 6,776,159 B2 | 8/2004 | Pelerossi et al. |
| 6,782,888 B1 | 8/2004 | Friberg et al. |
| 6,786,217 B2 | 9/2004 | Stenzler |
| 6,790,178 B1 | 9/2004 | Mault et al. |
| 6,792,066 B2 | 9/2004 | Harder et al. |
| 6,796,305 B1 | 9/2004 | Banner et al. |
| 6,801,227 B2 | 10/2004 | Bocionek et al. |
| 6,801,802 B2 | 10/2004 | Sitzman et al. |
| 6,805,118 B2 | 10/2004 | Brooker et al. |
| 6,807,965 B1 | 10/2004 | Hickle |
| 6,810,876 B2 | 11/2004 | Berthon Jones |
| 6,814,073 B2 | 11/2004 | Wickham |
| 6,814,074 B1 | 11/2004 | Nadjafizadeh et al. |
| 6,814,075 B2 | 11/2004 | Boussignac |
| 6,820,613 B2 | 11/2004 | Wenkebach et al. |
| 6,820,614 B2 | 11/2004 | Bonutti |
| 6,820,618 B2 | 11/2004 | Banner et al. |
| 6,822,223 B2 | 11/2004 | Davis |
| 6,823,866 B2 | 11/2004 | Jafari et al. |
| 6,824,520 B2 | 11/2004 | Orr et al. |
| 6,828,910 B2 | 12/2004 | VanRyzin et al. |
| 6,830,046 B2 | 12/2004 | Blakley et al. |
| 6,834,647 B2 | 12/2004 | Blair et al. |
| 6,837,241 B2 | 1/2005 | Samzelius |
| 6,837,242 B2 | 1/2005 | Younes |
| 6,839,753 B2 | 1/2005 | Biondi et al. |
| 6,840,240 B1 | 1/2005 | Berthon Jones et al. |
| 6,845,773 B2 | 1/2005 | Berthon-Jones et al. |
| 6,848,444 B2 | 2/2005 | Smith et al. |
| 6,851,427 B1 | 2/2005 | Nashed |
| 6,854,462 B2 | 2/2005 | Berthon-Jones |

(56) References Cited

U.S. PATENT DOCUMENTS

| | | |
|---|---|---|
| 6,858,006 B2 | 2/2005 | MacCarter et al. |
| 6,860,264 B2 | 3/2005 | Christopher |
| 6,860,265 B1 | 3/2005 | Emerson |
| 6,860,266 B2 | 3/2005 | Blike |
| 6,860,858 B2 | 3/2005 | Green et al. |
| 6,863,068 B2 | 3/2005 | Jamison et al. |
| 6,863,656 B2 | 3/2005 | Lurie |
| 6,866,040 B1 | 3/2005 | Bourdon |
| 6,866,629 B2 | 3/2005 | Bardy |
| 6,877,511 B2 | 4/2005 | DeVries et al. |
| 6,893,397 B2 | 5/2005 | Bardy |
| 6,899,101 B2 | 5/2005 | Haston et al. |
| 6,899,103 B1 | 5/2005 | Hood et al. |
| 6,899,683 B2 | 5/2005 | Mault et al. |
| 6,899,684 B2 | 5/2005 | Mault et al. |
| 6,910,480 B1 | 6/2005 | Berthon Jones |
| 6,910,481 B2 | 6/2005 | Kimmel et al. |
| 6,920,875 B1 | 7/2005 | Hill et al. |
| 6,920,878 B2 | 7/2005 | Sinderby et al. |
| 6,921,369 B1 | 7/2005 | Gehrke et al. |
| 6,923,079 B1 | 8/2005 | Snibbe |
| 6,931,269 B2 | 8/2005 | Terry |
| 6,932,083 B2 | 8/2005 | Jones et al. |
| 6,932,767 B2 | 8/2005 | Landry et al. |
| 6,938,619 B1 | 9/2005 | Hickle |
| 6,947,780 B2 | 9/2005 | Scharf |
| 6,948,497 B2 | 9/2005 | Zdrojkowski et al. |
| 6,949,133 B2 | 9/2005 | McCombs et al. |
| 6,951,217 B2 | 10/2005 | Berthon Jones |
| 6,951,541 B2 | 10/2005 | Desmarais |
| 6,954,702 B2 | 10/2005 | Pierry et al. |
| 6,956,572 B2 | 10/2005 | Zaleski |
| 6,960,854 B2 | 11/2005 | Nadjafizadeh et al. |
| 6,970,919 B1 | 11/2005 | Doi et al. |
| 6,976,487 B1 | 12/2005 | Melker et al. |
| 6,976,958 B2 | 12/2005 | Quy |
| 6,986,347 B2 | 1/2006 | Hickle |
| 6,988,498 B2 | 1/2006 | Berthon-Jones et al. |
| 6,990,977 B1 | 1/2006 | Calluaud et al. |
| 6,990,980 B2 | 1/2006 | Richey, II |
| 6,997,185 B2 | 2/2006 | Han et al. |
| 6,997,880 B2 | 2/2006 | Carlebach et al. |
| 6,997,881 B2 | 2/2006 | Green et al. |
| 7,000,612 B2 | 2/2006 | Jafari et al. |
| 7,001,339 B2 | 2/2006 | Lin |
| 7,001,340 B2 | 2/2006 | Lin |
| 7,008,380 B1 | 3/2006 | Rees et al. |
| 7,011,091 B2 | 3/2006 | Hill et al. |
| 7,011,092 B2 | 3/2006 | McCombs et al. |
| 7,013,892 B2 | 3/2006 | Estes et al. |
| 7,017,574 B2 | 3/2006 | Biondi et al. |
| 7,019,652 B2 | 3/2006 | Richardson |
| 7,033,323 B2 | 4/2006 | Botbol et al. |
| 7,036,504 B2 | 5/2006 | Wallace et al. |
| 7,039,878 B2 | 5/2006 | Auer et al. |
| 7,040,315 B1 | 5/2006 | Strömberg |
| 7,040,318 B2 | 5/2006 | Däscher et al. |
| 7,040,320 B2 | 5/2006 | Fjeld et al. |
| 7,040,321 B2 | 5/2006 | Gobel et al. |
| 7,046,254 B2 | 5/2006 | Brown et al. |
| 7,047,092 B2 | 5/2006 | Wimsatt |
| 7,051,736 B2 | 5/2006 | Banner et al. |
| 7,055,522 B2 | 6/2006 | Berthon Jones |
| 7,062,251 B2 | 6/2006 | Birkett et al. |
| 7,066,173 B2 | 6/2006 | Banner et al. |
| 7,066,175 B2 | 6/2006 | Hamilton et al. |
| 7,066,176 B2 | 6/2006 | Jaffe et al. |
| 7,070,570 B2 | 7/2006 | Sanderson et al. |
| 7,077,125 B2 | 7/2006 | Scheuch |
| 7,077,131 B2 | 7/2006 | Hansen |
| 7,077,132 B2 | 7/2006 | Berthon-Jones |
| 7,080,646 B2 | 7/2006 | Wiesmann et al. |
| 7,081,091 B2 | 7/2006 | Merrett et al. |
| 7,081,095 B2 | 7/2006 | Lynn et al. |
| RE39,225 E | 8/2006 | Isaza et al. |
| 7,083,574 B2 | 8/2006 | Kline |
| 7,086,098 B2 | 8/2006 | Sallvin |
| 7,087,027 B2 | 8/2006 | Page |
| 7,089,927 B2 | 8/2006 | John et al. |
| 7,089,930 B2 | 8/2006 | Adams et al. |
| 7,089,932 B2 | 8/2006 | Dodds |
| 7,089,936 B2 | 8/2006 | Madaus |
| 7,089,937 B2 | 8/2006 | Berthon Jones et al. |
| 7,094,208 B2 | 8/2006 | Williams et al. |
| 7,100,607 B2 | 9/2006 | Zdrojkowski et al. |
| 7,100,609 B2 | 9/2006 | Berthon Jones et al. |
| 7,104,962 B2 | 9/2006 | Lomask et al. |
| 7,116,810 B2 | 10/2006 | Miller et al. |
| 7,117,438 B2 | 10/2006 | Wallace et al. |
| 7,121,277 B2 | 10/2006 | Ström |
| 7,128,069 B2 | 10/2006 | Farrugia et al. |
| 7,128,578 B2 | 10/2006 | Lampotang et al. |
| 7,137,389 B2 | 11/2006 | Berthon Jones |
| 7,147,600 B2 | 12/2006 | Bardy |
| 7,152,598 B2 | 12/2006 | Morris et al. |
| 7,152,604 B2 | 12/2006 | Hickle et al. |
| 7,156,095 B2 | 1/2007 | Melker et al. |
| 7,156,808 B2 | 1/2007 | Quy |
| 7,159,588 B2 | 1/2007 | Wickham |
| 7,162,296 B2 | 1/2007 | Leonhardt et al. |
| 7,164,972 B2 | 1/2007 | Imhof et al. |
| 7,165,221 B2 | 1/2007 | Monteleone et al. |
| 7,169,112 B2 | 1/2007 | Caldwell |
| 7,172,557 B1 | 2/2007 | Parker |
| 7,182,083 B2 | 2/2007 | Yanof et al. |
| 7,187,790 B2 | 3/2007 | Sabol et al. |
| 7,188,621 B2 | 3/2007 | DeVries et al. |
| 7,191,780 B2 | 3/2007 | Faram |
| 7,201,734 B2 | 4/2007 | Hickle |
| 7,203,353 B2 | 4/2007 | Klotz et al. |
| 7,210,478 B2 | 5/2007 | Banner et al. |
| 7,211,049 B2 | 5/2007 | Bradley et al. |
| 7,219,666 B2 | 5/2007 | Friberg et al. |
| 7,220,230 B2 | 5/2007 | Roteliuk et al. |
| 7,222,054 B2 | 5/2007 | Geva |
| 7,223,965 B2 | 5/2007 | Davis |
| 7,226,427 B2 | 6/2007 | Steen |
| 7,228,323 B2 | 6/2007 | Angerer et al. |
| 7,241,269 B2 | 7/2007 | McCawley et al. |
| 7,246,618 B2 | 7/2007 | Habashi |
| 7,247,154 B2 | 7/2007 | Hickle |
| 7,252,640 B2 | 8/2007 | Ni et al. |
| 7,255,103 B2 | 8/2007 | Bassin |
| 7,261,690 B2 | 8/2007 | Teller et al. |
| 7,264,730 B2 | 9/2007 | Connell et al. |
| 7,267,652 B2 | 9/2007 | Coyle et al. |
| 7,270,126 B2 | 9/2007 | Wallace et al. |
| 7,275,540 B2 | 10/2007 | Bolam et al. |
| 7,276,031 B2 | 10/2007 | Norman et al. |
| 7,278,579 B2 | 10/2007 | Loffredo et al. |
| 7,282,032 B2 | 10/2007 | Miller |
| 7,285,090 B2 | 10/2007 | Stivoric et al. |
| 7,294,105 B1 | 11/2007 | Islam |
| 7,294,112 B1 | 11/2007 | Dunlop |
| 7,298,280 B2 | 11/2007 | Voege et al. |
| 7,300,418 B2 | 11/2007 | Zaleski |
| 7,303,680 B2 | 12/2007 | Connell et al. |
| 7,305,988 B2 | 12/2007 | Acker |
| 7,308,550 B2 | 12/2007 | Cornett |
| 7,310,551 B1 | 12/2007 | Koh et al. |
| 7,310,720 B2 | 12/2007 | Cornett |
| 7,311,665 B2 | 12/2007 | Hawthorne et al. |
| 7,311,668 B2 | 12/2007 | Lurie |
| 7,314,451 B2 | 1/2008 | Halperin et al. |
| 7,316,231 B2 | 1/2008 | Hickle |
| 7,318,808 B2 | 1/2008 | Tarassenko et al. |
| 7,318,892 B2 | 1/2008 | Connell et al. |
| 7,321,802 B2 | 1/2008 | Wasner et al. |
| 7,322,352 B2 | 1/2008 | Minshull et al. |
| 7,322,937 B2 | 1/2008 | Blomberg et al. |
| 7,331,340 B2 | 2/2008 | Barney |
| 7,333,969 B2 | 2/2008 | Lee et al. |
| 7,334,578 B2 | 2/2008 | Biondi et al. |
| 7,334,581 B2 | 2/2008 | Doshi |

(56) References Cited

U.S. PATENT DOCUMENTS

| | | |
|---|---|---|
| 7,343,916 B2 | 3/2008 | Biondo et al. |
| 7,343,917 B2 | 3/2008 | Jones |
| 7,347,200 B2 | 3/2008 | Jones et al. |
| 7,347,204 B1 | 3/2008 | Lindsey et al. |
| 7,347,205 B2 | 3/2008 | Levi |
| 7,347,207 B2 | 3/2008 | Ahlmen et al. |
| 7,351,340 B2 | 4/2008 | Connell et al. |
| 7,362,341 B2 | 4/2008 | McGuire et al. |
| 7,363,925 B2 | 4/2008 | Pagan |
| 7,367,337 B2 | 5/2008 | Berthon-Jones et al. |
| 7,367,955 B2 | 5/2008 | Zhang et al. |
| 7,369,757 B2 | 5/2008 | Farbarik |
| 7,370,650 B2 | 5/2008 | Nadjafizadeh et al. |
| 7,374,535 B2 | 5/2008 | Schoenberg et al. |
| 7,377,276 B2 | 5/2008 | Roy et al. |
| 7,380,210 B2 | 5/2008 | Lontka et al. |
| RE40,365 E | 6/2008 | Kirchgeorg et al. |
| 7,383,148 B2 | 6/2008 | Ahmed |
| 7,387,610 B2 | 6/2008 | Stahmann et al. |
| 7,390,304 B2 | 6/2008 | Chen et al. |
| 7,392,806 B2 | 7/2008 | Yuen et al. |
| 7,413,546 B2 | 8/2008 | Agutter et al. |
| 7,422,015 B2 | 9/2008 | Delisle et al. |
| 7,422,562 B2 | 9/2008 | Hatib et al. |
| 7,425,201 B2 | 9/2008 | Euliano et al. |
| 7,428,902 B2 | 9/2008 | Du et al. |
| 7,431,035 B2 | 10/2008 | Mizuta |
| 7,435,220 B2 | 10/2008 | Ranucci |
| 7,438,072 B2 | 10/2008 | Izuchukwu |
| 7,438,073 B2 | 10/2008 | Delache et al. |
| 7,445,006 B2 | 11/2008 | Dhuper et al. |
| 7,448,383 B2 | 11/2008 | Delache et al. |
| 7,452,333 B2 | 11/2008 | Roteliuk |
| 7,455,583 B2 | 11/2008 | Taya |
| 7,460,959 B2 | 12/2008 | Jafari |
| 7,464,339 B2 | 12/2008 | Keenan, Jr. et al. |
| 7,464,711 B2 | 12/2008 | Flodin |
| 7,467,012 B1 | 12/2008 | Park et al. |
| 7,469,698 B1 | 12/2008 | Childers et al. |
| 7,472,702 B2 | 1/2009 | Beck et al. |
| 7,484,508 B2 | 2/2009 | Younes |
| 7,487,773 B2 | 2/2009 | Li |
| 7,487,774 B2 | 2/2009 | Acker |
| 7,487,775 B2 | 2/2009 | Mashak |
| 7,487,778 B2 | 2/2009 | Freitag |
| 7,490,085 B2 | 2/2009 | Walker et al. |
| 7,495,546 B2 | 2/2009 | Lintell et al. |
| 7,496,400 B2 | 2/2009 | Hoskonen et al. |
| 7,500,481 B2 | 3/2009 | Delache et al. |
| 7,504,954 B2 | 3/2009 | Spaeder |
| 7,509,957 B2 | 3/2009 | Duquette et al. |
| 7,512,450 B2 | 3/2009 | Ahmed |
| 7,512,593 B2 | 3/2009 | Karklins et al. |
| 7,523,752 B2 | 4/2009 | Montgomery et al. |
| 7,527,053 B2 | 5/2009 | DeVries et al. |
| 7,527,054 B2 | 5/2009 | Misholi |
| 7,530,353 B2 | 5/2009 | Choncholas et al. |
| RE40,806 E | 6/2009 | Gradon et al. |
| 7,543,582 B2 | 6/2009 | Lu et al. |
| 7,547,285 B2 | 6/2009 | Kline |
| 7,548,833 B2 | 6/2009 | Ahmed |
| 7,549,421 B2 | 6/2009 | Levi et al. |
| 7,552,731 B2 | 6/2009 | Jorczak et al. |
| 7,556,036 B2 | 7/2009 | Bouillon et al. |
| 7,556,038 B2 | 7/2009 | Kirby et al. |
| 7,559,326 B2 | 7/2009 | Smith et al. |
| 7,559,903 B2 | 7/2009 | Moussavi et al. |
| 7,562,657 B2 | 7/2009 | Blanch et al. |
| 7,565,905 B2 | 7/2009 | Hickle |
| 7,572,225 B2 | 8/2009 | Stahmann et al. |
| 7,574,246 B2 | 8/2009 | Krebs et al. |
| 7,584,712 B2 | 9/2009 | Lu |
| 7,584,752 B2 | 9/2009 | Garber et al. |
| 7,588,033 B2 | 9/2009 | Wondka |
| 7,588,543 B2 | 9/2009 | Euliano et al. |
| 7,590,551 B2 | 9/2009 | Auer |
| 7,591,830 B2 | 9/2009 | Rutter |
| 7,594,508 B2 | 9/2009 | Doyle |
| 7,597,099 B2 | 10/2009 | Jones et al. |
| 7,603,170 B2 | 10/2009 | Hatlestad et al. |
| 7,603,631 B2 | 10/2009 | Bermudez et al. |
| 7,606,668 B2 | 10/2009 | Pierry et al. |
| 7,607,432 B2 | 10/2009 | Sullivan |
| 7,609,138 B2 | 10/2009 | Dietrich et al. |
| 7,610,914 B2 | 11/2009 | Bolam et al. |
| 7,610,915 B2 | 11/2009 | Dittmann |
| 7,617,821 B2 | 11/2009 | Hughes |
| 7,617,824 B2 | 11/2009 | Doyle |
| 7,617,825 B2 | 11/2009 | Pedemonte |
| 7,618,378 B2 | 11/2009 | Bingham et al. |
| 7,621,270 B2 | 11/2009 | Morris et al. |
| 7,624,736 B2 | 12/2009 | Borody |
| 7,625,345 B2 | 12/2009 | Quinn |
| 7,628,151 B2 | 12/2009 | Bassin |
| 7,630,755 B2 | 12/2009 | Stahmann et al. |
| 7,634,998 B1 | 12/2009 | Fenley |
| 7,644,713 B2 | 1/2010 | Berthon Jones |
| 7,650,181 B2 | 1/2010 | Freeman et al. |
| 7,652,571 B2 | 1/2010 | Parkulo et al. |
| 7,654,802 B2 | 2/2010 | Crawford, Jr. et al. |
| 7,654,966 B2 | 2/2010 | Westinskow et al. |
| 7,658,188 B2 | 2/2010 | Halpern et al. |
| 7,662,106 B2 | 2/2010 | Daniels et al. |
| 7,668,579 B2 | 2/2010 | Lynn |
| 7,669,594 B2 | 3/2010 | Downie |
| 7,669,598 B2 | 3/2010 | Rick et al. |
| 7,671,733 B2 | 3/2010 | McNeal et al. |
| 7,678,061 B2 | 3/2010 | Lee et al. |
| 7,678,063 B2 | 3/2010 | Felmlee et al. |
| 7,682,312 B2 | 3/2010 | Lurie |
| 7,684,931 B2 | 3/2010 | Pierry et al. |
| 7,693,697 B2 | 4/2010 | Westenskow et al. |
| 7,694,677 B2 | 4/2010 | Tang |
| 7,694,682 B2 | 4/2010 | Petersen et al. |
| 7,698,156 B2 | 4/2010 | Martucci et al. |
| 7,708,015 B2 | 5/2010 | Seeger et al. |
| 7,717,110 B2 | 5/2010 | Kane et al. |
| 7,717,112 B2 | 5/2010 | Sun et al. |
| 7,717,113 B2 | 5/2010 | Andrieux |
| 7,721,736 B2 | 5/2010 | Urias et al. |
| 7,722,546 B2 | 5/2010 | Madaus et al. |
| D618,356 S | 6/2010 | Ross |
| 7,727,160 B2 | 6/2010 | Green et al. |
| 7,731,663 B2 | 6/2010 | Averina et al. |
| 7,735,486 B2 | 6/2010 | Payne |
| 7,735,492 B2 | 6/2010 | Doshi et al. |
| 7,736,132 B2 | 6/2010 | Bliss et al. |
| 7,740,013 B2 | 6/2010 | Ishizaki et al. |
| 7,753,049 B2 | 7/2010 | Jorczak et al. |
| 7,766,012 B2 | 8/2010 | Scheuch et al. |
| 7,771,364 B2 | 8/2010 | Arbel et al. |
| 7,772,965 B2 | 8/2010 | Farhan et al. |
| 7,775,207 B2 | 8/2010 | Jaffe et al. |
| 7,778,709 B2 | 8/2010 | Gollasch et al. |
| 7,778,851 B2 | 8/2010 | Schoenberg et al. |
| 7,779,834 B2 | 8/2010 | Calluaud et al. |
| 7,784,461 B2 | 8/2010 | Figueiredo et al. |
| 7,785,263 B2 | 8/2010 | Roteliuk et al. |
| 7,785,265 B2 | 8/2010 | Schätzl |
| 7,793,656 B2 | 9/2010 | Johnson |
| 7,793,659 B2 | 9/2010 | Breen |
| 7,793,660 B2 | 9/2010 | Kimmel et al. |
| 7,798,145 B2 | 9/2010 | Weismann et al. |
| 7,802,571 B2 | 9/2010 | Tehrani |
| 7,809,442 B2 | 10/2010 | Bolea et al. |
| 7,810,496 B2 | 10/2010 | Estes et al. |
| 7,810,497 B2 | 10/2010 | Pittman et al. |
| 7,810,498 B1 | 10/2010 | Patterson |
| 7,814,906 B2 | 10/2010 | Moretti |
| 7,819,815 B2 | 10/2010 | Younes |
| 7,823,588 B2 | 11/2010 | Hansen |
| 7,831,450 B2 | 11/2010 | Schoenberg et al. |
| 7,832,394 B2 | 11/2010 | Schechter et al. |
| 7,836,882 B1 | 11/2010 | Rumph et al. |

(56) References Cited

U.S. PATENT DOCUMENTS

| | | |
|---|---|---|
| 7,837,629 B2 | 11/2010 | Bardy |
| 7,841,341 B2 | 11/2010 | Dhuper et al. |
| 7,841,343 B2 | 11/2010 | Deane |
| 7,850,619 B2 | 12/2010 | Gavish et al. |
| 7,855,656 B2 | 12/2010 | Maschke |
| 7,855,716 B2 | 12/2010 | McCreary et al. |
| 7,859,401 B2 | 12/2010 | Falck et al. |
| 7,865,244 B2 | 1/2011 | Giftakis et al. |
| 7,866,317 B2 | 1/2011 | Muellinger et al. |
| 7,866,318 B2 | 1/2011 | Bassin |
| 7,871,394 B2 | 1/2011 | Halbert et al. |
| D632,796 S | 2/2011 | Ross et al. |
| D632,797 S | 2/2011 | Ross et al. |
| 7,881,780 B2 | 2/2011 | Flaherty |
| 7,883,480 B2 | 2/2011 | Dunlop |
| 7,885,828 B2 | 2/2011 | Glaser-Seidnitzer et al. |
| 7,886,231 B2 | 2/2011 | Hopermann et al. |
| 7,891,353 B2 | 2/2011 | Chalvignac |
| 7,891,354 B2 | 2/2011 | Farbarik |
| 7,893,560 B2 | 2/2011 | Carter |
| 7,895,527 B2 | 2/2011 | Zaleski et al. |
| 7,905,231 B2 | 3/2011 | Chalvignac |
| 7,909,033 B2 | 3/2011 | Faram |
| 7,912,537 B2 | 3/2011 | Lee et al. |
| 7,914,459 B2 | 3/2011 | Green |
| 7,918,226 B2 | 4/2011 | Acker |
| 7,927,286 B2 | 4/2011 | Ranucci |
| 7,931,601 B2 | 4/2011 | Ranucci |
| D638,852 S | 5/2011 | Skidmore et al. |
| 7,934,499 B2 | 5/2011 | Berthon-Jones |
| 7,934,500 B2 | 5/2011 | Madaus |
| 7,938,114 B2 | 5/2011 | Matthews et al. |
| 7,942,823 B2 | 5/2011 | Wright |
| 7,953,419 B2 | 5/2011 | Jost et al. |
| 7,956,719 B2 | 6/2011 | Anderson, Jr. et al. |
| 7,958,892 B2 | 6/2011 | Kwok et al. |
| 7,963,283 B2 | 6/2011 | Sinderby |
| 7,970,450 B2 | 6/2011 | Kroecker et al. |
| 7,970,475 B2 | 6/2011 | Tehrani et al. |
| 7,984,712 B2 | 7/2011 | Soliman et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 7,992,564 B2 | 8/2011 | Doshi et al. |
| 7,997,271 B2 | 8/2011 | Hickle et al. |
| 8,001,967 B2 | 8/2011 | Wallace et al. |
| 8,002,711 B2 | 8/2011 | Wood et al. |
| D645,158 S | 9/2011 | Sanchez et al. |
| 8,015,974 B2 | 9/2011 | Christopher |
| 8,020,555 B2 | 9/2011 | Rapoport |
| 8,020,558 B2 | 9/2011 | Christopher |
| 8,021,308 B2 | 9/2011 | Carlson et al. |
| 8,021,309 B2 | 9/2011 | Zilberg |
| 8,021,310 B2 | 9/2011 | Sanborn et al. |
| 8,025,052 B2 | 9/2011 | Matthews |
| D649,157 S | 11/2011 | Skidmore et al. |
| 8,051,852 B2 | 11/2011 | Bassin |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,136,521 B2 | 3/2012 | Matthews |
| 8,157,743 B2 | 4/2012 | Schaetzl |
| 8,160,817 B2 | 4/2012 | Ranieri |
| 8,181,648 B2 | 5/2012 | Perine et al. |
| 8,186,344 B2 | 5/2012 | Bonassa |
| 8,210,173 B2 | 7/2012 | Vandine |
| 8,210,174 B2 | 7/2012 | Farbarik |
| 8,240,684 B2 | 8/2012 | Ross et al. |
| 8,261,742 B2 | 9/2012 | Strothmann |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,316,847 B2 | 11/2012 | Hallett |
| 8,353,844 B2 | 1/2013 | Jin |
| 8,381,729 B2 | 2/2013 | Freitag |
| 8,388,548 B2 | 3/2013 | Green |
| 8,397,720 B2 | 3/2013 | Eger |
| 8,408,205 B2 | 4/2013 | Madaus |
| 8,424,524 B2 | 4/2013 | Heinonen |
| 8,443,801 B2 | 5/2013 | Soliman |
| 8,457,706 B2 | 6/2013 | Baker, Jr. |
| 8,485,982 B2 | 7/2013 | Gavish |
| 8,528,553 B2 | 9/2013 | Wysocki |
| D692,556 S | 10/2013 | Winter |
| 8,555,880 B2 | 10/2013 | Boring |
| D693,001 S | 11/2013 | Winter |
| 8,573,205 B2 | 11/2013 | Habashi |
| 8,573,207 B2 | 11/2013 | Gutierrez |
| 8,603,006 B2 | 12/2013 | Mulqueeny |
| 8,617,083 B2 | 12/2013 | Euliano |
| 8,646,447 B2 | 2/2014 | Martin |
| 8,652,065 B2 | 2/2014 | Titchener |
| D701,601 S | 3/2014 | Winter |
| 8,672,858 B2 | 3/2014 | Euliano |
| 8,695,597 B2 | 4/2014 | Glaw |
| 8,707,953 B2 | 4/2014 | Wickham |
| 8,792,949 B2 | 7/2014 | Baker, Jr. |
| 8,826,906 B2 | 9/2014 | Bassin |
| 8,869,795 B2 | 10/2014 | Bassin |
| 8,893,717 B2 | 11/2014 | Montgomery |
| 8,899,231 B2 | 12/2014 | Bassin |
| 8,899,232 B2 | 12/2014 | Farrugia |
| 8,910,632 B2 | 12/2014 | Tiedje |
| 8,920,333 B2 | 12/2014 | Younes |
| 8,925,545 B2 | 1/2015 | Wondka |
| 8,985,107 B2 | 3/2015 | Viertiö-Oja |
| 8,985,109 B2 | 3/2015 | Bateman |
| 9,016,277 B2 | 4/2015 | Kniewasser |
| D731,048 S | 6/2015 | Winter |
| D731,049 S | 6/2015 | Winter |
| D731,065 S | 6/2015 | Winter |
| 9,078,984 B2 | 7/2015 | Poon |
| D736,905 S | 8/2015 | Winter |
| 9,114,222 B2 | 8/2015 | Bliss |
| D744,095 S | 11/2015 | Winter |
| 9,192,323 B2 | 11/2015 | Heyer |
| 9,216,262 B2 | 12/2015 | Desforges |
| 9,220,856 B2 | 12/2015 | Martin |
| 9,238,114 B2 | 1/2016 | Eger |
| 9,259,544 B2 | 2/2016 | Kane |
| 9,272,106 B2 | 3/2016 | Sibenaller |
| 9,295,797 B2 | 3/2016 | Shissler |
| 9,320,863 B2 | 4/2016 | Balko |
| 9,333,312 B2 | 5/2016 | Cardelius |
| 9,392,963 B2 | 7/2016 | Krans |
| 9,392,964 B2 | 7/2016 | Mulqueeny |
| 9,504,795 B2 | 11/2016 | Bassin |
| 9,555,204 B2 | 1/2017 | Rahlf |
| 9,592,356 B2 | 3/2017 | Truschel |
| 9,597,467 B2 | 3/2017 | Zheng |
| 9,636,474 B2 | 5/2017 | Mulqueeny |
| 9,682,208 B2 | 6/2017 | Ramanan |
| 9,713,690 B2 | 7/2017 | Somaiya |
| 9,827,387 B2 | 11/2017 | Schneider |
| 9,839,760 B2 | 12/2017 | Bonassa |
| 9,848,831 B2 | 12/2017 | Nonaka |
| 9,950,129 B2 | 4/2018 | Glenn |
| 9,968,750 B2 | 5/2018 | Sinderby |
| 9,987,444 B2 | 6/2018 | Colbaugh |
| 9,987,445 B2 | 6/2018 | Ahmad |
| 10,004,862 B2 | 6/2018 | Armitstead |
| 10,022,084 B2 | 7/2018 | Nonaka |
| 10,022,512 B2 | 7/2018 | Tiedje |
| 10,065,007 B2 | 9/2018 | Troili |
| 10,137,266 B2 | 11/2018 | Shelly |
| 10,165,966 B2 | 1/2019 | Banner |
| 10,179,218 B2 | 1/2019 | Ahmad |
| 10,293,126 B2 | 5/2019 | Berry |

(56) References Cited

U.S. PATENT DOCUMENTS

| | | |
|---|---|---|
| 10,342,457 B2 | 7/2019 | Spencer |
| 10,357,624 B2 | 7/2019 | Van Der Staay |
| 2001/0004893 A1 | 6/2001 | Biondi et al. |
| 2001/0007255 A1 | 7/2001 | Stumpf |
| 2001/0035186 A1 | 11/2001 | Hill |
| 2001/0056358 A1 | 12/2001 | Dulong et al. |
| 2002/0017301 A1 | 2/2002 | Lundin |
| 2002/0023640 A1 | 2/2002 | Nightengale |
| 2002/0026941 A1 | 3/2002 | Biondi et al. |
| 2002/0042564 A1 | 4/2002 | Cooper et al. |
| 2002/0042565 A1 | 4/2002 | Cooper et al. |
| 2002/0044059 A1 | 4/2002 | Reeder et al. |
| 2002/0046753 A1 | 4/2002 | Lamb |
| 2002/0073993 A1 | 6/2002 | Weinstein et al. |
| 2002/0077863 A1 | 6/2002 | Rutledge et al. |
| 2002/0091548 A1 | 7/2002 | Auer et al. |
| 2002/0153006 A1 | 10/2002 | Zimlich et al. |
| 2002/0153009 A1 | 10/2002 | Chornyj et al. |
| 2002/0174866 A1 | 11/2002 | Orr et al. |
| 2002/0177758 A1 | 11/2002 | Schoenberg et al. |
| 2002/0185126 A1 | 12/2002 | Krebs |
| 2002/0195105 A1 | 12/2002 | Blue et al. |
| 2003/0010339 A1 | 1/2003 | Banner et al. |
| 2003/0034031 A1 | 2/2003 | Lev et al. |
| 2003/0037786 A1 | 2/2003 | Biondi et al. |
| 2003/0050568 A1 | 3/2003 | Green et al. |
| 2003/0060723 A1 | 3/2003 | Joo et al. |
| 2003/0062045 A1 | 4/2003 | Woodring et al. |
| 2003/0106553 A1 | 6/2003 | Vanderveen |
| 2003/0125662 A1 | 7/2003 | Bui |
| 2003/0130567 A1 | 7/2003 | Mault et al. |
| 2003/0130595 A1 | 7/2003 | Mault |
| 2003/0131848 A1 | 7/2003 | Stenzler |
| 2003/0136402 A1 | 7/2003 | Jiang et al. |
| 2003/0140925 A1 | 7/2003 | Sapienza et al. |
| 2003/0140928 A1 | 7/2003 | Bui et al. |
| 2003/0140929 A1 | 7/2003 | Wilkes et al. |
| 2003/0141368 A1 | 7/2003 | Pascual et al. |
| 2003/0141981 A1 | 7/2003 | Bui et al. |
| 2003/0144878 A1 | 7/2003 | Wilkes et al. |
| 2003/0144880 A1 | 7/2003 | Talachian et al. |
| 2003/0144881 A1 | 7/2003 | Talachian et al. |
| 2003/0144882 A1 | 7/2003 | Talachian et al. |
| 2003/0145853 A1 | 8/2003 | Muellner |
| 2003/0154979 A1 | 8/2003 | Berthon Jones |
| 2003/0159695 A1 | 8/2003 | Younes |
| 2003/0172929 A1 | 9/2003 | Muellner |
| 2003/0176804 A1 | 9/2003 | Melker |
| 2003/0178024 A1 | 9/2003 | Allan et al. |
| 2003/0192542 A1 | 10/2003 | Isaza |
| 2003/0192544 A1 | 10/2003 | Berthon Jones et al. |
| 2003/0201697 A1 | 10/2003 | Richardson |
| 2003/0204414 A1 | 10/2003 | Wilkes et al. |
| 2003/0204416 A1 | 10/2003 | Radpay et al. |
| 2003/0204419 A1 | 10/2003 | Wilkes et al. |
| 2003/0204420 A1 | 10/2003 | Wilkes et al. |
| 2003/0208152 A1 | 11/2003 | Avrahami et al. |
| 2003/0208465 A1 | 11/2003 | Yurko et al. |
| 2003/0222548 A1 | 12/2003 | Richardson et al. |
| 2003/0225339 A1 | 12/2003 | Orr et al. |
| 2003/0230308 A1 | 12/2003 | Linden |
| 2004/0003814 A1 | 1/2004 | Banner et al. |
| 2004/0010425 A1 | 1/2004 | Wilkes et al. |
| 2004/0016431 A1 | 1/2004 | Preveyraud |
| 2004/0034289 A1 | 2/2004 | Teller et al. |
| 2004/0040560 A1 | 3/2004 | Euliano et al. |
| 2004/0050387 A1 | 3/2004 | Younes |
| 2004/0059604 A1 | 3/2004 | Zaleski |
| 2004/0073453 A1 | 4/2004 | Nenov et al. |
| 2004/0078231 A1 | 4/2004 | Wilkes et al. |
| 2004/0103896 A1 | 6/2004 | Jafari et al. |
| 2004/0121767 A1 | 6/2004 | Simpson et al. |
| 2004/0122294 A1 | 6/2004 | Hatlestad et al. |
| 2004/0149282 A1 | 8/2004 | Hickle |
| 2004/0150525 A1 | 8/2004 | Wilson et al. |
| 2004/0159323 A1 | 8/2004 | Schmidt et al. |
| 2004/0167465 A1 | 8/2004 | Mihai et al. |
| 2004/0167804 A1 | 8/2004 | Simpson et al. |
| 2004/0172222 A1 | 9/2004 | Simpson et al. |
| 2004/0172300 A1 | 9/2004 | Mihai et al. |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0187864 A1 | 9/2004 | Adams |
| 2004/0194779 A1 | 10/2004 | Doshi |
| 2004/0194780 A1 | 10/2004 | Doshi |
| 2004/0200477 A1 | 10/2004 | Bleys et al. |
| 2004/0206355 A1 | 10/2004 | Berthon Jones et al. |
| 2004/0221847 A1 | 11/2004 | Berthon Jones et al. |
| 2004/0224293 A1 | 11/2004 | Penning et al. |
| 2004/0231670 A1 | 11/2004 | Bassin |
| 2004/0236240 A1 | 11/2004 | Kraus et al. |
| 2004/0244804 A1 | 12/2004 | Olsen et al. |
| 2004/0249673 A1 | 12/2004 | Smith |
| 2005/0016534 A1 | 1/2005 | Ost |
| 2005/0022809 A1 | 2/2005 | Wondka |
| 2005/0027252 A1 | 2/2005 | Boukas |
| 2005/0033198 A1 | 2/2005 | Kehyayan et al. |
| 2005/0039748 A1 | 2/2005 | Andrieux |
| 2005/0054910 A1 | 3/2005 | Tremblay et al. |
| 2005/0055242 A1 | 3/2005 | Bello et al. |
| 2005/0055244 A1 | 3/2005 | Mullan et al. |
| 2005/0061318 A1 | 3/2005 | Faram |
| 2005/0065817 A1 | 3/2005 | Mihai et al. |
| 2005/0075542 A1 | 4/2005 | Goldreich |
| 2005/0075904 A1 | 4/2005 | Wager et al. |
| 2005/0076907 A1 | 4/2005 | Stenzler |
| 2005/0085865 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0098179 A1 | 5/2005 | Burton et al. |
| 2005/0103331 A1 | 5/2005 | Wedemeyer |
| 2005/0108057 A1 | 5/2005 | Cohen et al. |
| 2005/0109339 A1 | 5/2005 | Stahmann et al. |
| 2005/0109340 A1 | 5/2005 | Tehrani |
| 2005/0112013 A1 | 5/2005 | DeVries et al. |
| 2005/0112325 A1 | 5/2005 | Hickle |
| 2005/0121035 A1 | 6/2005 | Martin |
| 2005/0124866 A1 | 6/2005 | Elaz et al. |
| 2005/0126565 A1 | 6/2005 | Huang |
| 2005/0133027 A1 | 6/2005 | Elaz et al. |
| 2005/0133028 A1 | 6/2005 | Pagan |
| 2005/0137480 A1 | 6/2005 | Alt et al. |
| 2005/0139212 A1 | 6/2005 | Bourdon |
| 2005/0139213 A1 | 6/2005 | Blike |
| 2005/0143632 A1 | 6/2005 | Elaz et al. |
| 2005/0143672 A1 | 6/2005 | Green et al. |
| 2005/0156933 A1 | 7/2005 | Lee et al. |
| 2005/0171876 A1 | 8/2005 | Golden |
| 2005/0177096 A1 | 8/2005 | Bollish et al. |
| 2005/0188083 A1 | 8/2005 | Biondi et al. |
| 2005/0192488 A1 | 9/2005 | Bryenton et al. |
| 2005/0199237 A1 | 9/2005 | Lurie |
| 2005/0204310 A1 | 9/2005 | De Zwart et al. |
| 2005/0215904 A1 | 9/2005 | Sumaneewera et al. |
| 2005/0217671 A1 | 10/2005 | Fisher et al. |
| 2005/0217674 A1 | 10/2005 | Burton et al. |
| 2005/0241639 A1 | 11/2005 | Zilberg |
| 2005/0251040 A1 | 11/2005 | Relkuntwar et al. |
| 2005/0263152 A1 | 12/2005 | Fong |
| 2005/0279358 A1 | 12/2005 | Richey, II |
| 2005/0284469 A1 | 12/2005 | Tobia et al. |
| 2005/0288571 A1 | 12/2005 | Perkins et al. |
| 2006/0009708 A1 | 1/2006 | Rapoport et al. |
| 2006/0011195 A1 | 1/2006 | Zarychta |
| 2006/0021618 A1 | 2/2006 | Berthon-Jones et al. |
| 2006/0032497 A1 | 2/2006 | Doshi |
| 2006/0037614 A1 | 2/2006 | Madaus et al. |
| 2006/0047202 A1 | 3/2006 | Elliott |
| 2006/0060198 A1 | 3/2006 | Aylsworth et al. |
| 2006/0078867 A1 | 4/2006 | Penny et al. |
| 2006/0079799 A1 | 4/2006 | Green et al. |
| 2006/0080140 A1 | 4/2006 | Buttner et al. |

(56) References Cited

U.S. PATENT DOCUMENTS

| | | |
|---|---|---|
| 2006/0080343 A1 | 4/2006 | Carter et al. |
| 2006/0094972 A1 | 5/2006 | Drew |
| 2006/0102171 A1 | 5/2006 | Gavish |
| 2006/0102180 A1 | 5/2006 | Berthon Jones |
| 2006/0122474 A1 | 6/2006 | Teller et al. |
| 2006/0122662 A1 | 6/2006 | Tehrani et al. |
| 2006/0129055 A1 | 6/2006 | Orr et al. |
| 2006/0142815 A1 | 6/2006 | Tehrani et al. |
| 2006/0144396 A1 | 7/2006 | DeVries et al. |
| 2006/0144397 A1 | 7/2006 | Wallace et al. |
| 2006/0149144 A1 | 7/2006 | Lynn et al. |
| 2006/0149589 A1 | 7/2006 | Wager |
| 2006/0150974 A1 | 7/2006 | Berthon-Jones |
| 2006/0150982 A1 | 7/2006 | Wood |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0162727 A1 | 7/2006 | Biondi et al. |
| 2006/0173257 A1 | 8/2006 | Nagai et al. |
| 2006/0174884 A1 | 8/2006 | Habashi |
| 2006/0178245 A1 | 8/2006 | Schiller et al. |
| 2006/0178591 A1 | 8/2006 | Hempfling |
| 2006/0178911 A1 | 8/2006 | Syed et al. |
| 2006/0189880 A1 | 8/2006 | Lynn et al. |
| 2006/0189900 A1 | 8/2006 | Flaherty |
| 2006/0195041 A1 | 8/2006 | Lynn et al. |
| 2006/0196507 A1 | 9/2006 | Bradley |
| 2006/0196508 A1 | 9/2006 | Chalvignac |
| 2006/0200009 A1 | 9/2006 | Wekell et al. |
| 2006/0201507 A1 | 9/2006 | Breen |
| 2006/0213518 A1 | 9/2006 | DeVries et al. |
| 2006/0229822 A1 | 10/2006 | Theobald et al. |
| 2006/0235324 A1 | 10/2006 | Lynn |
| 2006/0237015 A1 | 10/2006 | Berthon-Jones et al. |
| 2006/0241708 A1 | 10/2006 | Boute |
| 2006/0243275 A1 | 11/2006 | Ruckdeschel et al. |
| 2006/0249148 A1 | 11/2006 | Younes |
| 2006/0249151 A1 | 11/2006 | Gambone |
| 2006/0249153 A1 | 11/2006 | DeVries et al. |
| 2006/0249155 A1 | 11/2006 | Gambone |
| 2006/0264762 A1 | 11/2006 | Starr |
| 2006/0272642 A1 | 12/2006 | Chalvignac |
| 2006/0272643 A1 | 12/2006 | Aylsworth et al. |
| 2006/0276718 A1 | 12/2006 | Madaus et al. |
| 2006/0278221 A1 | 12/2006 | Schermeier et al. |
| 2006/0278222 A1 | 12/2006 | Schermeier et al. |
| 2006/0278224 A1 | 12/2006 | Shaffer et al. |
| 2006/0283450 A1 | 12/2006 | Shissler et al. |
| 2006/0283451 A1 | 12/2006 | Albertelli |
| 2006/0293609 A1 | 12/2006 | Stahmann et al. |
| 2006/0294464 A1 | 12/2006 | Tokimoto et al. |
| 2007/0000490 A1 | 1/2007 | DeVries et al. |
| 2007/0000494 A1 | 1/2007 | Banner et al. |
| 2007/0016441 A1 | 1/2007 | Stroup |
| 2007/0017510 A1 | 1/2007 | Riedo |
| 2007/0017515 A1 | 1/2007 | Wallace et al. |
| 2007/0017518 A1 | 1/2007 | Farrugia et al. |
| 2007/0021673 A1 | 1/2007 | Arbel et al. |
| 2007/0028920 A1 | 2/2007 | Acker |
| 2007/0028921 A1 | 2/2007 | Banner et al. |
| 2007/0038081 A1 | 2/2007 | Eck et al. |
| 2007/0044796 A1 | 3/2007 | Zdrojkowski et al. |
| 2007/0044805 A1 | 3/2007 | Wedler et al. |
| 2007/0060812 A1 | 3/2007 | Harel et al. |
| 2007/0062529 A1 | 3/2007 | Choncholas et al. |
| 2007/0062530 A1 | 3/2007 | Weismann et al. |
| 2007/0062532 A1 | 3/2007 | Choncholas |
| 2007/0062533 A1 | 3/2007 | Choncholas et al. |
| 2007/0066961 A1 | 3/2007 | Rutter |
| 2007/0068528 A1 | 3/2007 | Bohm et al. |
| 2007/0073169 A1 | 3/2007 | Averina et al. |
| 2007/0073181 A1 | 3/2007 | Pu et al. |
| 2007/0077200 A1 | 4/2007 | Baker |
| 2007/0089738 A1 | 4/2007 | Soliman et al. |
| 2007/0113843 A1 | 5/2007 | Hughes |
| 2007/0113849 A1 | 5/2007 | Matthews et al. |
| 2007/0119453 A1 | 5/2007 | Lu et al. |
| 2007/0123758 A1 | 5/2007 | Miesel et al. |
| 2007/0123792 A1 | 5/2007 | Kline |
| 2007/0129646 A1 | 6/2007 | Heinonen et al. |
| 2007/0129647 A1 | 6/2007 | Lynn |
| 2007/0144521 A1 | 6/2007 | DeVries et al. |
| 2007/0144523 A1 | 6/2007 | Bolam et al. |
| 2007/0149860 A1 | 6/2007 | Lynn et al. |
| 2007/0151563 A1 | 7/2007 | Ozaki et al. |
| 2007/0156060 A1 | 7/2007 | Cervantes |
| 2007/0156456 A1 | 7/2007 | McGillin et al. |
| 2007/0157931 A1 | 7/2007 | Parker et al. |
| 2007/0163589 A1 | 7/2007 | DeVries et al. |
| 2007/0163590 A1 | 7/2007 | Bassin |
| 2007/0167853 A1 | 7/2007 | Melker et al. |
| 2007/0179357 A1 | 8/2007 | Bardy |
| 2007/0181122 A1 | 8/2007 | Mulier |
| 2007/0185390 A1 | 8/2007 | Perkins et al. |
| 2007/0186928 A1 | 8/2007 | Be'Eri |
| 2007/0191697 A1 | 8/2007 | Lynn et al. |
| 2007/0191787 A1 | 8/2007 | Lim et al. |
| 2007/0193579 A1 | 8/2007 | Duquette et al. |
| 2007/0199566 A1 | 8/2007 | Be'eri |
| 2007/0203448 A1 | 8/2007 | Melker et al. |
| 2007/0208267 A1 | 9/2007 | Schmid et al. |
| 2007/0208438 A1 | 9/2007 | El-Mankabady et al. |
| 2007/0215155 A1 | 9/2007 | Marx et al. |
| 2007/0221222 A1 | 9/2007 | Lurie |
| 2007/0225574 A1 | 9/2007 | Ueda |
| 2007/0225623 A1 | 9/2007 | Freeman |
| 2007/0227537 A1 | 10/2007 | Bemister et al. |
| 2007/0227538 A1 | 10/2007 | Scholler et al. |
| 2007/0227539 A1 | 10/2007 | Schwaibold et al. |
| 2007/0232951 A1 | 10/2007 | Euliano et al. |
| 2007/0241884 A1 | 10/2007 | Yamazaki et al. |
| 2007/0265510 A1 | 11/2007 | Bardy |
| 2007/0265877 A1 | 11/2007 | Rice et al. |
| 2007/0267015 A1 | 11/2007 | Thoemmes et al. |
| 2007/0271122 A1 | 11/2007 | Zaleski |
| 2007/0272241 A1 | 11/2007 | Sanborn et al. |
| 2007/0272242 A1 | 11/2007 | Sanborn et al. |
| 2007/0272243 A1 | 11/2007 | Sherman et al. |
| 2007/0273216 A1 | 11/2007 | Farbarik |
| 2007/0276439 A1 | 11/2007 | Miesel et al. |
| 2007/0277825 A1 | 12/2007 | Bordewick et al. |
| 2007/0284361 A1 | 12/2007 | Nadjafizadeh et al. |
| 2007/0293741 A1 | 12/2007 | Bardy |
| 2008/0000471 A1 | 1/2008 | Bolam et al. |
| 2008/0000475 A1 | 1/2008 | Hill |
| 2008/0000477 A1 | 1/2008 | Huster et al. |
| 2008/0000478 A1 | 1/2008 | Matthiessen et al. |
| 2008/0000479 A1 | 1/2008 | Elaz et al. |
| 2008/0011294 A1 | 1/2008 | Heesch et al. |
| 2008/0011301 A1 | 1/2008 | Qian |
| 2008/0017189 A1 | 1/2008 | Ruckdeschel et al. |
| 2008/0017198 A1 | 1/2008 | Ivri |
| 2008/0029096 A1 | 2/2008 | Kollmeyer et al. |
| 2008/0029097 A1 | 2/2008 | Schatzl |
| 2008/0033304 A1 | 2/2008 | Dalai et al. |
| 2008/0033661 A1 | 2/2008 | Syroid et al. |
| 2008/0035145 A1 | 2/2008 | Adams et al. |
| 2008/0035146 A1 | 2/2008 | Crabb |
| 2008/0039735 A1 | 2/2008 | Hickerson |
| 2008/0041380 A1 | 2/2008 | Wallace et al. |
| 2008/0041382 A1 | 2/2008 | Matthews et al. |
| 2008/0041383 A1 | 2/2008 | Matthews et al. |
| 2008/0045844 A1 | 2/2008 | Arbel et al. |
| 2008/0047554 A1 | 2/2008 | Roy et al. |
| 2008/0053438 A1 | 3/2008 | DeVries et al. |
| 2008/0053441 A1 | 3/2008 | Gottlib et al. |
| 2008/0060656 A1 | 3/2008 | Isaza |
| 2008/0064963 A1 | 3/2008 | Schwaibold et al. |
| 2008/0065420 A1 | 3/2008 | Tirinato et al. |
| 2008/0066753 A1 | 3/2008 | Martin et al. |
| 2008/0072896 A1 | 3/2008 | Setzer et al. |
| 2008/0072900 A1 | 3/2008 | Kenyon et al. |
| 2008/0072901 A1 | 3/2008 | Habashi |
| 2008/0072902 A1 | 3/2008 | Setzer et al. |

(56) References Cited

U.S. PATENT DOCUMENTS

| | | |
|---|---|---|
| 2008/0076970 A1 | 3/2008 | Foulis et al. |
| 2008/0077033 A1 | 3/2008 | Figueiredo et al. |
| 2008/0077038 A1 | 3/2008 | McDonough et al. |
| 2008/0078390 A1 | 4/2008 | Milne et al. |
| 2008/0083644 A1 | 4/2008 | Janbakhsh et al. |
| 2008/0091117 A1 | 4/2008 | Choncholas et al. |
| 2008/0092043 A1 | 4/2008 | Trethewey |
| 2008/0092894 A1 | 4/2008 | Nicolazzi et al. |
| 2008/0097234 A1 | 4/2008 | Nicolazzi et al. |
| 2008/0103368 A1 | 5/2008 | Craine et al. |
| 2008/0110460 A1 | 5/2008 | Elaz et al. |
| 2008/0110461 A1 | 5/2008 | Mulqueeny et al. |
| 2008/0110462 A1 | 5/2008 | Chekal et al. |
| 2008/0115786 A1 | 5/2008 | Sinderby et al. |
| 2008/0125828 A1 | 5/2008 | Ignagni et al. |
| 2008/0125873 A1 | 5/2008 | Payne et al. |
| 2008/0135044 A1 | 6/2008 | Freitag et al. |
| 2008/0139956 A1 | 6/2008 | Diong |
| 2008/0142019 A1 | 6/2008 | Lewis et al. |
| 2008/0156330 A1 | 7/2008 | Smith et al. |
| 2008/0161653 A1 | 7/2008 | Lin et al. |
| 2008/0163872 A1 | 7/2008 | Negele et al. |
| 2008/0168990 A1 | 7/2008 | Cooke et al. |
| 2008/0178880 A1 | 7/2008 | Christopher et al. |
| 2008/0178882 A1 | 7/2008 | Christopher et al. |
| 2008/0183057 A1 | 7/2008 | Taube |
| 2008/0183095 A1 | 7/2008 | Austin et al. |
| 2008/0183239 A1 | 7/2008 | Tehrani et al. |
| 2008/0183240 A1 | 7/2008 | Tehrani et al. |
| 2008/0185009 A1 | 8/2008 | Choncholas et al. |
| 2008/0188903 A1 | 8/2008 | Tehrani et al. |
| 2008/0202525 A1 | 8/2008 | Mitton et al. |
| 2008/0208012 A1 | 8/2008 | Ali |
| 2008/0208281 A1 | 8/2008 | Tehrani et al. |
| 2008/0214947 A1 | 9/2008 | Hunt et al. |
| 2008/0216833 A1 | 9/2008 | Pujol et al. |
| 2008/0216835 A1 | 9/2008 | McGinnis et al. |
| 2008/0230057 A1 | 9/2008 | Sutherland |
| 2008/0230065 A1 | 9/2008 | Heinonen |
| 2008/0236582 A1 | 10/2008 | Tehrani |
| 2008/0236585 A1 | 10/2008 | Parker et al. |
| 2008/0243016 A1 | 10/2008 | Liao et al. |
| 2008/0251070 A1 | 10/2008 | Pinskiy et al. |
| 2008/0251078 A1 | 10/2008 | Buckley et al. |
| 2008/0255880 A1 | 10/2008 | Beller et al. |
| 2008/0257337 A1 | 10/2008 | Denyer et al. |
| 2008/0270912 A1 | 10/2008 | Booth |
| 2008/0275513 A1 | 11/2008 | Lattner et al. |
| 2008/0276939 A1 | 11/2008 | Tiedje |
| 2008/0276940 A1 | 11/2008 | Fuhrman et al. |
| 2008/0281219 A1 | 11/2008 | Glickman et al. |
| 2008/0283060 A1 | 11/2008 | Bassin |
| 2008/0283061 A1 | 11/2008 | Tiedje |
| 2008/0293025 A1 | 11/2008 | Zamierowsi et al. |
| 2008/0294060 A1 | 11/2008 | Haro et al. |
| 2008/0295830 A1 | 12/2008 | Martonen et al. |
| 2008/0295837 A1 | 12/2008 | McCormick et al. |
| 2008/0295839 A1 | 12/2008 | Habashi |
| 2008/0295840 A1 | 12/2008 | Glaw |
| 2008/0306351 A1 | 12/2008 | Izumi |
| 2008/0308105 A1 | 12/2008 | Alder et al. |
| 2008/0308109 A1 | 12/2008 | Brain |
| 2008/0312954 A1 | 12/2008 | Ullrich et al. |
| 2008/0314385 A1 | 12/2008 | Brunner et al. |
| 2008/0319513 A1 | 12/2008 | Pu et al. |
| 2009/0005651 A1 | 1/2009 | Ward et al. |
| 2009/0007909 A1 | 1/2009 | Carrico |
| 2009/0007914 A1 | 1/2009 | Bateman |
| 2009/0013999 A1 | 1/2009 | Bassin |
| 2009/0038617 A1 | 2/2009 | Berthon-Jones et al. |
| 2009/0038921 A1 | 2/2009 | Kaps et al. |
| 2009/0054743 A1 | 2/2009 | Stewart |
| 2009/0056709 A1 | 3/2009 | Worsoff |
| 2009/0062725 A1 | 3/2009 | Goebel |
| 2009/0063181 A1 | 3/2009 | Nho et al. |
| 2009/0065004 A1 | 3/2009 | Childers et al. |
| 2009/0076342 A1 | 3/2009 | Amurthur et al. |
| 2009/0078258 A1 | 3/2009 | Bowman et al. |
| 2009/0095297 A1 | 4/2009 | Hallett |
| 2009/0107502 A1 | 4/2009 | Younes |
| 2009/0114223 A1 | 5/2009 | Bonassa |
| 2009/0120439 A1 | 5/2009 | Goebel |
| 2009/0124917 A1 | 5/2009 | Hatlestad et al. |
| 2009/0125333 A1 | 5/2009 | Heywood et al. |
| 2009/0126734 A1 | 5/2009 | Dunsmore et al. |
| 2009/0131758 A1 | 5/2009 | Heywood et al. |
| 2009/0133701 A1 | 5/2009 | Brain |
| 2009/0137919 A1 | 5/2009 | Bar-Lavie et al. |
| 2009/0139522 A1 | 6/2009 | Thomson et al. |
| 2009/0143694 A1 | 6/2009 | Krauss et al. |
| 2009/0145438 A1 | 6/2009 | Brain |
| 2009/0149200 A1 | 6/2009 | Jayasinghe et al. |
| 2009/0149723 A1 | 6/2009 | Krauss et al. |
| 2009/0149927 A1 | 6/2009 | Kneuer et al. |
| 2009/0150184 A1 | 6/2009 | Spahn |
| 2009/0165795 A1 | 7/2009 | Nadjafizadeh et al. |
| 2009/0171167 A1 | 7/2009 | Baker, Jr. |
| 2009/0171176 A1 | 7/2009 | Andersohn |
| 2009/0188502 A1 | 7/2009 | Tiedje |
| 2009/0192421 A1 | 7/2009 | Huster et al. |
| 2009/0199855 A1 | 8/2009 | Davenport |
| 2009/0205660 A1 | 8/2009 | Thomson et al. |
| 2009/0205661 A1 | 8/2009 | Stephenson et al. |
| 2009/0205663 A1 | 8/2009 | Vandine et al. |
| 2009/0209828 A1 | 8/2009 | Musin |
| 2009/0209849 A1 | 8/2009 | Rowe et al. |
| 2009/0216145 A1 | 8/2009 | Skerl et al. |
| 2009/0221926 A1 | 9/2009 | Younes |
| 2009/0240523 A1 | 9/2009 | Friedlander et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0244003 A1 | 10/2009 | Bonnat |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0250054 A1 | 10/2009 | Loncar et al. |
| 2009/0259135 A1 | 10/2009 | Stasz |
| 2009/0266360 A1 | 10/2009 | Acker et al. |
| 2009/0277448 A1 | 11/2009 | Ahlmén et al. |
| 2009/0301486 A1 | 12/2009 | Masic |
| 2009/0301487 A1 | 12/2009 | Masic |
| 2009/0301488 A1 | 12/2009 | Sun |
| 2009/0301490 A1 | 12/2009 | Masic |
| 2009/0301491 A1 | 12/2009 | Masic et al. |
| 2009/0308393 A1 | 12/2009 | Luceros |
| 2009/0308394 A1 | 12/2009 | Levi |
| 2010/0004517 A1 | 1/2010 | Bryenton et al. |
| 2010/0008466 A1 | 1/2010 | Balakin |
| 2010/0011307 A1 | 1/2010 | Desfossez et al. |
| 2010/0022904 A1 | 1/2010 | Centen |
| 2010/0024820 A1 | 2/2010 | Bourdon |
| 2010/0030092 A1 | 2/2010 | Kristensen et al. |
| 2010/0048985 A1 | 2/2010 | Henke et al. |
| 2010/0048986 A1 | 2/2010 | Henke et al. |
| 2010/0049034 A1 | 2/2010 | Eck et al. |
| 2010/0049264 A1 | 2/2010 | Henke et al. |
| 2010/0049265 A1 | 2/2010 | Henke et al. |
| 2010/0051026 A1 | 3/2010 | Graboi |
| 2010/0051029 A1 | 3/2010 | Jafari et al. |
| 2010/0056852 A1 | 3/2010 | Henke et al. |
| 2010/0056853 A1 | 3/2010 | Henke et al. |
| 2010/0056855 A1 | 3/2010 | Henke et al. |
| 2010/0056929 A1 | 3/2010 | Stahmann et al. |
| 2010/0056941 A1 | 3/2010 | Henke et al. |
| 2010/0056942 A1 | 3/2010 | Henke et al. |
| 2010/0057148 A1 | 3/2010 | Henke et al. |
| 2010/0059061 A1 | 3/2010 | Brain |
| 2010/0063348 A1 | 3/2010 | Henke et al. |
| 2010/0063350 A1 | 3/2010 | Henke et al. |
| 2010/0063365 A1 | 3/2010 | Pisani et al. |

(56) References Cited

U.S. PATENT DOCUMENTS

| | | |
|---|---|---|
| 2010/0069761 A1 | 3/2010 | Karst et al. |
| 2010/0069774 A1 | 3/2010 | Bingham et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0072055 A1 | 3/2010 | Tanaka et al. |
| 2010/0076278 A1 | 3/2010 | van der Zande et al. |
| 2010/0076322 A1 | 3/2010 | Shrivastav et al. |
| 2010/0076323 A1 | 3/2010 | Shrivastav et al. |
| 2010/0078017 A1 | 4/2010 | Andrieux et al. |
| 2010/0078019 A1 | 4/2010 | Rittner et al. |
| 2010/0078026 A1 | 4/2010 | Andrieux et al. |
| 2010/0081119 A1 | 4/2010 | Jafari et al. |
| 2010/0081890 A1 | 4/2010 | Li et al. |
| 2010/0081955 A1 | 4/2010 | Wood, Jr. et al. |
| 2010/0083968 A1 | 4/2010 | Wondka et al. |
| 2010/0089396 A1 | 4/2010 | Richard et al. |
| 2010/0095961 A1 | 4/2010 | Tornesel et al. |
| 2010/0108066 A1 | 5/2010 | Martin et al. |
| 2010/0116270 A1 | 5/2010 | Edwards et al. |
| 2010/0125227 A1 | 5/2010 | Bird |
| 2010/0130873 A1 | 5/2010 | Yuen et al. |
| 2010/0139660 A1 | 6/2010 | Adahan |
| 2010/0145165 A1 | 6/2010 | Merry |
| 2010/0147303 A1 | 6/2010 | Jafari et al. |
| 2010/0160839 A1 | 6/2010 | Freeman et al. |
| 2010/0186744 A1 | 7/2010 | Andrieux |
| 2010/0198289 A1 | 8/2010 | Kameli et al. |
| 2010/0212675 A1 | 8/2010 | Walling et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0222693 A1 | 9/2010 | Eriksen et al. |
| 2010/0229863 A1 | 9/2010 | Enk |
| 2010/0236551 A1 | 9/2010 | Enk |
| 2010/0236555 A1 | 9/2010 | Jafari et al. |
| 2010/0242961 A1 | 9/2010 | Mougel et al. |
| 2010/0249549 A1 | 9/2010 | Baker, Jr. et al. |
| 2010/0249584 A1 | 9/2010 | Albertelli |
| 2010/0252046 A1 | 10/2010 | Dahlström et al. |
| 2010/0258124 A1 | 10/2010 | Madaus et al. |
| 2010/0262035 A1 | 10/2010 | Subramanian |
| 2010/0263669 A1 | 10/2010 | Bowsher |
| 2010/0274100 A1 | 10/2010 | Behar et al. |
| 2010/0275921 A1 | 11/2010 | Schindhelm et al. |
| 2010/0282251 A1 | 11/2010 | Calluaud et al. |
| 2010/0282259 A1 | 11/2010 | Figueiredo et al. |
| 2010/0288283 A1 | 11/2010 | Campbell et al. |
| 2010/0298718 A1 | 11/2010 | Gilham et al. |
| 2010/0300446 A1 | 12/2010 | Nicolazzi et al. |
| 2010/0312132 A1 | 12/2010 | Wood et al. |
| 2010/0317980 A1 | 12/2010 | Guglielmino |
| 2010/0324438 A1 | 12/2010 | Ni et al. |
| 2010/0331715 A1 | 12/2010 | Addison et al. |
| 2011/0004489 A1 | 1/2011 | Schoenberg et al. |
| 2011/0009746 A1 | 1/2011 | Tran et al. |
| 2011/0009763 A1 | 1/2011 | Levitsky et al. |
| 2011/0011400 A1 | 1/2011 | Gentner et al. |
| 2011/0011403 A1 | 1/2011 | Hannah et al. |
| 2011/0015493 A1 | 1/2011 | Koschek |
| 2011/0017214 A1 | 1/2011 | Tehrani |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0030686 A1 | 2/2011 | Wilkinson et al. |
| 2011/0041847 A1 | 2/2011 | Cosic |
| 2011/0041849 A1 | 2/2011 | Chen et al. |
| 2011/0041850 A1 | 2/2011 | Vandine et al. |
| 2011/0054289 A1 | 3/2011 | Derchak et al. |
| 2011/0067698 A1 | 3/2011 | Zheng et al. |
| 2011/0073112 A1 | 3/2011 | DiBlasi et al. |
| 2011/0092839 A1 | 4/2011 | Alshaer et al. |
| 2011/0092841 A1 | 4/2011 | Bassin |
| 2011/0100365 A1 | 5/2011 | Wedler et al. |
| 2011/0112424 A1 | 5/2011 | Kesselman et al. |
| 2011/0112425 A1 | 5/2011 | Muhlsteff et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132363 A1 | 6/2011 | Chalvignac |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0197884 A1 | 8/2011 | Duff et al. |
| 2011/0208082 A1 | 8/2011 | Madaus et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0226248 A1 | 9/2011 | Duff et al. |
| 2011/0230780 A1 | 9/2011 | Sanborn et al. |
| 2011/0249006 A1 | 10/2011 | Wallace et al. |
| 2011/0253136 A1* | 10/2011 | Sweeney .......... A61M 16/161 128/203.12 |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0265793 A1 | 11/2011 | Haveri |
| 2011/0271960 A1 | 11/2011 | Milne et al. |
| 2011/0273299 A1 | 11/2011 | Milne et al. |
| 2011/0288431 A1 | 11/2011 | Alshaer et al. |
| 2011/0313263 A1 | 12/2011 | Wood et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0016252 A1 | 1/2012 | Melker et al. |
| 2012/0029317 A1 | 2/2012 | Doyle et al. |
| 2012/0029362 A1 | 2/2012 | Patangay et al. |
| 2012/0030611 A1 | 2/2012 | Skidmore |
| 2012/0037159 A1* | 2/2012 | Mulqueeny .......... A61M 16/06 128/204.23 |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0101399 A1 | 4/2012 | Henderson |
| 2012/0123219 A1 | 5/2012 | Georgiev et al. |
| 2012/0133519 A1 | 5/2012 | Milne et al. |
| 2012/0136222 A1 | 5/2012 | Doyle et al. |
| 2012/0136270 A1 | 5/2012 | Leuthardt et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |

(56) References Cited

U.S. PATENT DOCUMENTS

| | | |
|---|---|---|
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0042869 A1 | 2/2013 | Andrieux et al. |
| 2013/0047983 A1 | 2/2013 | Andrieux et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0152923 A1 | 6/2013 | Andrieux et al. |
| 2013/0158370 A1 | 6/2013 | Doyle et al. |
| 2013/0159912 A1 | 6/2013 | Baker, Jr. |
| 2013/0167842 A1 | 7/2013 | Jafari et al. |
| 2013/0167843 A1 | 7/2013 | Kimm et al. |
| 2013/0186397 A1 | 7/2013 | Patel |
| 2013/0186400 A1 | 7/2013 | Jafari et al. |
| 2013/0186401 A1 | 7/2013 | Jafari et al. |
| 2013/0192599 A1 | 8/2013 | Nakai et al. |
| 2013/0220324 A1 | 8/2013 | Jafari et al. |
| 2013/0233314 A1 | 9/2013 | Jafari et al. |
| 2013/0233319 A1 | 9/2013 | Winter et al. |
| 2013/0239038 A1 | 9/2013 | Skidmore et al. |
| 2013/0239967 A1 | 9/2013 | Jafari et al. |
| 2013/0255682 A1 | 10/2013 | Jafari et al. |
| 2013/0255685 A1 | 10/2013 | Jafari et al. |
| 2013/0276788 A1 | 10/2013 | Masic |
| 2013/0283197 A1 | 10/2013 | Skidmore |
| 2013/0284172 A1 | 10/2013 | Doyle et al. |
| 2013/0284173 A1 | 10/2013 | Masic et al. |
| 2013/0284177 A1 | 10/2013 | Li et al. |
| 2013/0327331 A1 | 12/2013 | Bourdon |
| 2013/0333697 A1 | 12/2013 | Carter et al. |
| 2013/0333703 A1 | 12/2013 | Wallace et al. |
| 2013/0338514 A1 | 12/2013 | Karst et al. |
| 2013/0345532 A1 | 12/2013 | Doyle et al. |
| 2014/0000606 A1 | 1/2014 | Doyle et al. |
| 2014/0012150 A1* | 1/2014 | Milne ............... A61M 16/0051 600/529 |
| 2014/0034054 A1 | 2/2014 | Angelico et al. |
| 2014/0034056 A1 | 2/2014 | Leone et al. |
| 2014/0041656 A1 | 2/2014 | Jourdain et al. |
| 2014/0048071 A1 | 2/2014 | Milne et al. |
| 2014/0048072 A1 | 2/2014 | Angelico et al. |
| 2014/0121553 A1 | 5/2014 | Milne et al. |
| 2014/0123979 A1 | 5/2014 | Doyle et al. |
| 2014/0130798 A1 | 5/2014 | Milne et al. |
| 2014/0182590 A1 | 7/2014 | Platt et al. |
| 2014/0224250 A1 | 8/2014 | Sanchez et al. |
| 2014/0251328 A1 | 9/2014 | Graboi et al. |
| 2014/0261409 A1 | 9/2014 | Dong et al. |
| 2014/0261410 A1 | 9/2014 | Sanchez et al. |
| 2014/0261424 A1 | 9/2014 | Doyle et al. |
| 2014/0276176 A1 | 9/2014 | Winter |
| 2014/0283833 A1* | 9/2014 | Zheng ............... A61M 16/0003 128/204.22 |
| 2014/0290657 A1 | 10/2014 | Vandine et al. |
| 2014/0309507 A1 | 10/2014 | Baker, Jr. |
| 2014/0345616 A1 | 11/2014 | Masic |
| 2014/0360497 A1 | 12/2014 | Jafari et al. |
| 2014/0366879 A1 | 12/2014 | Kimm et al. |
| 2014/0373845 A1 | 12/2014 | Dong |
| 2015/0034082 A1 | 2/2015 | Kimm et al. |
| 2015/0034083 A1 | 2/2015 | Lellouche |
| 2015/0045687 A1 | 2/2015 | Nakai et al. |
| 2015/0090258 A1 | 4/2015 | Milne et al. |
| 2015/0090264 A1 | 4/2015 | Dong |
| 2015/0107584 A1 | 4/2015 | Jafari et al. |
| 2016/0045694 A1 | 2/2016 | Esmaeil-zadeh-azar |
| 2016/0199606 A1 | 7/2016 | Eger |
| 2018/0001042 A1* | 1/2018 | Albanese ............... G16H 50/50 |

FOREIGN PATENT DOCUMENTS

| | | |
|---|---|---|
| EP | 1005829 | 6/2000 |
| EP | 1005830 | 6/2000 |
| EP | 1103279 | 5/2001 |
| EP | 996358 | 1/2002 |
| EP | 1277435 | 1/2003 |
| EP | 1421966 | 5/2004 |
| EP | 1464357 | 10/2004 |
| GB | 2319967 | 6/1998 |
| WO | WO 9014852 | 12/1990 |
| WO | WO 9308534 | 4/1993 |
| WO | WO 9312823 | 7/1993 |
| WO | WO 9314696 | 8/1993 |
| WO | WO 9414374 | 7/1994 |
| WO | WO 9508471 | 3/1995 |
| WO | WO 9532480 | 11/1995 |
| WO | WO 9624285 | 8/1996 |
| WO | WO 9706844 | 2/1997 |
| WO | WO 9720592 | 6/1997 |
| WO | WO 9811840 | 3/1998 |
| WO | WO 9814116 | 4/1998 |
| WO | WO 9829790 | 7/1998 |
| WO | WO 9833554 | 8/1998 |
| WO | WO 9840014 | 9/1998 |
| WO | WO 9841267 | 9/1998 |
| WO | WO 9841269 | 9/1998 |
| WO | WO 9841270 | 9/1998 |
| WO | WO 9841271 | 9/1998 |
| WO | WO 9858219 | 12/1998 |
| WO | WO 9903524 | 1/1999 |
| WO | WO 9952431 | 10/1999 |
| WO | WO 9952437 | 10/1999 |
| WO | WO 9959460 | 11/1999 |
| WO | WO 9962403 | 12/1999 |
| WO | WO 0018293 | 4/2000 |
| WO | WO 0019886 | 4/2000 |
| WO | WO 0062664 | 10/2000 |
| WO | WO 0100264 | 1/2001 |
| WO | WO 0100265 | 1/2001 |
| WO | WO 0128416 | 4/2001 |
| WO | WO 0134022 | 5/2001 |
| WO | WO 0245566 | 6/2002 |
| WO | WO 02082967 | 10/2002 |
| WO | WO 03015005 | 2/2003 |
| WO | WO 03024317 | 3/2003 |
| WO | WO 03045493 | 6/2003 |
| WO | WO 03053503 | 7/2003 |
| WO | WO 03060650 | 7/2003 |
| WO | WO 03060651 | 7/2003 |
| WO | WO 03075989 | 9/2003 |
| WO | WO 03075990 | 9/2003 |
| WO | WO 03075991 | 9/2003 |
| WO | WO 03084405 | 10/2003 |
| WO | WO 04014216 | 2/2004 |
| WO | WO 04014226 | 2/2004 |
| WO | WO 04019766 | 3/2004 |
| WO | WO 04032719 | 4/2004 |
| WO | WO 04043254 | 5/2004 |
| WO | WO 2005010796 | 2/2005 |
| WO | WO 05024729 | 3/2005 |
| WO | WO 05055825 | 6/2005 |
| WO | WO 05056087 | 6/2005 |
| WO | WO 05069740 | 8/2005 |
| WO | WO 05077260 | 8/2005 |

(56) References Cited

FOREIGN PATENT DOCUMENTS

| | | |
|---|---|---|
| WO | WO 05112739 | 12/2005 |
| WO | WO 06008745 | 1/2006 |
| WO | WO 06009830 | 1/2006 |
| WO | WO 06037184 | 4/2006 |
| WO | WO 06050388 | 5/2006 |
| WO | WO 06051466 | 5/2006 |
| WO | WO 06078432 | 7/2006 |
| WO | WO 06079152 | 8/2006 |
| WO | WO 06094055 | 9/2006 |
| WO | WO 06096080 | 9/2006 |
| WO | WO 06109072 | 10/2006 |
| WO | WO 06123956 | 11/2006 |
| WO | WO 06125986 | 11/2006 |
| WO | WO 06125987 | 11/2006 |
| WO | WO 06125989 | 11/2006 |
| WO | WO 06125990 | 11/2006 |
| WO | WO 06137067 | 12/2006 |
| WO | WO 2007033050 | 3/2007 |
| WO | WO 2007106804 | 9/2007 |
| WO | WO 07145948 | 12/2007 |
| WO | WO 2008008659 | 1/2008 |
| WO | WO 2008021222 | 2/2008 |
| WO | WO 2008030091 | 3/2008 |
| WO | WO 2008042699 | 4/2008 |
| WO | WO 2008058997 | 5/2008 |
| WO | WO 2008062554 | 5/2008 |
| WO | WO 2008113410 | 9/2008 |
| WO | WO 2008113752 | 9/2008 |
| WO | WO 2008118951 | 10/2008 |
| WO | WO 2008140528 | 11/2008 |
| WO | WO 2008146264 | 12/2008 |
| WO | WO 2008148134 | 12/2008 |
| WO | WO 2009024967 | 2/2009 |
| WO | WO 2009027864 | 3/2009 |
| WO | WO 2009036334 | 3/2009 |
| WO | WO 2009060330 | 5/2009 |
| WO | WO 2009124297 | 10/2009 |
| WO | WO 2010009531 | 1/2010 |
| WO | WO 2010020980 | 2/2010 |
| WO | WO 2010021730 | 2/2010 |
| WO | WO 2010039989 | 4/2010 |
| WO | WO 2010126916 | 11/2010 |
| WO | WO 2010141415 | 12/2010 |
| WO | WO 2011005953 | 1/2011 |
| WO | WO 2011022242 | 2/2011 |

OTHER PUBLICATIONS

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Boitano, Louis J., "An Evaluation of Home Volume Ventilators That Support OpenCircuit Mouthpiece Ventilation", Respiratory Care, Nov. 2005, vol. 50, No. 11, pp. 1457-1461.

Colombo, Davide et al., "Efficacy of Ventilator Waveforms Observation in Detecting Patient-Ventilator Asychrony", Crit. Care Med., 2011, vol. 39, No. 11, pp. 1-6.

De Wit, M. et al., "Ineffective triggering predicts increased duration of mechanical ventilation", Covidien Clinical Summary of article in Crit Care Med. 2009; 37(10): 2740-2745, 2 pgs.

De Wit, Marjolein et al., "Ineffective triggering predicts increased duration of mechanical ventilation", Crit. Care Med., 2009 vol. 37, No. 10, pp. 2740-2745.

Heinrich, Rene et al., "Real-Time Computation of a Patient's Respiratory Effort During Ventilation", Journal of Clinical Monitoring and Computing (2006), 20: 193-200.

Malladi et al., "A Generalized Shiryayev Sequential Probability Ratio Test for Change Detection and Isolation", IEEE Trans. Auto Control, 1999, 44(8), pp. 1522-1534.

Nguyen, Quang-Thang, "Contributions to Statistical Signal Processing With Applications in Biomedical Engineering", Doctoral Thesis, L'Universite de Bretagne Occidentale, Apr. 26, 2013, 158 pages.

PCT International Search Report and Written Opinion in International Application PCT/US15/056717, dated Feb. 25, 2016, 18 pgs.

PCT International Search Report in Application PCT/US09/046409 dated Sep. 29, 2009, 5 pgs.

PCT Invitation to Pay Additional Fees and Partial Search Report in International Application PCT/US15/056717, dated Dec. 22, 2015, 9 pgs.

Ru et al., "Sequential Detection of Target Maneuvers", Proc. 2005 7th Int. Conf. on Info. Fusion, 2005, pp. 345-351.

U.S. Appl. No. 12/980,583, filed Dec. 19, 2010, entitled "Systems and Methods for Ventilation to Obtain a Predetermined Patient Effort", 48 pgs.

Puritan Bennett 980 Series Ventilator Operator's Manual, Covidien, Jan. 29, 2014, Part. No. 10077893 A Jan. 2014, 506 pages.

\* cited by examiner

VENTILATION TRIGGERING

CROSS-REFERENCE TO RELATED APPLICATIONS

This application is a divisional application and claims priority to U.S. patent application Ser. No. 14/524,881, now U.S. Pat. No. 9,950,129, filed Oct. 27, 2014, entitled "VENTILATION TRIGGERING," which application is incorporated herein by reference in its entirety.

INTRODUCTION

Medical ventilator systems have long been used to provide ventilatory and supplemental oxygen support to patients. These ventilators typically comprise a source of pressurized oxygen which is fluidly connected to the patient through a conduit or tubing. As each patient may require a different ventilation strategy, modern ventilators can be customized for the particular needs of an individual patient. For example, several different ventilator modes or settings have been created to provide better ventilation for patients in various different scenarios, such as mandatory ventilation modes, assist control ventilation modes, and spontaneous modes.

TRIGGERING

This disclosure describes novel triggering systems and methods that allow the patient to trigger or initiate the delivery of a breath during ventilation on a ventilator. Further, this disclosure describes systems and methods for triggering ventilation utilizing a statistical trigger mode. This disclosure also describes novel systems and methods for analyzing and/or displaying the ramifications of a potential change in a triggering threshold for a currently utilized breath type.

In part, this disclosure describes a method for ventilating a patient with a ventilator. The method includes:
monitoring a parameter signal during exhalation;
determining a stable portion of exhalation based at least on the parameter signal for a current computational cycle;
setting an initial probability for each of a null hypothesis and a trigger hypothesis based on a current exhalation time;
calculating a mean of the parameter signal based on a predetermined set of parameter signals for a most recent set of computational cycles;
updating a noise estimate based at least on the mean of the parameter signal;
calculating a residual for the null hypothesis and the trigger hypothesis based at least on the parameter signal for the current computational cycle;
calculating a first probability for the null hypothesis and calculating a second probability for the trigger hypothesis for the parameter signal for the current computational cycle based on the initial probability, the noise estimate, and the residual;
comparing the first probability and the second probability to a threshold; and
controlling ventilation delivered to the patient by the ventilator based on the comparison.

In part, this disclosure describes a method for ventilating a patient with a ventilator. The method includes:
monitoring a parameter signal during an exhalation;
determining a stable portion of exhalation based at least on the parameter signal for a current computational cycle;
calculating an initial predicted parameter signal of a next computational cycle and an initial covariance for the initial predicted parameter signal for the parameter signal for the current computational cycle;
calculating a post predicted parameter signal of the next computational cycle and a post covariance for the post predicted parameter signal for a first and second derivative of the parameter signal of the parameter signal for the current computational cycle;
determining that a run threshold has been met based on at least one of a current exhalation time, the initial covariance, and the post covariance;
updating a noise estimate based at least on a single value of the covariance utilized in calculating at least one of the initial covariance and the post covariance;
calculating a residual for each of a null hypothesis and a trigger hypothesis based at least on the parameter signal for the current computational cycle;
calculating a first probability for the null hypothesis and calculating a second probability for the trigger hypothesis for the parameter signal for the current computational cycle based at least on a predicted parameter signal, the noise estimate, and the residual;
comparing the first probability and the second probability to a trigger threshold; and
delivering inspiration to the patient when the second probability meets the trigger threshold.

The disclosure additionally describes a ventilation system. The ventilator system includes a pressure generating system, a ventilation tubing system, at least one sensor, and a trigger module. The pressure generating system is configured to generate a flow of breathing gas. The ventilation tubing system includes a patient interface for connecting the pressure generating system to a patient. The at least one sensor is operatively coupled to at least one of the pressure generating system, the patient, and the ventilation tubing system. The trigger module determines a first probability for a null hypothesis and a second probability for a trigger hypothesis based on a monitored parameter signal. The trigger module triggers inspiration when the second probability meets a trigger threshold.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the disclosure.

BRIEF DESCRIPTION OF THE DRAWINGS

The following drawing figures, which form a part of this application, are illustrative of embodiments of systems and methods described below and are not meant to limit the scope of the disclosure in any manner, which scope shall be based on the claims.

DETAILED DESCRIPTION

Figure 1:
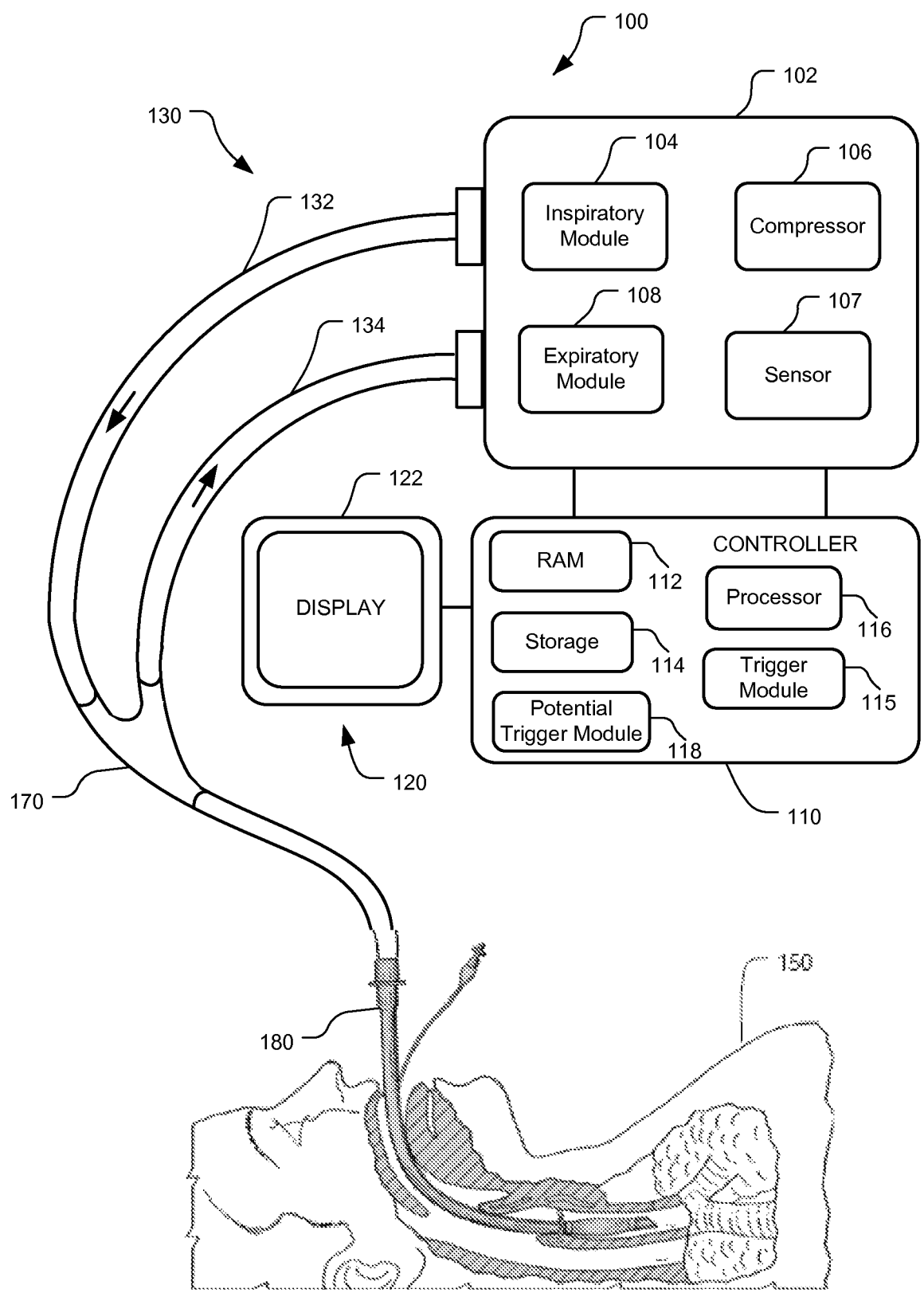
FIG. 1 illustrates an embodiment of a ventilator.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

As each patient may require a different ventilation strategy, modern ventilators can be customized for the particular needs of an individual patient. For example, several different ventilator modes or settings have been created to provide better ventilation for patients in various different scenarios, such as mandatory ventilation modes, spontaneous modes, and assist control ventilation modes. Assist control and spontaneous modes allow a spontaneously breathing patient to trigger inspiration during ventilation.

The response performance of a medical ventilator to a patient trigger from exhalation into inhalation phase represents an important characteristic of a medical ventilator. A ventilator's trigger response impacts the patient's work of breathing and the overall patient-ventilator synchrony. The trigger response performance of a ventilator is a function of a patient's inspiratory behavior (breathing effort magnitude and timing characteristics) as well as the ventilator's gas delivery dynamics and flow control parameters (actuator response, dead bands, etc.).

In conventional triggering modes, a patient's inspiratory trigger is detected based on a comparison of flow and/or pressure signal generated by the patient's inspiratory effort to a predetermined threshold. Having an effective trigger is critical for success in spontaneous (i.e. patient-initiated) ventilation modes and/or breath types. The effectiveness of a trigger can be judged by two major factors: sensitivity to patient initiation and false trigger rate. A common trigger implementation, whether pressure- or flow-based, initiates a spontaneous breath when the pressure or flow crosses a clinician-set threshold. Setting the threshold too low reduces patient effort to trigger a new breath but increases the false trigger rate whereas increasing the threshold will reduce the false trigger rate, but may cause the patient to struggle (i.e., increased work of breathing). If an effective midpoint between these two factors is not found, it may force the patient back on ventilator-initiated breathing, in many cases requiring sedation.

Further, missed inspiration triggering is particularly prevalent during the ventilation of chronic obstructive pulmonary disease patients (COPD). COPD patients demand another breath before they have fully exhaled. As a result, traditional flow triggering modes are not able to detect patient efforts effectively even with the best optimized trigger thresholds.

Accordingly, the systems and methods described herein provide for improved inspiration triggering. The improved inspiration triggering reduces or prevents false triggering even when a low trigger threshold is utilized. This new ventilator synchronization mechanism is referred to herein as the statistical trigger mode ("ST mode"). While the ST mode is referred to herein as a mode, it may also be referred to as a triggering type, breath type, supplemental breath type, or supplemental mode because the ST mode is utilized in conjunction with or in addition to any spontaneous mode or assist control mode of ventilation running any suitable breath type. The ST mode improves ventilator synchrony by improving inspiration trigger detection by utilizing a statistical approach. For example, the ST mode decreases or prevents false triggers and increases the speed of the trigger detection. For example, conventional inspiration triggering modes can require 300 ms or more to detect a patient trigger in patients. The ST mode may decrease this detection time by as much as 270 ms and on average from 80 ms to 181 ms.

Additionally, the systems and methods described herein provide for analyzing and/or displaying the ramifications of a potential change in a trigger threshold for a currently utilized breath type allowing a clinician to view the ramifications of a change in a trigger threshold of a utilized breath type without implementing the change. As such, these systems and methods allow a clinician to determine if the potential trigger threshold would improve trigger patient-ventilator synchrony. The clinician can review the provided data regarding the potential change in trigger and see if that change would increase or decrease false triggers and/or the speed of trigger response time. This information provides the clinician with the information needed to easily and confidently determine if a trigger sensitivity for a current breath type should be changed and by what degree. Previously, the clinician would have to implement the change and watch the patient's response to determine if a change in trigger threshold would be beneficial for the patient, which could increase ventilator asynchrony and the patient's work of breathing.

FIG. 1 is a diagram illustrating an embodiment of an exemplary ventilator 100. The exemplary ventilator 100 illustrated in FIG. 1 is connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple the patient interface 180 (shown as an endotracheal tube in FIG. 1) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor, accumulator and/or other source(s) of pressurized gases (e.g., air, oxygen, and/or helium) is coupled with inspiratory module 104 and the expiratory module 108 to provide a gas source for ventilatory support via inspiratory limb 132. The pneumatic system 102 may include a variety of other components, including mixing modules, valves, tubing, accumulators, filters, etc.

The inspiratory module 104 is configured to deliver gases to the patient 150 and/or through the inspiratory limb 132 according to prescribed ventilatory settings. The inspiratory module 104 is associated with and/or controls an inspiratory valve for controlling gas delivery to the patient 150 and/or gas delivery through the inspiratory limb 132. In some embodiments, inspiratory module 104 is configured to provide ventilation according to various ventilator modes, such as mandatory, spontaneous, and assist modes.

The expiratory module 108 is configured to release gases from the patient's lungs according to prescribed ventilatory settings. The expiratory module 108 is associated with and/or controls an expiratory valve for releasing gases from the patient 150. Further, the expiratory module 108 and/or the inspiratory module 104 may instruct the pressure generating system 102 and/or the inspiratory module 104 to deliver a base flow during exhalation. In an alternative embodiment, the pressure generating system 102 may instruct the inspiratory module 104 to deliver a base flow during exhalation.

The ventilator 100 may also include one or more sensors 107 communicatively coupled to ventilator 100. The sensors 107 may be located in the pneumatic system 102, ventilation tubing system 130, patient interface 180, and/or on the patient 150. The embodiment of FIG. 1A illustrates a sensor 107 in pneumatic system 102.

Sensors 107 may communicate with various components of ventilator 100, e.g., pneumatic system 102, other sensors 107, expiratory module 108, inspiratory module 104, processor 116, controller 110, trigger module 115, potential trigger module 118, and any other suitable components and/or modules. In one embodiment, sensors 107 generate output and send this output to pneumatic system 102, other sensors 107, expiratory module 108, inspiratory module 104, processor 116, controller 110, trigger module 115, potential trigger module 118, and any other suitable components and/or modules.

Sensors 107 may employ any suitable sensory or derivative technique for monitoring and/or measuring one or more patient parameters or ventilator parameters associated with the ventilation of a patient 150 and generate parameter signals. The parameter signals are sent or communicated to other components and/or modules of the ventilator 100. A module as utilized herein is a command and/or control computing devices that may include memory, one or more processors, storage, and/or other components of the type commonly found in command and/or control computing devices. In some embodiments, the signals are sent to the controller 110, processor 116, trigger module 115, and/or potential trigger module 118. In some embodiments, the sensors may generate parameter signals that include parameter measurements every computational cycle. In some embodiments, the computational cycle is every 5 ms. Any suitable computation cycle for a ventilator 100 may be utilized as would be known by a person of skill in the art. In other embodiments, the computation cycle may be anywhere from 2 ms to 20 ms. Sensors 107 may detect changes in patient parameters indicative of patient inspiratory or expiratory triggering, for example. Any sensory device useful for monitoring changes in measurable parameters during ventilatory treatment may be employed in accordance with embodiments described herein.

Sensors 107 may be placed in any suitable location, e.g., within the ventilatory circuitry or other devices communicatively coupled to the ventilator 100. Further, sensors 107 may be placed in any suitable internal location, such as, within the ventilatory circuitry or within components or modules of ventilator 100. For example, sensors 107 may be coupled to the inspiratory and/or expiratory modules 104, 108 for detecting changes in, for example, circuit pressure and/or flow. In other examples, sensors 107 may be affixed to the ventilatory tubing or may be embedded in the tubing itself. According to some embodiments, sensors 107 may be provided at or near the lungs (or diaphragm) for detecting a pressure in the lungs. Additionally or alternatively, sensors 107 may be affixed or embedded in or near wye-fitting 170 and/or patient interface 180. In other embodiments, the sensors 107 are placed in other suitable locations for determining patient triggers based on the selected trigger or breath type. For example, during a neural trigger or breath type, sensors 107 may require endoscopic placement to detect diaphragm neural stimulus.

As should be appreciated, with reference to the Equation of Motion, the ideal gas law, and/or Vander Waals equation, ventilatory parameters are highly interrelated and, according to embodiments, may be either directly or indirectly monitored. That is, parameters may be directly monitored by one or more sensors 107, as described above, or may be indirectly monitored or estimated by derivation according to the Equation of Motion, the ideal gas law, Vander Waals equation, and/or other known relationships.

Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.). In some embodiments, the controller 110 is remote from the ventilator 100 and communicationally coupled to the ventilator 100.

In one embodiment, the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122.

Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100 to display useful information in the form of various ventilatory data regarding the ventilator settings and the physical condition of a patient 150. In some embodiments, the display 122 may illustrate active indicators, potential indicators, different statistics, difference graphs, parameter signals, initial probabilities, mean parameter signals, noise estimates, residuals, calculated probabilities, trigger thresholds, run thresholds, predicted signal parameters, and/or any other information known, received, or stored by the ventilator 100.

In some embodiments, controller 110 includes memory 112, one or more processors 116, storage 114, and/or other components of the type commonly found in command and control computing devices. Controller 110 may further include a trigger module 115 and a potential trigger module 118, as illustrated in FIG. 1. In alternative embodiments, the trigger module 115 and/or potential trigger module 118 are located in other components of the ventilator 100, such as in the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Ventilators 100, during assist and spontaneous modes of operation, trigger inspiration in response to a detected patient effort. The trigger module 115 detects patient efforts based on one or more parameter signals depending upon the selected trigger mode and triggers inspiration in response to a detected patient effort. Different trigger modes utilize different methods for determining a patient effort. For example, in some embodiment, the patient's inspiratory trigger is detected based on a comparison of a flow and/or pressure signal or a change in a flow and/or pressure signal generated by the patient's inspiratory effort to a predetermined threshold. In other embodiments, a patient's neural signals related to his or her inspiratory efforts are compared to a predetermined threshold and utilized to detect a patient's inspiratory effort. In further embodiments, a patient's intrapleural pressure is monitored and compared to a predetermined threshold to detect a patient's inspiratory effort. In other embodiments, a statistical analysis of measured pressure or flow (or other signal) is monitored and compared to a predetermined probability threshold (an ST mode) to detect a patient's inspiratory effort.

Additionally, as discussed above, each of these different trigger modes requires the use of a trigger threshold. The more sensitive the trigger threshold, the less patient effort a patient has to exhibit in order for the trigger module 115 to detect a patient effort. The less sensitive the trigger threshold, the more patient effort the patient has to exhibit in order for the trigger module 115 to detect a patient effort. As discussed above, the response performance of a medical ventilator to a patient trigger from exhalation into inhalation phase represents an important characteristic of a medical ventilator. A ventilator's trigger response impacts the patient's work of breathing and the overall patient-ventilator synchrony. Having an effective trigger is critical for success in spontaneous (i.e. patient-initiated) ventilation modes. The effectiveness of a trigger can be judged by two major factors:

sensitivity to patient initiation and false trigger rate. Setting the threshold too low reduces patient effort to trigger a new breath but increases the false trigger rate whereas increasing the threshold will reduce the false trigger rate, but may cause the patient to struggle. If an effective midpoint between these two factors is not found, it may force the patient back on ventilator-initiated breathing, in many cases requiring sedation.

Figure 6:
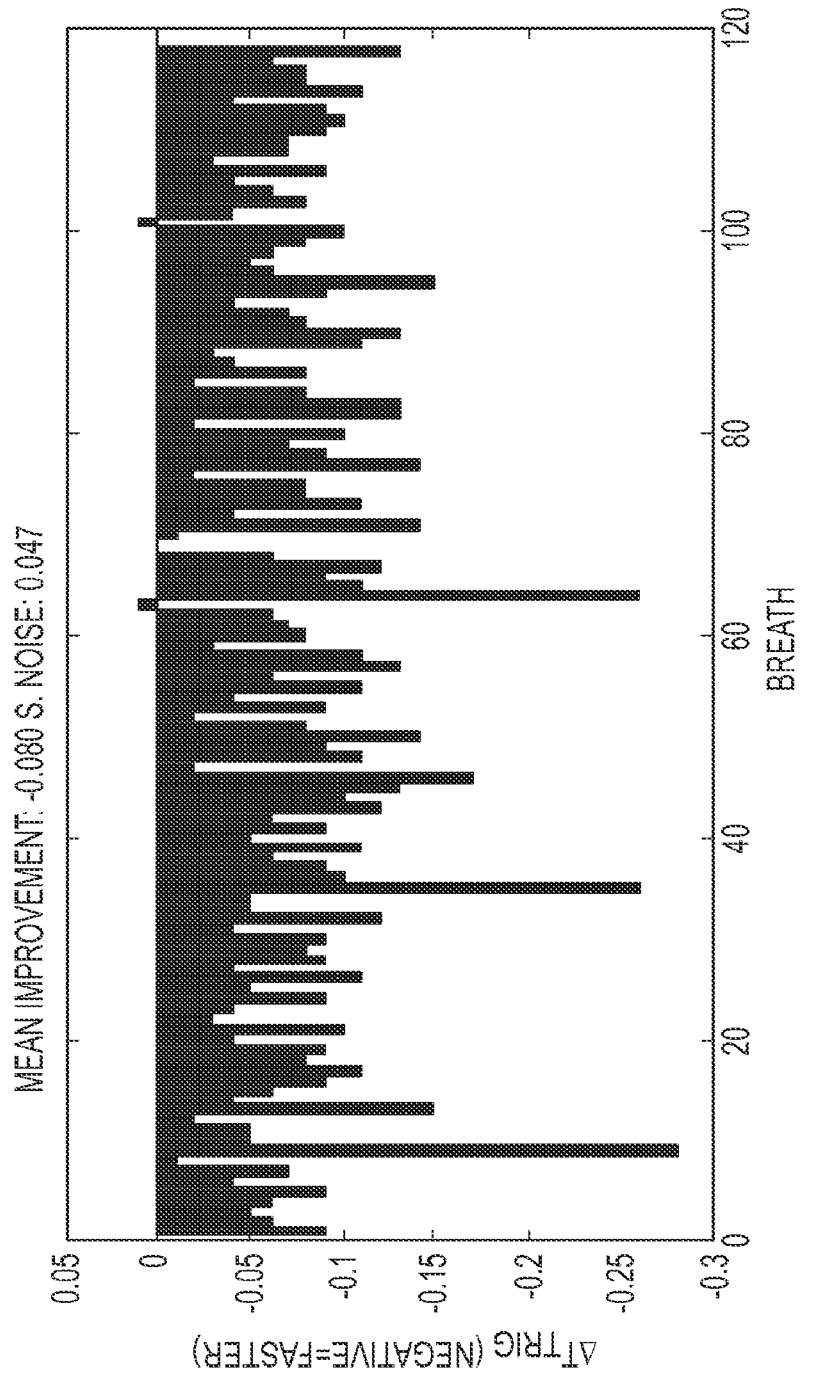
FIG. 6 illustrates an embodiment of a graph showing an improved trigger detection speed for a constant statistical trigger mode when compared to a traditional flow trigger breath type utilized while ventilating a patient on a ventilator.
Figure 9:
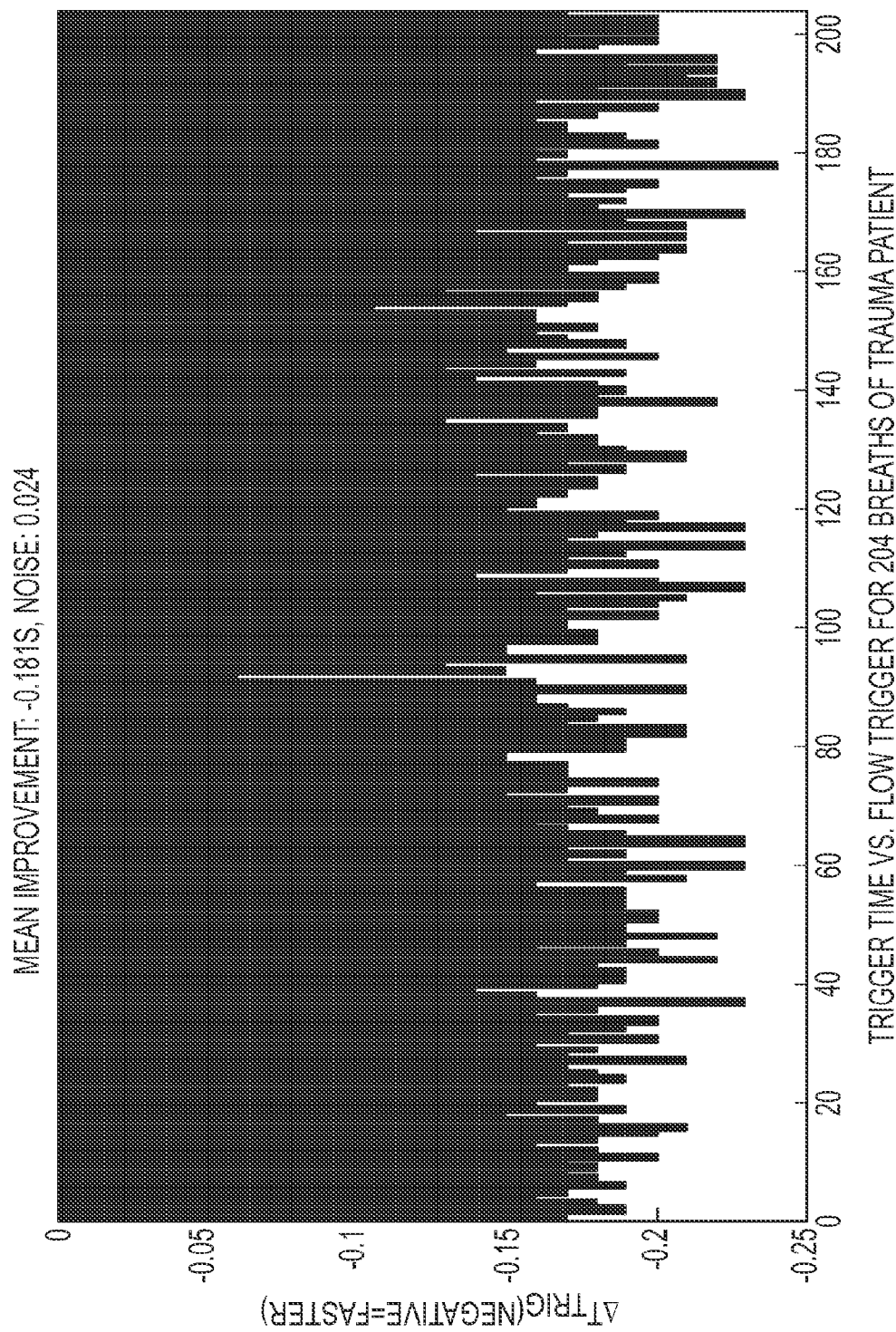
FIG. 9 illustrates an embodiment of a graph showing an improved trigger detection speed for a variable statistical trigger mode when compared to a traditional flow trigger breath type utilized while ventilating a patient on a ventilator.

In order to improve the effectiveness of the trigger, the trigger module 115 may implement a ST mode. The ST mode reduces or prevents auto-triggering even when a low trigger threshold is utilized. The ST mode improves ventilator synchrony by improving inspiration trigger detection. As such, in some embodiments, the ST mode decreases or prevents false triggers and increases the speed of the trigger detection. For example, conventional inspiration flow or pressure triggering modes require about 300 ms or more to detect a patient trigger. The ST mode may decrease this trigger detection time by as much as 270 ms and on average from 80 ms to 181 ms. For example, FIGS. 6 and 9 illustrate an embodiment of graphs showing the improved trigger detection speed for the ST mode when compared to a traditional flow triggering breath type.

Additionally, regardless of the trigger mode utilized by the trigger module 115, the ventilator 100 may utilize a potential trigger module 118 to allow a clinician to refine or find the best trigger threshold for any utilized trigger mode or breath type without having to actually implement a new trigger threshold. In this embodiment, the ventilator 100 utilizes an active trigger threshold (also referred to herein as active trigger setting) to trigger ventilation with the trigger module 115 and utilizes a potential trigger threshold (also referred to herein as a potential trigger setting) to determine where the trigger module 115 would have triggered inspiration if the potential trigger threshold had been utilized to trigger inspiration. Providing this potential trigger information to the clinician and/or providing an analysis of this potential trigger information in comparison to the active trigger, allows a clinician to easily and confidently determine if a potential trigger setting would be beneficial or not for the patient.

The trigger module 115 receives and/or determines an inspiration trigger threshold (also referred to herein as an active trigger setting). In some embodiments, the trigger module 115 receives the active trigger setting from operator input. In other embodiments, the trigger module 115 determines an active trigger setting based on ventilator and/or patient parameters.

The mechanisms for detecting a patient effort by the trigger module 115 for known breath types and/or trigger modes are understood by a person of skill in the art and are therefore, not discussed herein in detail. It is understood by a person of skill in the art, that the trigger module 115 may be utilized to detect patient efforts utilizing these known trigger types or modes (e.g. flow triggering, neural triggering, intrapleural pressure triggering, pressures triggering, etc.). However, the mechanisms for detecting a patient effort utilizing the ST mode are novel and will therefore be discussed in detail below.

The ST mode monitors how a parameter signal statistically changes as opposed to comparing the signal itself against a predefined threshold. To accomplish this, the ST mode utilizes a class of algorithms commonly referred to as change detection, change-point detection, or residual change detection algorithms. In some embodiments, the ST mode utilizes an adopted version of the Multiple-Hypothesis Shiryayev Sequential Probability Ratio Test (MHSSPRT).

The ST mode estimates the probability of whether the null hypothesis and the trigger hypothesis are true. The null hypothesis is analogous to the case where the patient has not yet initiated a breath whereas the trigger hypothesis represents the initiation of a breath. During the ST mode the trigger module 115 updates the noise estimate, calculates the filter residuals, and calculates the probability of each hypothesis. The trigger module 115 determines a patient effort during the ST mode when the probability of the trigger hypothesis exceeds a predefined threshold.

One of the advantages of the ST mode is that the trigger module 115 monitors an estimated value of the parameter signal that is less sensitive to noise, allowing a more sensitive trigger threshold to be set without increasing the false trigger rate. The quality of the monitored signal varies greatly breath-to-breath, especially after changes to the ventilator settings. To account for this quality variation, the ST mode characterizes the noise of the signal and uses this noise to ensure the filter is robust in the presence of increased noise.

Figure 4:
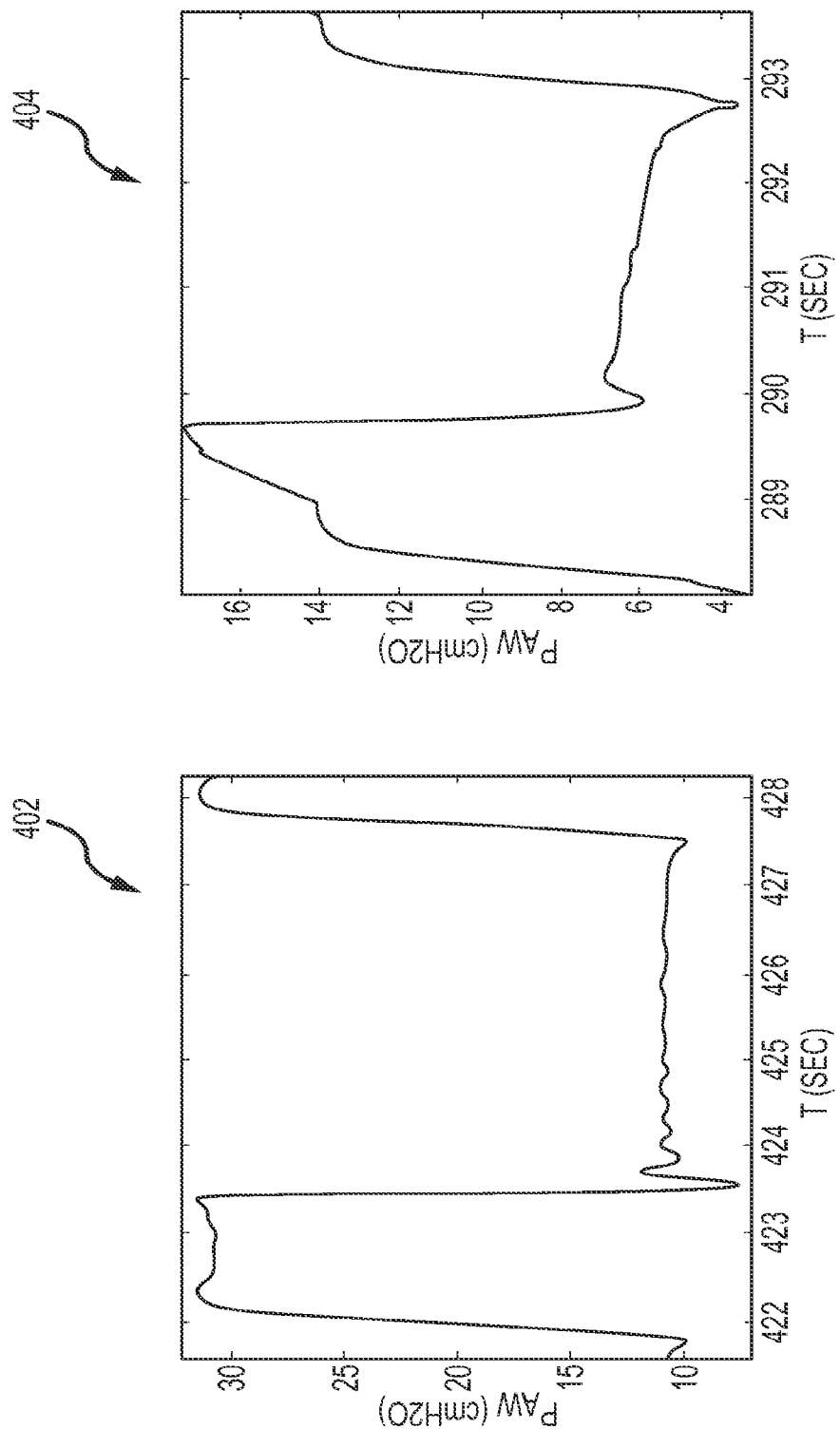
FIG. 4 illustrates an embodiment of a graph of a constant positive-end expiratory pressure (PEEP) signal and a graph of a variable PEEP signals during a single breath while ventilating a patient on a ventilator.

In order to calculate the residuals effectively, the trigger module 115 must have a method of predicting what the parameter signal looks like when a breath has not been initiated, i.e. the null signal. Depending on the breathing mode and lung characteristics, predicting this can be trivial or more involved. If the parameter signal is relatively constant after exhaling, no projection algorithm is required; the signal value from the previous time step can be carried forward. A pressure signal where the pressure measurements settle quickly and remain fairly constant during exhalation is an example of a constant exhalation signal. If the signal does not remain constant during exhalation, a prediction model such as a Kalman Tracking Filter (KTF) can be utilized during the ST mode by the trigger module 115 to project the null signal. As such, two different kinds of ST mode may be utilized by the trigger module 115. A constant ST mode may be utilized by the trigger module 115 when the signal remains fairly constant and a variable ST mode may be utilized by the trigger module 115 when the signal does not remain constant during exhalation. FIG. 4 illustrates an embodiment of a graph of the two different types of pressure signals. Graph 402 illustrates a pressure signal that has a substantially constant PEEP (e.g., a parameter signal that is relatively constant during exhalation). The trigger module 115 would utilize the constant ST mode to trigger ventilation for the parameter signal illustrated in graph 402. Graph 404 illustrates a pressure signal with a descending PEEP (a parameter signal that is not constant during exhalation). The trigger module 115 would utilize the variable ST mode to trigger ventilation for the parameter signal illustrated in graph 404.

In alternative embodiments, the KTF is utilized during other triggering modes to filter monitored signals for triggering. For example, the KTF could be applied to flow signals in a flow triggering breath type or pressure signals in a pressure triggering breath type.

Figure 5:
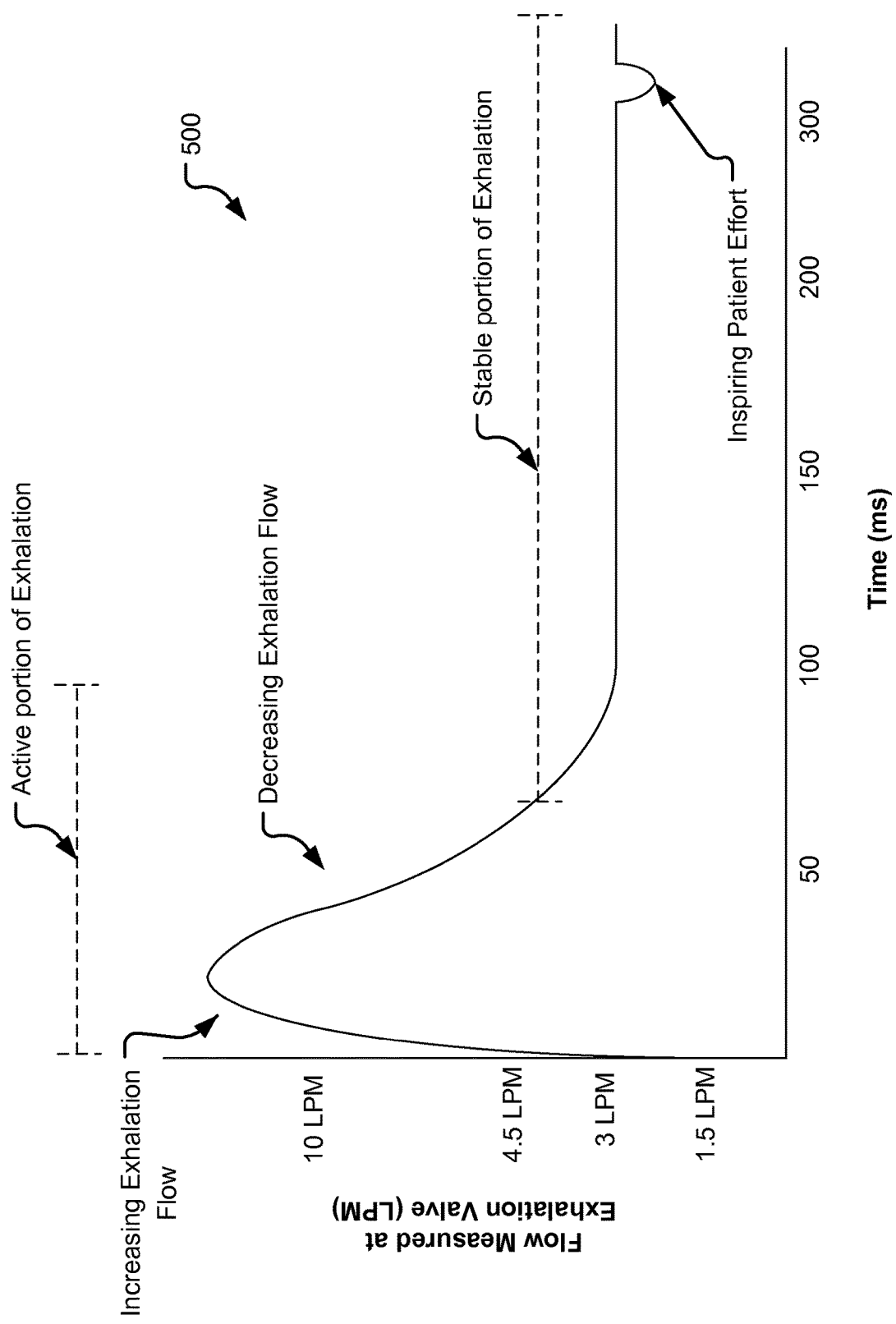
FIG. 5 illustrates an embodiment of a graph of an exhalation flow signal during one breath while ventilating a patient on a ventilator.

During the ST mode, the trigger module 115 determines a stable portion of exhalation based at least on a measurement of the parameter signal for a current computational cycle. A current computational cycle as utilized herein is the most recent computation cycle. A next computational cycle as utilized herein is a future computation cycle that will occur directly after the current computational cycle. The stable portion of exhalation is the portion of exhalation when a patient 150 is contributing very little or no flow and/or pressure through the expiratory limb 134 and is prior to the beginning of inspiration as illustrated in FIG. 5. The stable portion of exhalation usually occurs right after an active portion of exhalation where the flow and/or pressure vary significantly. FIG. 5 illustrates an embodiment of a graph 500 of exhalation flow during one breath while ventilating a patient 150 on a ventilator 100. FIG. 5 further illustrates the active portion and the stable portion of an exhalation.

The trigger module 115 may utilize any suitable method for determining a stable portion of exhalation. In some embodiments, in order to determine the stable portion of exhalation, the trigger module 115 monitors one or more parameter signals, such as exhalation pressure and/or exhalation flow. In some embodiments, the exhaled flow and/or pressure is monitored with an expiratory flow sensor. In other embodiments, the exhaled flow and/or pressure is monitored with an exhalation pressure sensor. In some embodiments, the trigger module 115 monitors the exhalation flow every computation cycle. In some embodiments, the trigger module 115 determines a stable portion of exhalation when the slope of the exhalation flow is zero, about zero, or less than a predetermined threshold. In other embodiments, the trigger module 115 determines a stable portion of exhalation by determining if the difference between the maximum exhalation pressure and the minimum exhalation pressure is less that 1.5 cm of $H_2O$ ((Max$(P_e)$−Min$(P_e)$)<1.5 cm $H_2O$) and/or determines if the difference between maximum exhalation flow and minimum exhalation flow is less than 1.5 LPM ((Max$(Q_e)$−Min$(Q_e)$)<1.5 LPM) during a predetermined interval. In some embodiments, the maximum and minimum values are calculated and compared based on the flow and pressure data saved in a 10-point buffer (e.g., pertaining to a 50 ms predetermined interval). Maximum and minimum values for the moving 10-point windows are tracked each computation cycle during exhalation. If the difference between the maximum exhalation pressure and the minimum exhalation pressure is less that 1.5 cm of $H_2O$ and/or the difference between maximum exhalation flow and minimum exhalation flow is less than 1.5 LPM, then the trigger module 115 determines that the patient 150 is in the stable portion of exhalation (or that active exhalation has been completed). If the difference between the maximum exhalation pressure and the minimum exhalation pressure is not less than 1.5 cm of $H_2O$ and/or the difference between maximum exhalation flow and minimum exhalation flow is not less than 1.5 LPM for a current computation cycle, then the trigger module 115 determines that the patient 150 is not in the stable portion of exhalation (or is in the active portion of the exhalation).

The minimum pressure and flow values of 1.5 LPM are based on the characteristics of an exemplary ventilator. Other values and different pressure and flow levels may be used as appropriate based on the ventilator being currently utilized. Further, depending on the utilized ventilator, the flow and pressure stability thresholds may not necessarily have the same magnitude. The thresholds are selected to provide minimal respiratory activity by the patient.

The embodiments, discussed above are merely exemplary and are not meant to be limiting. Any suitable method for determining a stable period of exhalation may be utilized by the present disclosure.

During a constant ST mode, if the trigger module 115 determines a stable portion of exhalation, the trigger module 115 sets the initial probability (also referred to as a priori probability) for each hypothesis and calculates a mean parameter signal. During a constant ST mode, if the trigger module 115 determines that the parameter signal of the current computational cycle is in an active portion of exhalation, the trigger module 115 continues to monitor the parameter signal and to check for the stable portion of exhalation.

In some embodiments, the trigger module 115 utilizing a constant ST mode assumes that the null hypothesis is true and that the trigger hypothesis is false when setting the initial probability for each of the null hypothesis and the trigger hypothesis for the parameter signal from the first computational cycle of the exhalation. For example, the trigger module 115 may utilize the following equations:

$$F_{k,i} = \pi_i \quad (1)$$

$$F_{0,1} = 1 \quad (2)$$

$$F_{0,2} = 0 \quad (3)$$

where $F_{k,i}$ is the probability of hypothesis i at $t_k$;

$\pi_i$ is the a priori probability of hypothesis i at t=0;

t is time;

i is the current hypothesis; and k is the current computation cycle.

The trigger module 115 utilizing a constant ST mode calculates the mean parameter signal based on a predetermined set of parameter signals for a most recent set of computational cycles since the parameter signal of the null hypothesis is assumed to be constant from one computational cycle to another. For example, the trigger module 115 may utilize the following equation to calculate the mean parameter signal:

$$\bar{x} = \frac{1}{N}\sum_{k=1}^{N} \tilde{x}_k \quad (4)$$

where $\bar{x}$ is the mean parameter;

N is the total number of parameter signals utilized; and $\tilde{x}_k$ is a measurement of the signal at $t_k$ The trigger module 115 utilizing a constant ST mode sets the initial probability for each of the null hypothesis and the trigger hypothesis by adding a hypothesis transition probability to a probability of a previous state for each of the null hypothesis and the trigger hypothesis. For example, the trigger module 115 may utilize the following equation to calculate or set the initial probability for each of the null hypothesis and the trigger hypothesis for the current computational cycle:

$$P_{k,i}(\tilde{X}_{k-1}) = F_{k-1,i} + \tilde{p}_i(1 - F_{k-1,i}) \quad (5)$$

where $P_{k,i}(\tilde{X}_{k-1})$ is an a priori probability of hypothesis i at $t_k$ given measurement history $\tilde{X}_{k-1}$;

$\tilde{p}_i$ is a a priori probability of transition to hypothesis i from $t_k$ to $t_{k+1}$; and $F_{k,i}$ is a probability of hypothesis i at $t_k$.

In some embodiments, the trigger module 115 utilizing the constant ST mode calculates the hypothesis transition probability based on a respiration rate and a sampling frequency. For example, the trigger module 115 may utilize the following equation to calculate the hypothesis transition probability:

$$\tilde{p}_i = \frac{RR}{60f} \quad (6)$$

where
RR is a respiratory rate (breaths per minute); and
$f$ is a sampling frequency (Hz).

In alternative embodiments, the probability of transition increases as exhalation time (t) approaches t=60/RR, allowing the trigger module 115 to react more aggressively as exhalation time approaches the average time between breaths.

The trigger module 115 utilizing the constant ST mode also calculates or updates the noise estimate based at least on the mean parameter signal. In some embodiments, this is accomplished by the trigger module 115 calculating the standard deviation for all the parameter signals for each measured computational cycle taken so far during the exhalation. For example, the trigger module 115 may utilize the following equation to calculate the noise estimate:

$$\sigma = \sqrt{\frac{1}{1-N}\sum_{k=1}^{N}(\tilde{x}_k - \bar{x})^2} \quad (7)$$

where
$\tilde{x}_k$ is a measurement of the signal at $t_k$; and
$\sigma$ is the standard deviation (or noise estimate).

The trigger module 115 utilizing the constant ST mode also calculates a residual for the null hypothesis and the trigger hypothesis based at least on the parameter signal for the current computational cycle. For example, the trigger module 115 may utilize the following generalized equation to calculate the residual for each hypothesis:

$$R_i(x_k) = \tilde{x}_k - H_{k,i} \quad (8)$$

where
$R_i(x_k)$ is a residual of hypothesis i at $t_k$; and
$H_{k,i}$ A priori estimate of x at $t_k$ for hypothesis i.

In some embodiments, the trigger module 115 utilizing the constant ST mode calculates the residual for the null hypothesis by subtracting the mean value for the null hypothesis from the parameter signal for the current computational cycle. For example, the trigger module 115 may utilize the following equation to calculate the residual for the null hypothesis:

$$R_1(x_k) = \tilde{x}_k - \tilde{x} \quad (9)$$

In further embodiments, the trigger module 115 utilizing the constant ST mode calculates the residual for the trigger hypothesis by subtracting a predicted mean value for the trigger hypothesis from the parameter signal for the current computational cycle. In some embodiments, the predicted mean value for the trigger hypothesis is calculated by the trigger module 115 by subtracting a clinician-specified trigger setting with the mean value of the signal. For example, the trigger module 115 may utilize the following equation to calculate the residual for the trigger hypothesis:

$$R_2(x_k) = \tilde{x}_k(\tilde{x} - b) \quad (10)$$

where
b is a breath trigger setting.

Next, the trigger module 115 utilizing the constant ST mode calculates a first probability for the null hypothesis for the parameter signal for the current computational cycle based on the initial probability for the null hypothesis, the noise estimate, and the residual for the null hypothesis. The trigger module 115 utilizing the constant ST mode also calculates a second probability for the trigger hypothesis for the parameter signal for the current computational cycle based on the initial probability for the trigger hypothesis, the noise estimate, and the residual for the trigger hypothesis. In some embodiments, the trigger module calculates the first and second probabilities by calculating a probability density function for each of the null hypothesis and the trigger hypothesis and by multiplying the probability density function for each hypothesis with its corresponding initial probability and normalizing. For example, the trigger module 115 may utilize the following equation to calculate the probability density function for each of the hypotheses:

$$f_i(x_k) = \left(\frac{1}{\sqrt{2\pi}\,\sigma}\right)^{\left(\frac{R_i(x_k)^2}{2\sigma^2}\right)} \quad (11)$$

where
$f_i(x_k)$ is a probability density function of x given hypothesis i.

In another example, the trigger module 115 may utilize the following equation to calculate the first and second probabilities (e.g., multiplying the probability density function with its corresponding initial probability and normalizing):

$$F_{k,i} = \frac{P_{k,i}(\tilde{X}_{k-1}) \cdot f_i(x_k)}{\sum_{i=0}^{m} P_{k,i}(\tilde{X}_{k-1}) \cdot f_i(x_k)} \quad (12)$$

where
$F_{k,i}$ is a probability of hypothesis i at $t_k$.

During a variable ST mode, if the trigger module 115 determines that the parameter signal for a current computational cycle is in an active portion of exhalation, the trigger module 115 continues to monitor the parameter signal and to check for the stable portion of exhalation. During a variable ST mode, if the trigger module 115 determines that the parameter signal for the current computational cycle is in a stable portion of exhalation, the trigger module 115 calculates an initial predicted parameter signal (also referred to herein as a priori estimate at current computational cycle ($t_k$)) and an initial covariance (also referred to herein as an a priori estimate of covariance at $t_k$) for the next computational cycle and calculates a post predicted signal (also referred to herein as a posterori estimate at $t_k$) and a post covariance rate (also referred to herein as a posterori estimate of covariance for at $t_k$) for the next computational cycle. The covariance for a predicted signal is the estimated uncertainty for the predicted parameter. For example, the covariance for the predicted signals illustrated in FIG. 11 can be used to construct the error bounds shown in graph 1102, 1104, or 1106.

In some embodiments, an initial confidence rate for the initial predicted parameter signal and a post confidence rate for the post predicted signal are determined by the trigger module 115. The confidence rate is a quantification of how likely a predicted signal will match the parameter signal of the next computational cycle. In some embodiments, the confidence rate for a predicted signal is directly dependent upon the calculated covariance for the predicted signal. For example, the initial confidence rate may be determined based on the a priori estimate of covariance. In another example, the post confidence rate may be determined based on a posterori estimate of covariance. The higher the covariance for a predicted signal, the lower the confidence rate for the predicted signal. The lower the covariance for a predicted signal, the higher the confidence rate for the predicted signal.

In some embodiments, the trigger module 115 utilizing a variable ST mode assumes that the null hypothesis is true and that the trigger hypothesis is false when calculating the initial predicted parameter signal and the post predicted parameter signal for the parameter signal of the first computational cycle of the exhalation. In some embodiments, the trigger module 115 utilizing a variable ST mode calculates the initial predicted parameter signal for the next computational cycle and the initial covariance for the initial predicted parameter signal for the parameter signal (or true state of the measurement (x)) for the current computational cycle. In further embodiments, the trigger module 115 calculates the post predicted parameter signal for the next computational cycle and the post covariance for the post predicted parameter signal for a first derivative (velocity state ($\dot{x}$)) and a second derivative (acceleration state ($\ddot{x}$)) of the parameter signal for the current computational cycle. In other words, the trigger module 115 analyzes the actual signal parameter (x), the first derivative of the signal parameter ($\dot{x}$), and second derivative of the signal parameter ($\ddot{x}$) for a current computational cycle to predict the signal parameter for the next computational cycle for the null hypothesis and the trigger hypothesis. For example, the three different states are shown in the equation below:

$$X_k = \begin{bmatrix} x \\ \dot{x} \\ \ddot{x} \end{bmatrix} \quad (13)$$

Within a breath, the trigger module 115 utilizing the variable ST mode assumes that the true acceleration state is not time-varying. As such, the trigger module 115 estimates the true value of the acceleration state. For example, the trigger module 115 may utilize the following state transition matrix:

$$\Phi = \begin{bmatrix} 1 & t & \frac{1}{2}t^2 \\ 0 & 1 & t \\ 0 & 0 & 1 \end{bmatrix} \quad (14)$$

In some embodiments, at t=0, both the initial covariance estimate (M) and post covariance estimate (P) are constructed by the trigger module 115 using measurement noise ($\upsilon$) to define the diagonals, ignoring the coupled covariance values, an example of which is illustrated below:

$$M = P = \begin{bmatrix} v & 0 & 0 \\ 0 & \frac{2v}{\Delta t} & 0 \\ 0 & 0 & \frac{2v}{\Delta t^2} \end{bmatrix} \quad (15)$$

In order to prevent the filter from collapsing, a small amount of process noise (V) is injected at each time step by the trigger module 115. For example, the structure of this process noise may be defined as follows:

$$V = \begin{bmatrix} v_p & 0 & 0 \\ 0 & v_v & 0 \\ 0 & 0 & v_a \end{bmatrix} \quad (16)$$

In some embodiments, the trigger module 115 utilizes Kalman Tracking Filter equations to calculate the initial predicted parameter signal at the initial covariance and the post predicted signal at the post covariance for the next computational cycle. For example, the trigger module 115 may utilize the following Kalman Tracking Filter equations to calculate the initial predicted parameter signal at the initial covariance and the post predicted signal at the post covariance for the next computational cycle:

$$\tilde{x}_k = HX_k + \upsilon \quad (17)$$

$$\overline{X}_{k+1} = \Phi \hat{X}_k \quad (18)$$

$$M_{k-1} = \Phi P_k \Phi^T + V \quad (19)$$

$$K_{k+1} = M_{k+1} H^T (HM_{k+1} H^T + V)^{-1} \quad (20)$$

$$R_{k+1} = H\overline{X}_{k+1} - \tilde{x}_{k+1} \quad (21)$$

$$\hat{X}_{k+1} = \overline{X}_{k+1} - K_{k+1} R_{k+1} \quad (22)$$

$$P_{k+1} = M_{k+1} - K_{k+1} HM_{k+1}^T \quad (23)$$

where
$\tilde{x}_k$ is a measurement of the signal at $t_k$;
H is an observability matrix of state X;
$X_k$ is a True state at $t_k$;
$\upsilon$ is a measurement noise;
$\overline{X}_k$ is an a priori estimate of state of at $t_k$;
$\Phi$ is a state transition matrix from $t_k$ to $t_{k+1}$;
$\hat{X}_k$ is a posteriori estimate of state at $t_k$;
$M_k$ is an a priori estimate of covariance at $t_k$;
$P_k$ is a posteriori estimate of covariance at $t_k$;
V is a process noise;
$K_{k+1}$ is a Kalman gain at $t_{k+1}$; and
$R_{k+1}$ is a residual at $t_{k+1}$.

In some embodiments, the variable ST mode utilizes the states and covariance of the Kalman Tracking Filter instead of the initial mean parameter signal used by the trigger module 115 during a constant ST mode to calculate the probability of the null hypothesis and/or trigger hypothesis being true.

After the trigger module 115 utilizing the variable ST mode calculates the predicted signal parameters (e.g., the initial and the post), the trigger module 115 determines if it is ready to calculate the first and second probabilities based on a predetermined run threshold. The predetermined run threshold may be determined based on user input or by the ventilator based on ventilator and patient parameters. In some embodiments, the run threshold is a minimum exhalation time. For example, the minimum exhalation time may be an exhalation time of at least 50 ms. In other examples the minimum exhalation may be an exhalation time of at least 60 ms, 70 ms, 75 ms, 80 ms, 90 ms, 100 ms, 125 ms, 150 ms, 175 ms, 200 ms, and etc. This list is exemplary and is not meant be limiting. Any suitable minimum exhalation time as would be known by a person of skill in the art may be utilized as the run threshold by the trigger module 115. In alternative embodiments, the predetermined run threshold is a maximum calculated covariance for the initial predicted signal parameter and/or the post predicted signal parameter. Any suitable maximum covariance limit as would be known by a person of skill in the art may be utilized at the run threshold by the trigger module 115. In other embodiments, the predetermined run threshold is a minimum confidence rate for the initial predicted signal parameter and/or the post predicted signal parameter. For example, the minimum confidence rate may be a confidence rate of at least 50%. In other examples the minimum confidence rate may be at least 55%, 60%, 65%, 70%, 75%, 80%, 85%, 90%, 95%, 98%, 99%, and etc. This list is exemplary and is not meant be limiting. Any suitable minimum confidence rate as would be known by a person of skill in the art may be utilized at the run threshold by the trigger module 115.

During a variable ST mode, if the trigger module 115 determines that the run threshold has been met, the trigger module 115 calculates the probability for each of the hypotheses. During a variable ST mode, if the trigger module 115 determines the run threshold has not been met, the trigger module 115 continues to monitor the parameter signal and to calculate the initial and post predicted values (if a stable portion of exhalation is found).

The trigger module 115 utilizing the variable ST mode also calculates or updates the noise estimate based at least on a single value of the covariance to determine at least one of the initial covariance and the post covariance. In some embodiments, this is accomplished by the trigger module 115 calculating the square root of P(1,1) in equation #15 listed above. In some embodiments, this is accomplished by the trigger module 115 by utilizing the measurement noise ($\upsilon$).

The trigger module 115 utilizing the variable ST mode also calculates a residual for the null hypothesis and the trigger hypothesis based at least on the parameter signal for the current computational cycle. In some embodiments, the trigger module 115 utilizing the variable ST mode calculates the residual for the null hypothesis by subtracting the initial predicted value from the parameter signal for the current computational cycle. For example, the trigger module 115 may utilize the following equation to calculate the residual for the null hypothesis:

$$R_1(x_k) = \tilde{x}_k - \overline{X}_k(1) \quad (24)$$

where
(1) is cell number 1 of the vector.
In further embodiments, the trigger module 115 utilizing the variable ST mode calculates the residual for the trigger hypothesis by subtracting an initial predicted parameter signal for the trigger hypothesis from the parameter signal for the current computational cycle. For example, the trigger module 115 may utilize the following equation to calculate the residual for the trigger hypothesis:

$$R_2(x_k) = \tilde{x}_k - (\overline{X}_k(1) - b) \quad (25)$$

Next, the trigger module 115 utilizing the variable ST mode calculates a first probability for the null hypothesis for the parameter signal for the current computational cycle based on the initial predicted parameter signal for the null hypothesis, the noise estimate, and the residual for the null hypothesis. The trigger module 115 utilizing the variable ST mode also calculates a second probability for the trigger hypothesis for the parameter signal for the current computational cycle based on the initial predicted parameter signal for the trigger hypothesis, the noise estimate, and the residual for the trigger hypothesis. In some embodiments, the trigger module 115 calculates the first and second probabilities by calculating a probability density function for each of the null hypothesis and the trigger hypothesis and by multiplying the probability density function for each hypothesis with its corresponding predicted signal parameter and normalizing. For example, the trigger module 115 may utilize equation #11 to calculate the probability density function for each of the hypotheses. In another example, the trigger module 115 may utilize equation #12 (e.g., multiplying the probability density function with its corresponding predicted signal parameter and normalizing) to calculate the first and second probabilities.

Once the probabilities for the null and trigger hypothesis are calculated, the trigger module 115 utilizing either type of ST mode compares each probability to a trigger threshold. If the trigger module 115 determines that null hypothesis meets the trigger threshold, the trigger module 115 does not detect a patient effort and monitors the parameter signal for the next computational cycle. If the trigger module 115 determines that trigger hypothesis meets the trigger threshold, the trigger module 115 detects a patient effort and triggers inspiration ending exhalation. The trigger threshold, as discussed above, may be selected by a user or selected by the ventilator based on ventilator and patient parameters. In some embodiments, the trigger threshold is a minimum probability. For example, the minimum probability may be at least 50%. In another example, the minimum probability may be at least 95%. In other examples, the minimum probability is at least 55%, 60%, 65%, 70%, 75%, 80%, 85%, 90%, 98%, 99%, and etc. This list is exemplary and is not meant be limiting. Any suitable minimum probability as would be known by a person of skill in the art may be utilized as the trigger threshold by the trigger module 115.

In other embodiments, the ventilator 100 is preconfigured to deliver an inspiration after a predetermined amount of exhalation time to prevent a patient 150 from becoming under-ventilated. Accordingly, the predetermined amount of exhalation time (e.g., known as an apnea interval in some ventilators) may also be a trigger threshold in this embodiment. For example, the trigger module 115 will automatically trigger an inspiration after 20 seconds, 30 seconds, or 60 seconds of exhalation time. In some embodiments, the predetermined amount of time is determined by the clinician and/or ventilator 100 based on whether the patient 150 is an infant, child, adult, male, female, and/or suffering from a specific disease state.

If the trigger module 115 determines that ventilator and/or patient parameters meet and/or exceed an inspiration trigger threshold during exhalation, the trigger module 115 instructs the inspiratory module 104 to deliver an inspiration, which effectively ends the exhalation phase. If the trigger module 115 determines that ventilator and/or patient parameters does not meet and/or exceed an inspiration trigger threshold during exhalation, the trigger module 115 continues to monitor the ventilator and/or patient parameters and compare them to a trigger threshold until the ventilator and/or patient parameters meet and/or exceed a trigger threshold.

As discussed above, each of the two kinds of the ST mode decreases the ventilator's trigger detection response time. In one embodiment, where the constant ST mode was utilized to ventilate a patient with chronic obstructive pulmonary disease (COPD), the constant ST mode decreased the ventilator's trigger detection time by about 0.080 seconds when compared to a conventional flow triggering type, as illustrated in FIG. 6. In another embodiment, where the variable ST mode was utilized to ventilate a patient with lung trauma, the variable ST mode decreased the ventilator's trigger detection time by about 0.181 seconds when compared to a conventional flow triggering type, as illustrated in FIG. 9.

Figure 7:
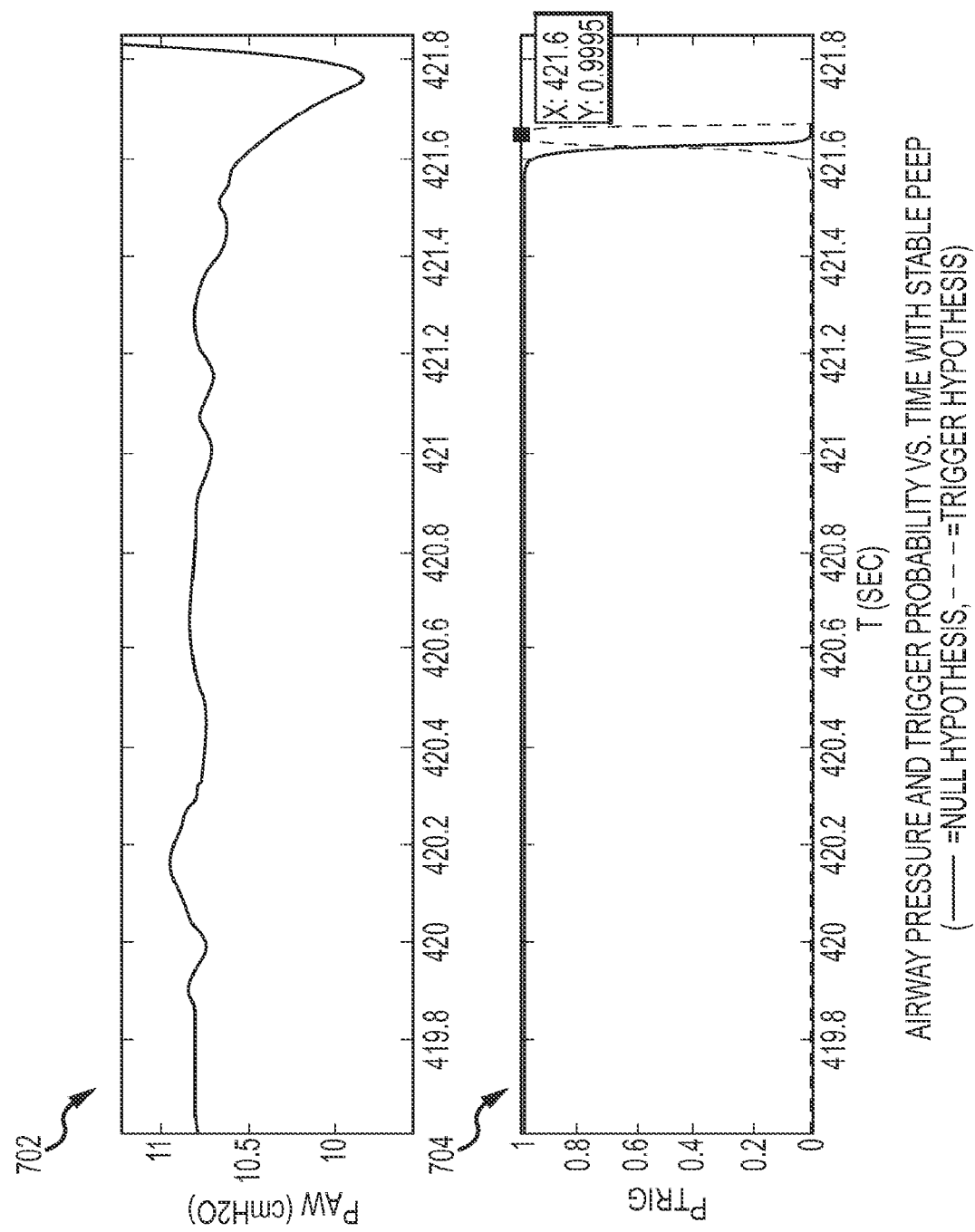
FIG. 7 illustrates an embodiment of a graph of pressure versus time for an exhalation with a constant PEEP and illustrates a corresponding graph of the calculated probabilities for a null and trigger hypotheses by a constant ST mode versus time for the same exhalation.

FIG. 7 illustrates an embodiment of a graph 702 of pressure versus time for an exhalation with a constant PEEP and illustrates a graph 704 of the calculated null and trigger probabilities by a constant ST mode versus time for the same exhalation. As shown in graph 704 of FIG. 7, the probability of the null hypothesis remains at 100% until just before 421.6 seconds. Similarly, the probability of the trigger hypothesis remains at 0% until just before 421.6 seconds, as illustrated in graph 704 of FIG. 7. As is logical, the probability of the null hypotheses being true goes down as the probability of the trigger hypothesis being true increases. In this embodiment, the constant ST mode detected a patient trigger or the patient's inspiratory effort when the probability of the trigger hypothesis became larger than the 99% minimum probability trigger setting.

Figure 8:
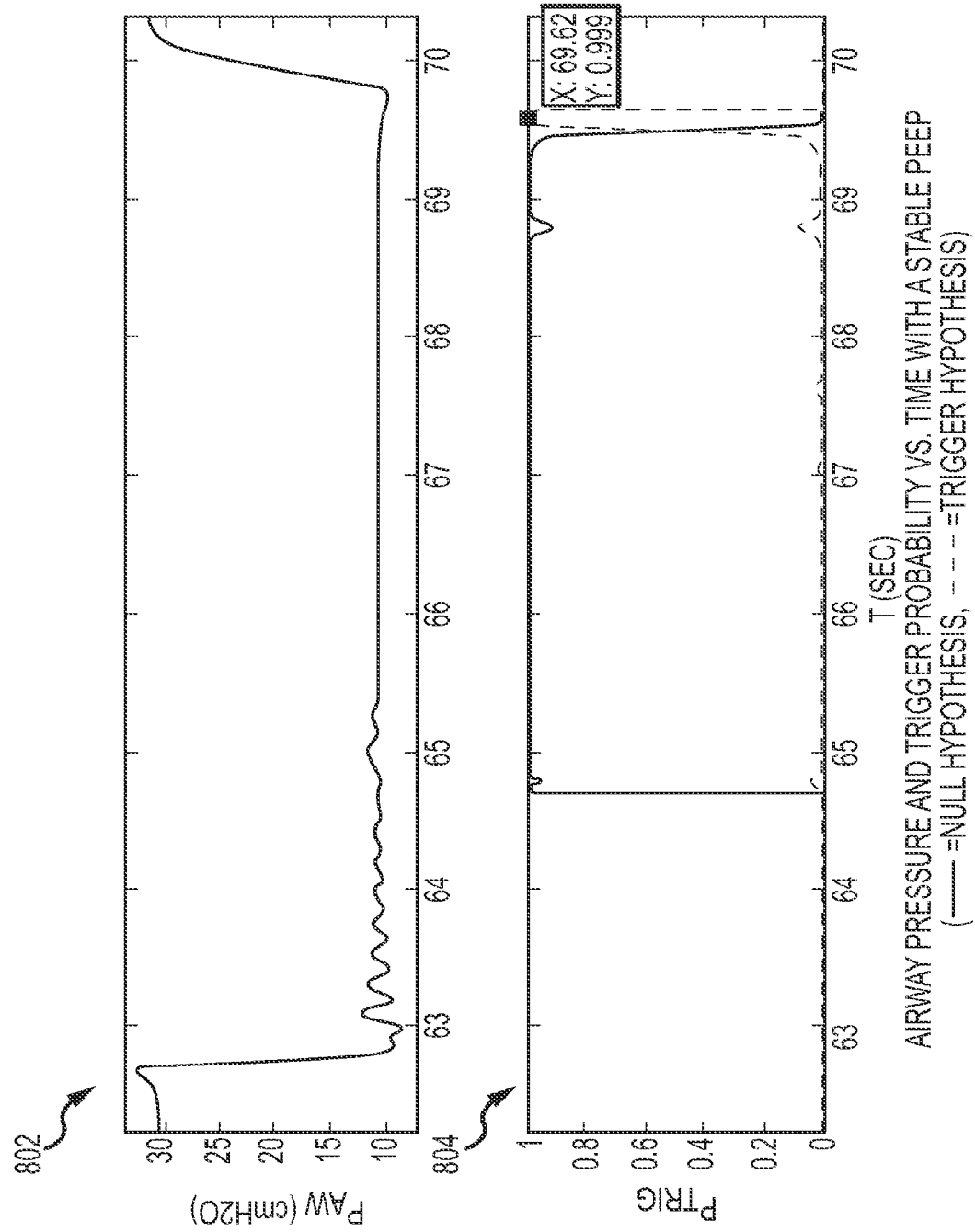
FIG. 8 illustrates an embodiment of a graph of pressure versus time for an exhalation with a constant PEEP and illustrates a corresponding graph of the calculated probability for a null and trigger hypotheses by a constant ST mode versus time for the same exhalation.

FIG. 8 illustrates an embodiment of a graph 802 of pressure versus time for an exhalation with a substantially constant PEEP and illustrates a graph 804 of the calculated null and trigger probabilities by a constant ST mode versus time for the same exhalation. As shown in graph 804 of FIG. 8, the probability of the null hypothesis remains at 100% until just before 69 seconds, where a slight change in the probability is detected based a slight change in the pressure signal parameter. Similarly, the probability of the trigger hypothesis remains at 0% until just before 69 seconds, as illustrated in graph 804 of FIG. 8. The noise estimate of the constant ST mode prevents the ventilator from detecting a false trigger based on this slight change in the signal parameter just before 69 seconds. However, both probabilities did not significantly change until after 69 seconds when the pressure signal changed more significantly. In this embodiment, the constant ST mode detected a patient trigger or the patient's inspiratory effort when the probability of the trigger hypothesis became larger than the 99% minimum probability trigger threshold at around 69.62 seconds.

Figure 10:
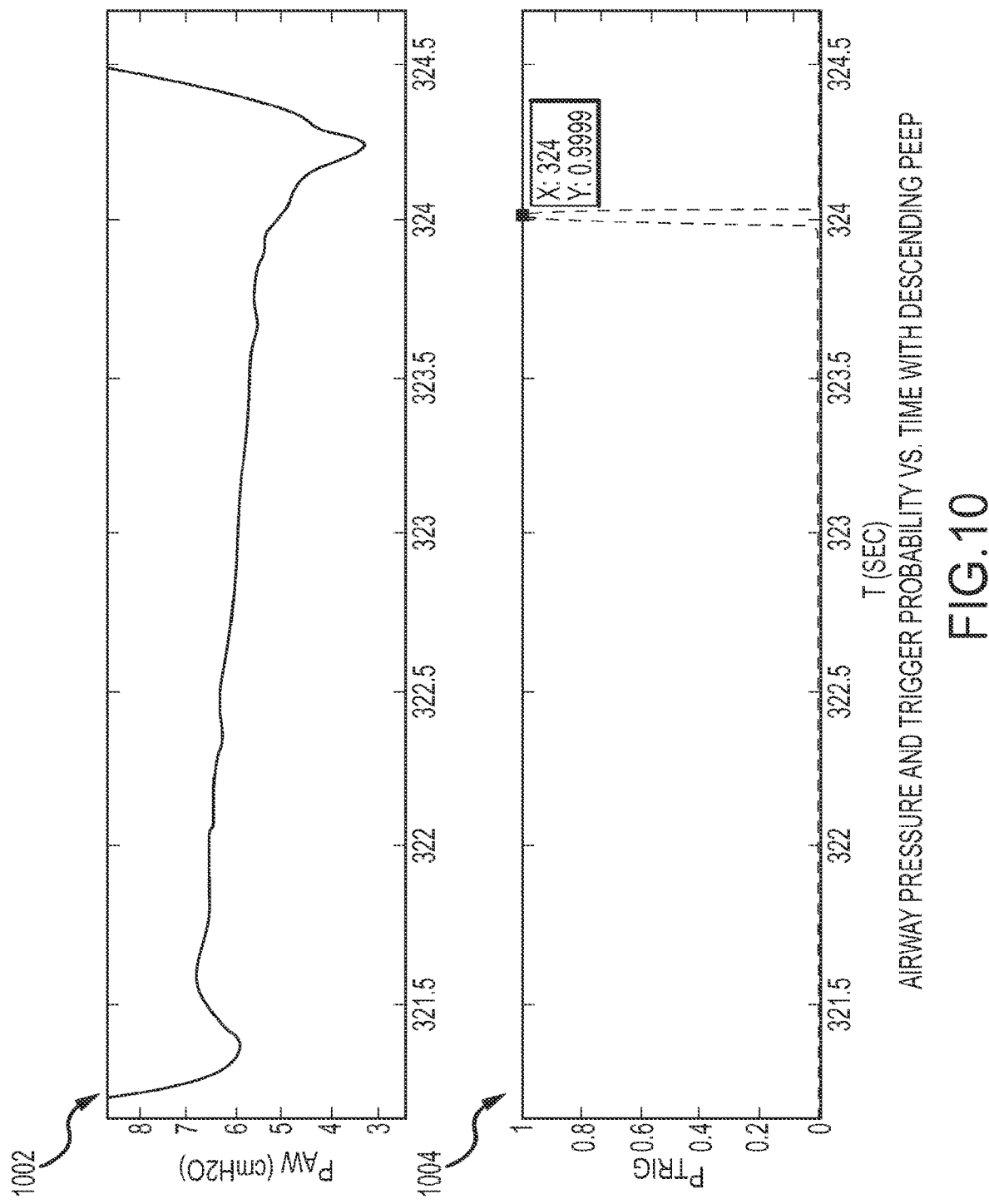
FIG. 10 illustrates an embodiment of a graph of pressure versus time for an exhalation with a constant PEEP and illustrates a corresponding graph of the calculated probability of a trigger hypothesis by a constant ST mode versus time for the same exhalation.
Figure 11:
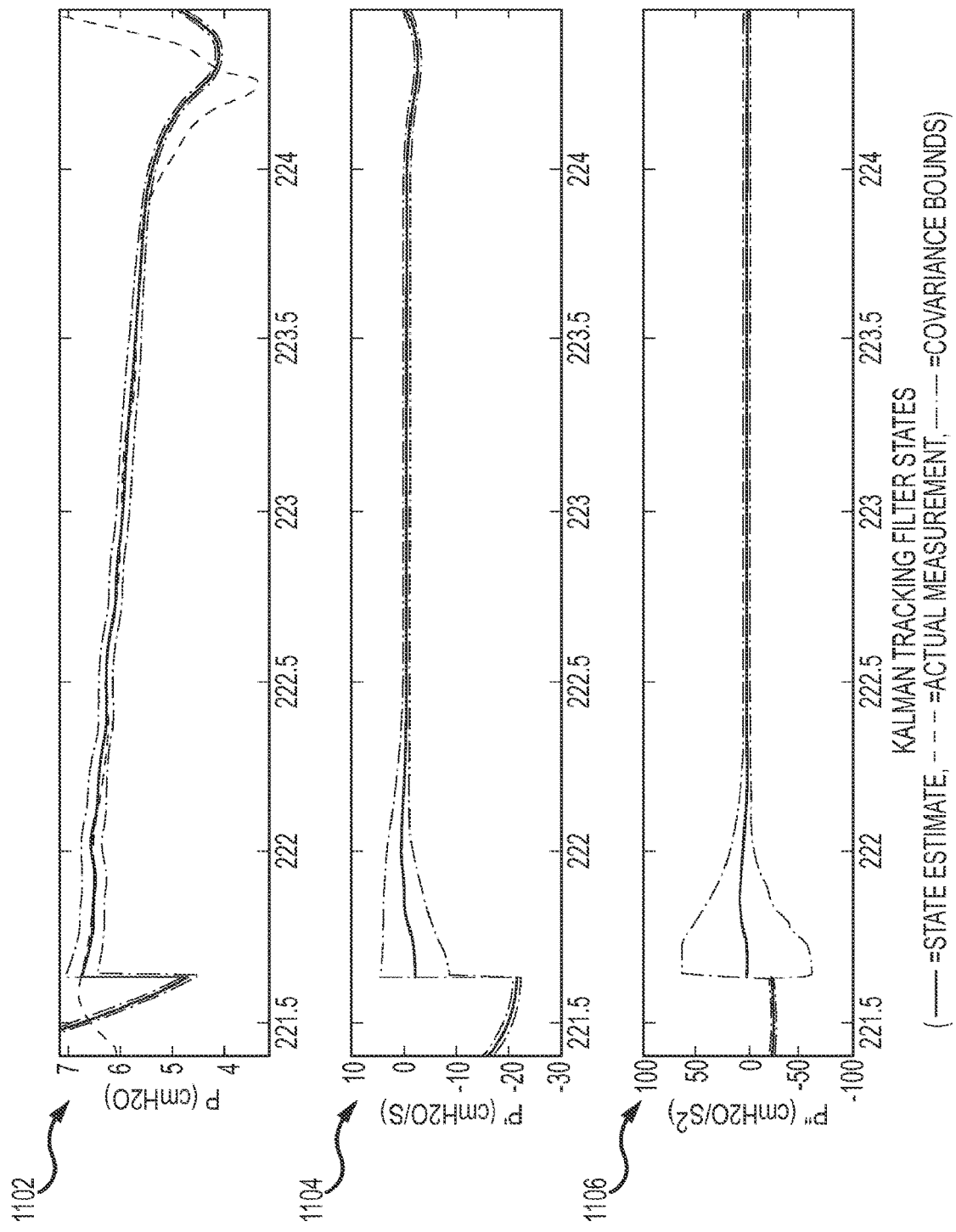
FIG. 11 illustrates an embodiment of a graph of a predicted signal and its covariance for a measured pressure signal, a graph of a second predicted signal and its covariance for the first derivative of the measured pressure signal, and a graph of a third predicted signal and its covariance for the second derivative of the measured pressure signal for the same exhalation as illustrated in FIG. 10.

FIG. 10 illustrates an embodiment of a graph 1002 of pressure versus time for an exhalation with a descending PEEP and illustrates a graph 1004 of the calculated trigger probability by a variable ST mode versus time for the same exhalation. As shown in graph 1004 of FIG. 10, the probability of the trigger hypothesis remains at 0% until just before 324 seconds, as illustrated in graph 1004 of FIG. 10. In this embodiment, the variable ST mode detected a patient trigger or the patient's inspiratory effort when the probability of the trigger hypothesis became larger than the 99% trigger setting at 324 seconds. FIG. 11 illustrates an embodiment of a graph showing the predicted signal and its uncertainty bounds for the measured pressure signal 1102, a graph showing the predicted signal and its uncertainty bounds for the first derivative of the measured pressure signal 1104, and a graph showing the predicted signal and its uncertainty bounds for the second derivative of the measured pressure signal 1106 for the same exhalation as illustrated in FIG. 10. In some embodiments, the covariance for the measured pressure signal illustrated in graph 1102 is calculated based on known pressure sensor errors. As illustrated by graphs 1102, 1104, and 1106, the covariance of the second derivative of the parameter signal is larger than the covariance for the first derivative of the pressure signal and is larger than the covariance for the measured pressure signal until 322.5 seconds is reached. For example, the run threshold of the variable ST mode may be met for the exhalation illustrated in FIGS. 10 and 11, when the covariance drops below a threshold limit or when a confidence rate calculated based on the covariance is over 90% for the first derivative and/or the second derivative as illustrated at 322.5 seconds.

As discussed above, the ventilator 100 may also include a potential trigger module 118. The potential trigger module 118 receives a potential trigger setting (also referred to as a potential trigger threshold) for the utilized breath type. The potential trigger setting is any trigger threshold that is different than the active trigger setting for the current breath type being utilized by the trigger module 115 to detect patient efforts and trigger inspiration. For example, in some embodiments, the active trigger setting and the potential trigger setting are two different flow triggering thresholds. In other embodiments, the active trigger setting and the potential trigger setting are two different pressure triggering thresholds. In additional embodiments, the active trigger setting and the potential trigger setting are two different intrapleural pressure triggering thresholds. In further embodiments, the active trigger setting and the potential trigger setting are two different neural triggering thresholds. In other embodiments, the active trigger setting and the potential trigger setting are two different probability triggering thresholds. As would be understood by a person of skill in the art, the active and potential trigger settings may be any known type of triggering threshold for any known breath type.

The potential trigger module receives the potential trigger setting from user input or selection. In some embodiments, the potential trigger module 118 is activated by user input or selection. For example, the operator of the ventilator 100 may turn on or activate a potential trigger application, which in turn activates or turns on the potential trigger module 118. In some embodiments, the potential trigger module receives a potential trigger from user input only after a potential trigger application has been activated by the operator.

In additional embodiments, the application, trigger module 118, or ventilator 100 tests a series of potential triggers. In some embodiments, the operator selects a potential trigger setting for implementation by the ventilator based on the displayed potential trigger and active trigger information. In alternative embodiments, a potential trigger setting for implementation is selected automatically by the application, trigger module 118, or ventilator 100 based on the testing of the series of potential triggers. In some embodiments, the ventilator 100, trigger module 118, or application picks a trigger setting with the best improvement in trigger time while minimizing false triggers from the series of potential triggers tested.

The potential trigger module 118 and the trigger module 115 monitor respiratory data (including one or more parameter signals) with one or more sensors 107. The respiratory data may be any monitored parameter signal or parameters derived therefrom. As discussed above, the trigger module 115 detects a patient effort when the monitored respiratory data breaches the active trigger setting and triggers or delivers inspiration based on this detected patient effort. The detected patient effort utilized by the trigger module 115 to deliver inspiration is referred to herein as the active patient trigger. The potential trigger module 118 monitors the same respiratory data as the trigger module 115 but compares the respiratory data to the received potential threshold to detect the patient effort. The potential trigger module 118 detects a potential patient trigger when the respiratory data breaches the potential trigger setting. However, the potential trigger module 118 does not deliver or trigger inspiration based on the detected potential patient trigger, but instead displays information based on one or more detected potential patient triggers and one or more detected active patient triggers.

In some embodiments, the monitored parameter signals are saved in storage 114. In these embodiments, the potential trigger module 118 upon activation may post-process these saved signals to determine past potential patient triggers. Accordingly, in these embodiments, the saved data or a subset of the saved monitored parameter signals can be analyzed for potential triggers by the potential trigger module 118 and presented to the clinician on the display 122 upon selection of the potential patient trigger.

Figure 12:
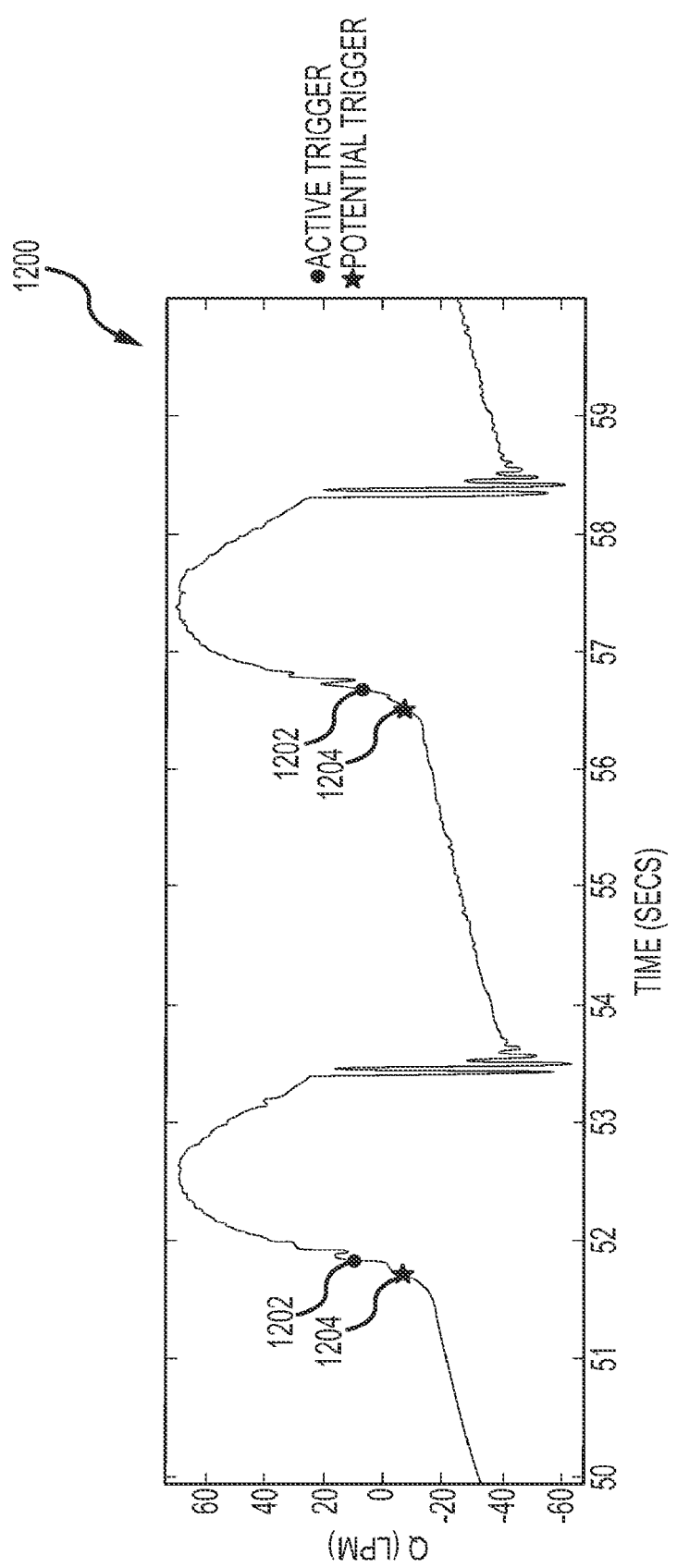
FIG. 12 illustrates an embodiment of a patient flow waveform displaying active indicators and potential indicators.
Figure 13:
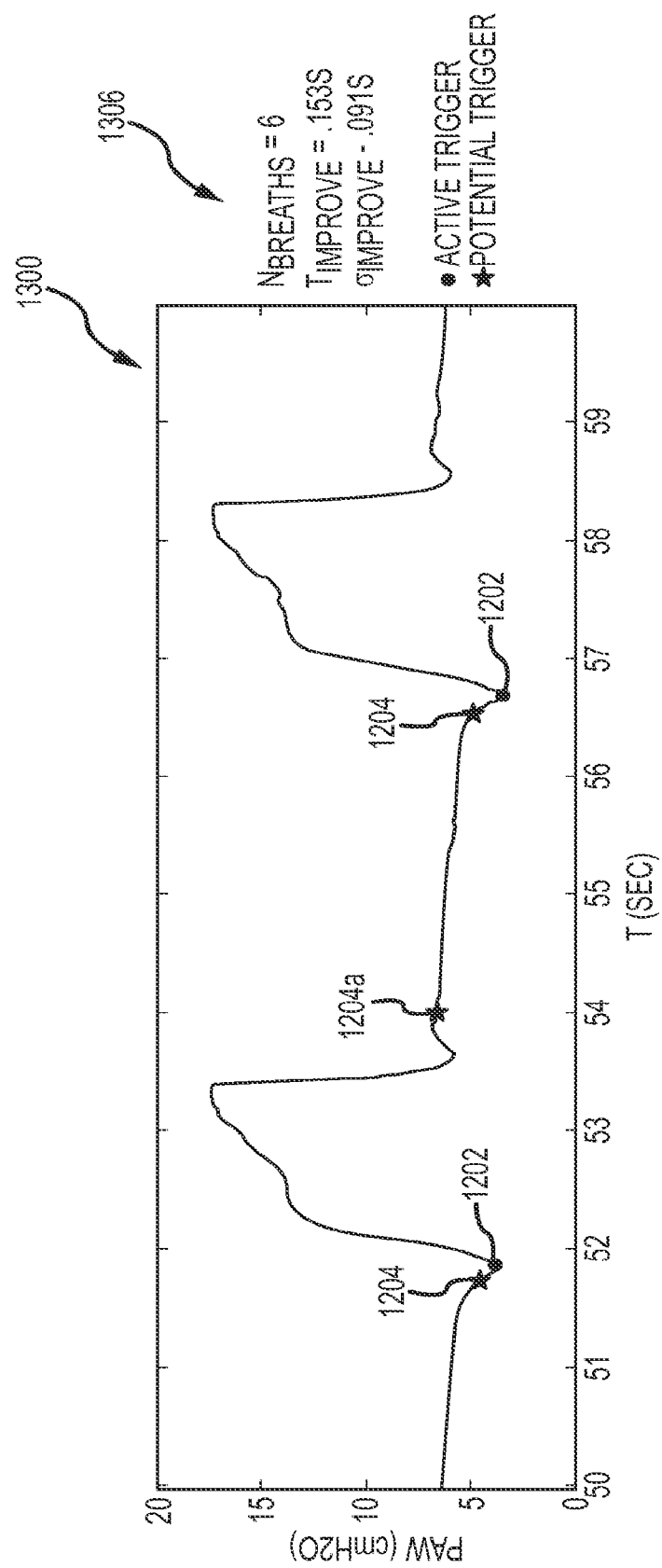
FIG. 13 illustrates an embodiment of a graph of a patient pressure waveform displaying active indicators and potential indicators.

In some embodiments, the potential trigger module 118 sends instructions to the display 122 to display a potential trigger indicator on a patient waveform where each potential patient trigger is detected. In further, embodiments, the trigger module 115 and/or the potential trigger module 118 may also send instructions to the display 122 to display an active indicator on the same patient waveform where each active patient trigger was detected that triggers the delivery of inspiration by the ventilator 100. FIGS. 12 and 13 illustrate an embodiment of a patient waveform 1200 (e.g., flow waveform) and 1300 (e.g. pressure waveform) displaying active indicators 1202 and potential indicators 1204. The display of the potential indicator 1204 in relation to the active indicators 1202 allow an operator to easily and confidently decide if the potential trigger setting increases or decreases the speed of trigger detection. Further, the display of the potential indicator 1204 in relation to the active indicators 1202 may also allow an operator to easily and confidently decide if the potential trigger threshold increases or decreases the number of false triggers for the delivered breath type. For example, as illustrate in FIG. 13, a potential trigger is illustrated with the potential indicator 1204a immediately after the start of exhalation. An operator of the ventilator would see this potential indicator 1204a and would immediately know that this detected trigger occurred too close to the beginning of exhalation and is most likely a false trigger. The presenting of this detected false trigger would inform the operator that the selected potential trigger threshold illustrated in FIG. 13 is likely too sensitive for use with this breath type and patient.

Figure 14:
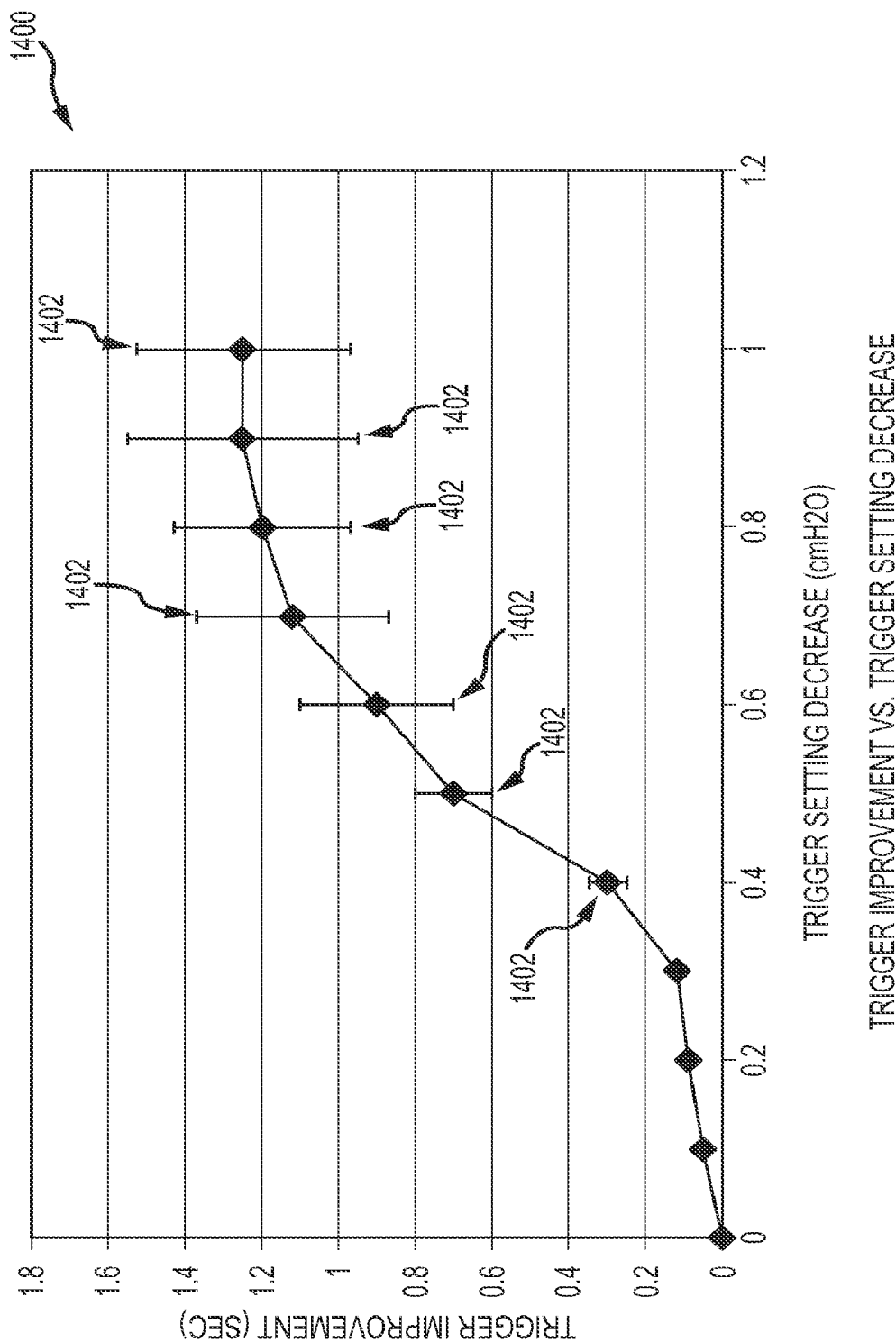
FIG. 14 illustrates an embodiment of a graph illustrating a potential decrease in triggering times for different potential trigger settings.

In additional embodiments, the potential trigger module 118 compares the detected one or more active patient triggers with the one or more determined patient efforts. Based on this comparison, the potential trigger module 118 may determine or calculate difference statistics 1306. The difference statistics 1306 is data about the difference between the detected active trigger and the potential trigger. For example, the potential trigger module 118 may send instructions to the display 122 to display the average time difference between the two different triggers along with a calculated standard deviation for the time difference and the number of delivered breaths that generated the average time difference as illustrated in FIG. 13. The potential trigger module 118 may send instructions to the display 122 to display just the difference statistics 1306 or may send instructions to the display 122 to display the difference statistics 1306 in combination with a potential indicator 1204 and active indicator 1202 on a patient waveform 1200. In further embodiments, the potential trigger module 118 may generate a difference graph based on the difference statistics and one or more different potential trigger settings. In these embodiments, the potential trigger module 118 may send instructions to the display 122 to display the difference graph. FIG. 14 illustrates an example embodiment of a difference graph 1400 illustrating the potential decrease in triggering times for different potential trigger settings. Graph 1400 further illustrates an increase in the standard deviation 1402 for the trigger improvement times as the trigger sensitivity increases, which could be the direct result of an increase in false triggers. As such, an operator may avoid implementing potential trigger thresholds that exhibit large standard deviations.

In alternative embodiments, the potential trigger module 118 receives two or more potential trigger thresholds, which is then utilized to detect multiple potential triggers. The potential trigger module 118 may analyze and display these additional potential triggers at the same time. The display of multiple potential triggers at once allows a clinician to quickly and easily pick the best potential trigger out of several choices for implementation.

In some embodiments, the display 122 on the ventilator 100 is a graphical user interface for displaying respiratory data. The ventilator 100 is configured with a computer having a user interface including the graphical user interface for accepting commands and for displaying the respiratory data. In these embodiments, the graphical user interface includes or displays graphical representations of respiratory data, one or more potential trigger indicators, and/or one or more active trigger indicators. In further embodiments, the graphical user interface further includes or displays difference statistics between the potential trigger indicator and the active breath indicator and/or graphs based on the difference statistics.

In additional embodiments, the ventilator 100 provides a graphical user interface for accepting commands and for displaying respiratory data. In these embodiments, the ventilator 100 includes at least one display device 122, a trigger module 115 that determines active patient triggers based on an active trigger setting for a given breath type, a potential trigger module 118 that determines potential patient triggers based on a potential trigger setting for the same breath type, and at least one memory 112, communicatively coupled to the at least one processor 116. The memory 112 contains instructions that, when executed by a processor of the ventilator 100, provide a graphical user interface on the at least one display 122. The graphical user interface includes or displays graphical representations of respiratory data, one or more potential trigger indicators, and one or more active breath indicators. In further embodiments, the graphical user interface further includes or displays difference statistics between the potential trigger indicator and the active breath indicator and/or graphs based on the difference statistics.

Figure 2A:
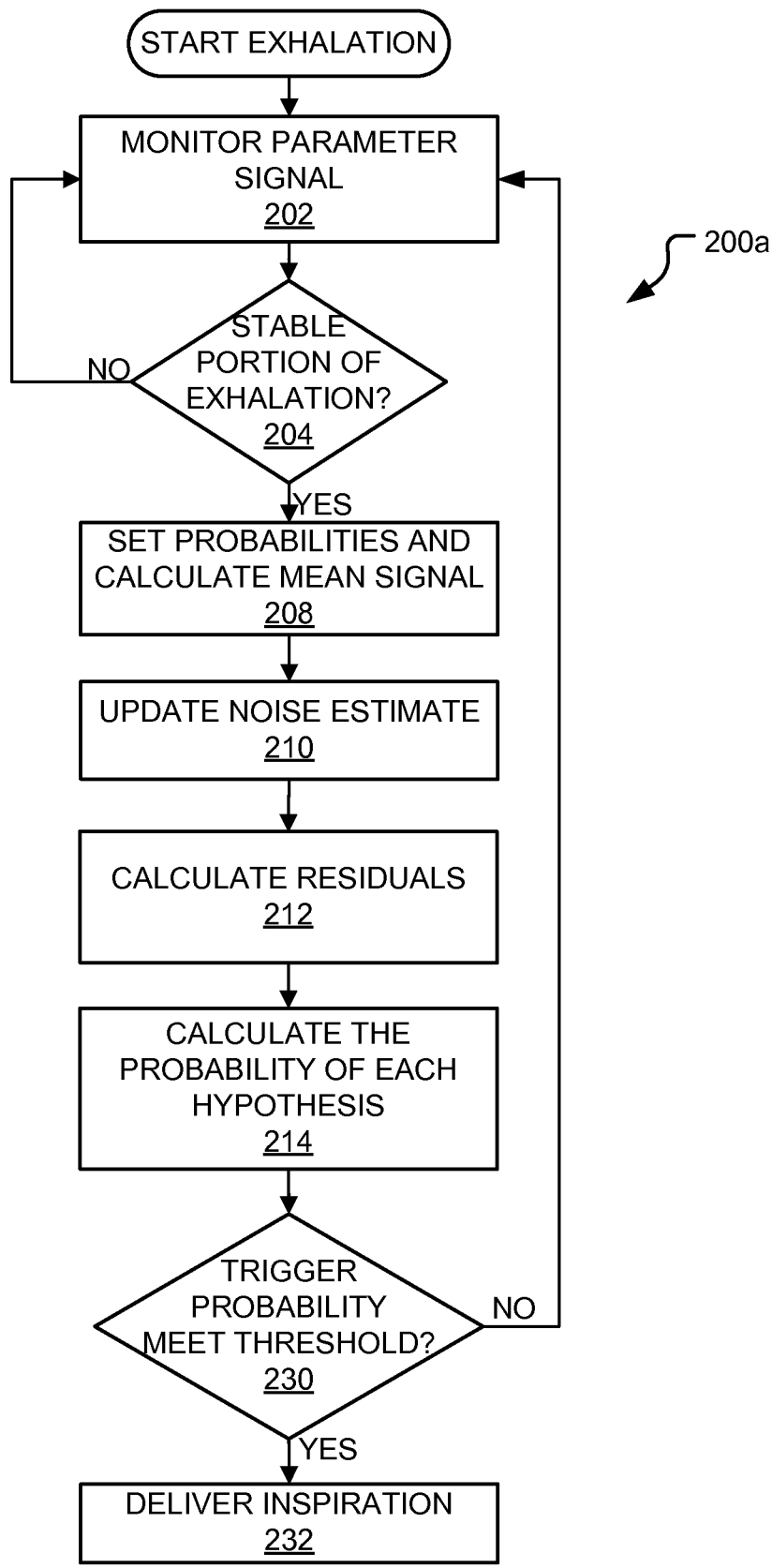
FIG. 2A illustrates an embodiment of a method for triggering inspiration during ventilation of a patient on a ventilator utilizing a constant statistical trigger mode.
Figure 2B:
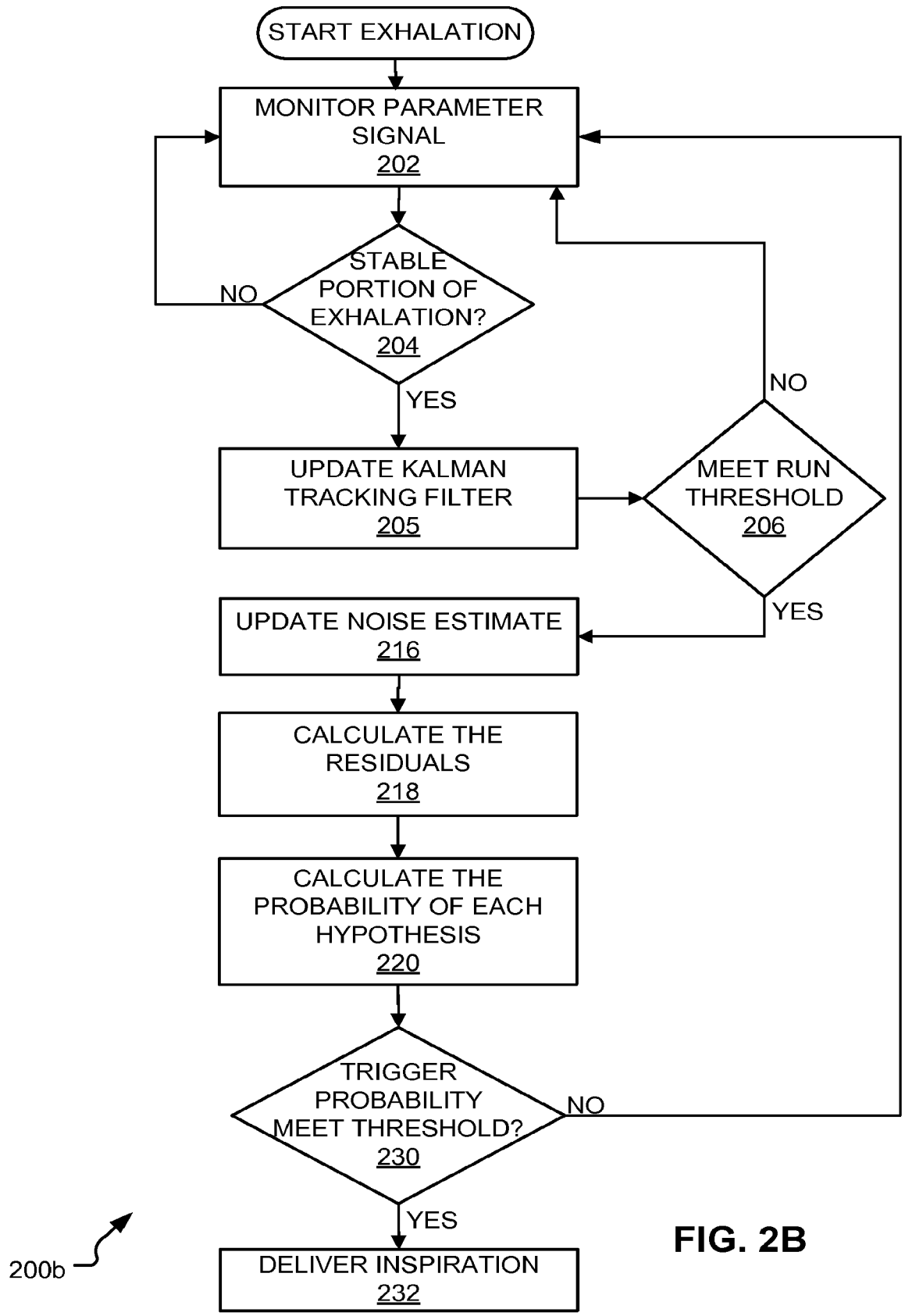
FIG. 2B illustrates an embodiment of a method for triggering inspiration during ventilation of a patient on a ventilator utilizing a variable statistical trigger mode.

FIGS. 2A and 2B illustrate embodiments of a method 200 for triggering inspiration during ventilation of a patient on a ventilator utilizing a ST mode. FIG. 2A illustrates an embodiment of a method 200a for triggering inspiration during ventilation of a patient on a ventilator utilizing a constant ST mode. FIG. 2B illustrates an embodiment of a method 200b for triggering inspiration during ventilation of a patient on a ventilator utilizing a variable ST mode.

Both methods 200a and 200b begin at the start of exhalation. As illustrated, both methods 200a and 200b include a monitoring operation 202. During the monitoring operation 202, the ventilator monitors ventilator and/or patient parameter signals. As used herein, ventilator parameters include any parameter determined by the operator and/or ventilator. As used herein, patient parameters include any parameter that is not determined by the ventilator and/or operator. In some embodiments, the ventilator during the monitoring operation 202 monitors sensor measurements and/or parameters derived or calculated from the sensor measurements. In further embodiments, the ventilator during the monitoring operation 202 monitors sensor measurements from other monitoring devices coupled to the ventilator, such as an oximeter or a capnograph. In some embodiments, the ventilator during the monitoring operation 202 monitors exhalation time, exhalation volume, exhalation flow rate, exhalation pressure, and/or intrapleural pressure. Sensors suitable for this detection may include any suitable sensing device as known by a person of skill in the art for a ventilator, such as an expiration flow sensor.

Further, both methods 200a and 200b include decision operation 204. During the decision operation 204, the ventilator determines if a stable portion of exhalation is detected. The ventilator during decision operation 204 may utilize any suitable method and/or parameter signal for determining if a stable portion of exhalation is detected. Several examples of which are discussed above. If the ventilator determines that exhalation is not stable during decision operation 204, the ventilator continues to perform operation 202 and 204 for at least the next computation cycle. If the ventilator determines that the exhalation is stable during decision operation 204, the ventilator performs setting operation 208 when utilizing the stable ST mode and, alternatively, performs Kalman updating operation 205 when utilizing the variable ST mode.

As illustrated in FIG. 2A, method 200a includes setting operation 208. The ventilator during setting operation 208 sets the initial probabilities for the null and trigger hypotheses and calculates the mean signal. In some embodiments, the ventilator during setting operation 208 assumes that the null hypothesis is true and that the trigger hypothesis is false when setting the initial probability for each of the null hypothesis and the trigger hypothesis for the parameter signal from the first computational cycle of the exhalation. For example, the ventilator during setting operation 208 may utilize equations #1, #2, and #3 to calculate the initial probabilities. In additional embodiments, the ventilator during setting operation 208 calculates the mean parameter signal based on a predetermined set of parameter signals for a most recent set of computational cycles since the parameter signal of the null hypothesis is assumed to be constant from one computational cycle to another. For example, the trigger module 115 may utilize equation #4 to calculate the mean parameter signal. In further embodiments, the ventilator during setting operation 208 sets the initial probability for each of the null hypothesis and the trigger hypothesis by adding a hypothesis transition probability to a probability of a previous state for each of the null hypothesis and the trigger hypothesis. For example, the ventilator during setting operation 208 may utilize equation #5 to calculate or set the initial probability for each of the null hypothesis and the trigger hypothesis for the parameter signal for the current computational cycle. In some embodiments, the ventilator during setting operation 208 calculates the hypothesis transition probability based on a respiration rate and a sampling frequency. For example, the ventilator during setting operation 208 may utilize equation #6 to calculate the hypothesis transition probability. In alternative embodiments, the probability of transition increases as exhalation time (t) approaches t=60/RR, allowing the ventilator during setting operation 208 to react more aggressively as exhalation time approaches the average time between breaths.

As illustrated in FIG. 2A, method 200a also includes an updating operation 210. Updating operation 210 is performed by the ventilator after the mean signal is calculated during setting operation 208. The ventilator during updating operation 210 calculates or updates the noise estimate based at least on the calculated mean parameter signal. In some embodiments, this is accomplished by the ventilator during updating operation 210 by calculating the standard deviation for all the parameter signals for each measured computational cycle taken so far during the exhalation. For example, the ventilator during updating operation 210 may utilize equation #7 to calculate the noise estimate.

As illustrated in FIG. 2A, method 200a also includes a calculating residuals operation 212. The calculating residuals operation 212 is performed by the ventilator after the initial probabilities for the null and trigger hypotheses are set during setting operation 208. The ventilator during calculating residuals operation 212 calculates a residual for the null hypothesis and the trigger hypothesis based at least on the parameter signal for the current computational cycle. For example, the ventilator during calculating residuals operation 212 may utilize generalized equation #8 to calculate the residuals for each hypothesis. In some embodiments, the ventilator during calculating residuals operation 212 calculates the residual for the null hypothesis by subtracting the mean value for the null hypothesis from the parameter signal for the current computational cycle. For example, the ventilator during calculating residuals operation 212 may utilize equation #9 to calculate the residual for the null hypothesis. In further embodiments, the ventilator during calculating residuals operation 212 calculates the residual for the trigger hypothesis by subtracting a predicted mean value for the trigger hypothesis from the parameter signal for the current computational cycle. For example, the ventilator during calculating residuals operation 212 may utilize equation #10 to calculate the residual for the trigger hypothesis.

Additionally, method 200a also includes a calculating probabilities operation 214. The calculating probabilities operation 214 is performed by the ventilator after operations 208, 210, and 212 are performed by the ventilator. The ventilator during calculating probabilities operation 214 calculates a first probability for the null hypothesis for the parameter signal for the current computational cycle based on the initial probability for the null hypothesis, the noise estimate, and the residual for the null hypothesis. The ventilator during calculating probabilities operation 214 also calculates a second probability for the trigger hypothesis for the parameter signal for the current computational cycle based on the initial probability for the trigger hypothesis, the noise estimate, and the residual for the trigger hypothesis. In some embodiments, the ventilator during calculating probabilities operation 214 calculates the first and second probabilities by calculating a probability density function for each of the null hypothesis and the trigger hypothesis and by multiplying the probability density function for each hypothesis with its corresponding initial probability and normalizing. For example, the ventilator during calculating probabilities operation 214 may utilize the equation #11 to calculate the probability density function for each of the hypotheses. The ventilator during calculating probabilities operation 214 may utilize the equation #12 to calculate the first and second probabilities (e.g., multiplying the probability density function with its corresponding initial probability and normalizing.

As illustrated in FIG. 2B, method 200b includes Kalman updating operation 205. The ventilator during Kalman updating operation 205 calculates an initial predicted parameter signal for the next computational cycle at an initial covariance for the parameter signal (or true state of the measurement (x)) for the current computational cycle. In further embodiments, the ventilator during Kalman updating operation 205 calculates the post predicted parameter signal for the next computational cycle at a post covariance for a first derivative (velocity state ($\dot{x}$)) and a second derivative (acceleration state ($\ddot{x}$)) of the parameter signal for the current computational cycle. In other words, the ventilator during Kalman updating operation 205 analyzes the actual signal parameter (x), the first derivative of the signal parameter (ẋ), and second derivative of the signal parameter (ẍ) for a current computational cycle to predict the initial and post signal parameters for the next computational cycle for the null hypothesis and the trigger hypothesis.

Within a breath, the ventilator assumes that the true velocity and acceleration states are not time-varying. As such, the ventilator during Kalman updating operation 205 estimates the true value of them. For example, the ventilator during Kalman updating operation 205 may utilize the state transition matrix of equation #14. In some embodiments, at t=0, both the initial covariance estimate (M) and post covariance estimate (P) are constructed by the ventilator during Kalman updating operation 205 using measurement noise (v) to define the diagonals, ignoring the coupled covariance values, an example of which is illustrated in equation #15. In order to prevent the filter from collapsing, a small amount of process noise is injected at each time step by the ventilator during Kalman updating operation 205. For example, the structure of this process noise may be defined as shown in equation #16.

In some embodiments, the ventilator during Kalman updating operation 205 utilizes the Kalman Tracking Filter equations to calculate the initial predicted parameter signal at the initial covariance and the post predicted signal at the post covariance for the next computational cycle. For example, the ventilator during Kalman updating operation 205 may utilize Kalman Tracking Filter equations #17 #18, #19, #20, #21, #22, and #23 to calculate the initial predicted parameter signal at the initial covariance and the post predicted signal at the post covariance for the next computational cycle. The ventilator during method 200b utilizes the initial and post predicted signals instead of the initial probabilities as used by the ventilator during method 200a.

Additionally, as illustrated in FIG. 2B, method 200b includes a run decision operation 206. The run decision operation 206 is performed by the ventilator after the performance of Kalman updating operation 205. The ventilator during run decision operation 206 determines if it is ready to calculate the first and second probabilities for the null and trigger hypotheses based on a predetermined run threshold. The predetermined run threshold may be selected based on user input or selected by the ventilator based on ventilator and patient parameters. In some embodiments, the run threshold is a minimum exhalation time. For example, the minimum exhalation time may be an exhalation time of at least 50 ms. In alternative embodiments, the predetermined run threshold is a maximum covariance value for the initial predicted signal parameter and/or the post predicted signal parameter. For example, the maximum covariance value may be at most the square of the measurement sensor noise. In alternative embodiments, the predetermined run threshold is a minimum confidence rate calculated based on the covariance value for the initial predicted signal parameter and/or the post predicted signal parameter. For example, the minimum confidence rate may be confidence rate of at least 90%. If the ventilator during run decision operation 206 determines that the run threshold has been met, the ventilator performs updating noise operation 216. If the ventilator during run decision operation 206 determines the run threshold has not been met, the ventilator performs monitoring operation 202 and decision operation 204 for at least the next computational cycle.

Further, as illustrated in FIG. 2B, method 200b includes an updating noise operation 216. The ventilator during updating noise operation 216 calculates or updates the noise estimate based at least on a single value of the covariance utilized in calculating at least one of the initial covariance and the post covariance. In some embodiments, this is accomplished by the ventilator during updating noise operation 216 by calculating the square root of P(1,1) in equation #15 listed above. In some embodiments, this is accomplished by the ventilator during updating noise operation 216 by calculating the square root of the measurement noise (v).

As illustrated in FIG. 2B, method 200b also includes a calculating residuals operation 218. Operation 218 is performed by the ventilator after the ventilator determines that the run threshold has been met during run decision operation 206. The ventilator during operation 218 calculates a residual for the null hypothesis and the trigger hypothesis based at least on the parameter signal for the current computational cycle. In some embodiments, the ventilator during operation 218 calculates the residual for the null hypothesis by differencing the parameter signal for the current computational cycle with the initial predicted value. For example, the ventilator during operation 218 may utilize equation #24 to calculate the residual for the null hypothesis. In further embodiments, the ventilator during operation 218 calculates the residual for the trigger hypothesis by subtracting an initial predicted parameter signal for the trigger hypothesis from the parameter signal for the current computational cycle. For example, the ventilator during operation 218 may utilize equation #25 to calculate the residual for the trigger hypothesis.

Additionally, method 200b also includes a calculating probabilities operation 220. Operation 220 is performed by the ventilator after operations 205, 216, and 218 are performed by the ventilator. The ventilator during operation 220 calculates a first probability for the null hypothesis for the parameter signal for the current computational cycle based on the initial predicted parameter signal for the null hypothesis, the noise estimate, and the residual for the null hypothesis. The ventilator during operation 220 also calculates a second probability for the trigger hypothesis for the parameter signal for the current computational cycle based on the initial predicted parameter signal for the trigger hypothesis, the noise estimate, and the residual for the trigger hypothesis. In some embodiments, the ventilator during operation 220 calculates the first and second probabilities by calculating a probability density function for each of the null hypothesis and the trigger hypothesis and by multiplying the probability density function for each hypothesis with its corresponding predicted signal parameter and normalizing. For example, the ventilator during operation 220 may utilize equation #11 to calculate the probability density function for each of the hypotheses. In another example, the ventilator during operation 220 may utilize equation #12 (e.g., multiplying the probability density function with its corresponding predicted signal parameter and normalizing) to calculate the first and second probabilities.

Both methods 200a and 200b include a trigger decision operation 230. The ventilator during method 200a performs trigger decision operation 230 after the performance of operation 214. The ventilator during method 200b performs trigger decision operation 230 after the performance of operation 220. The ventilator during trigger decision operation 230 compares each probability to a trigger threshold. Based on this comparison, the ventilator during trigger decision operation 230 determines if the probability of the trigger hypothesis meets the trigger threshold. If the ventilator during trigger decision operation 230 determines that trigger hypothesis does not meet the trigger threshold, the ventilator performs operations 202 and 204 again at least for the next computation cycle. If the ventilator during trigger decision operation 230 determines that the trigger hypothesis meets the trigger threshold, the ventilator performs delivering operation 232. The trigger threshold, as discussed above, may be selected by a user or selected by the ventilator based on ventilator and patient parameters. In some embodiments, the trigger threshold is a minimum probability. For example, the minimum probability may be at least 98%. In another example, the minimum probability may be at least 99%.

Both methods 200a and 200b include a delivering operation 232. The ventilator during delivering operation 232 delivers an inspiration, which effectively ends the exhalation phase. In other words, operation 232 controls the ventilation (inspiration versus exhalation) delivered to the patient by the ventilator based on the result of the trigger decision operation 230. The inspiration provided to the patient may be determined by the ventilator and/or patient parameters. For example, the delivered inspiration may be based on a selected breath type or ventilation mode, such as volume control, pressure control, proportional assist, and etc.

In other embodiments, method 200 includes a display operation. The ventilator during the display operation displays any suitable information for display on a ventilator. In one embodiment, the display operation displays parameter signals, initial probabilities, mean parameter signals, noise estimates, residuals, calculated probabilities, trigger thresholds, run thresholds, predicted signal parameters, and etc.

In some embodiments, a microprocessor-based ventilator that accesses a computer-readable medium having computer-executable instructions for performing the method of ventilating a patient with a medical ventilator is disclosed. This method includes performing or repeatedly performing the steps disclosed in method 200a or 200b above and/or as illustrated in FIGS. 2A and 2B.

In some embodiments, the ventilator system includes: means for monitoring a parameter signal during an exhalation; means for determining a stable portion of exhalation based at least on the parameter signal for a current computational cycle; means for setting an initial probability for each of a null hypothesis and a trigger hypothesis based on a current exhalation time; means for calculating a mean of the parameter signal based on a predetermined set of parameter signals for a most recent set of computational cycles; means for updating a noise estimate based at least on the mean parameter signal; means for calculating a residual for the null hypothesis and the trigger hypothesis based at least on the parameter signal for the current computational cycle; means for calculating a first probability for the null hypothesis and calculating a second probability for the trigger hypothesis for the parameter signal for the current computational cycle based on the initial probability, the noise estimate, and the residual; means for comparing the first probability and the second probability to a threshold; and means for delivering inspiration when the second probability meets the threshold.

In some embodiments, the ventilator system includes: means for monitoring a parameter signal during an exhalation; means for determining a stable portion of exhalation based at least on the parameter signal for a current computational cycle; means for calculating an initial predicted parameter signal of the next computational cycle and an initial covariance for the initial predicted parameter signal for the parameter signal for the current computational cycle; means for calculating a post predicted parameter signal of the next computational cycle and a post covariance for the post predicted parameter signal for a first and second derivative of the parameter signal of the parameter signal for the current computational cycle; means for determining that a run threshold has been met based on at least one of a current exhalation time, the initial covariance, and the post covariance; means for updating a noise estimate based at least on a single covariance value utilized in calculating at least one of the initial covariance and the post covariance; means for calculating a residual for each of the null hypothesis and the trigger hypothesis based at least on the parameter signal for the current computational cycle; means for calculating a first probability for the null hypothesis and calculating a second probability for the trigger hypothesis for the parameter signal for the current computational cycle based at least on a predicted parameter signal, the noise estimate, and the residual; means for comparing the first probability and the second probability to a trigger threshold; and means for delivering inspiration when the second probability meets the threshold.

Figure 3:
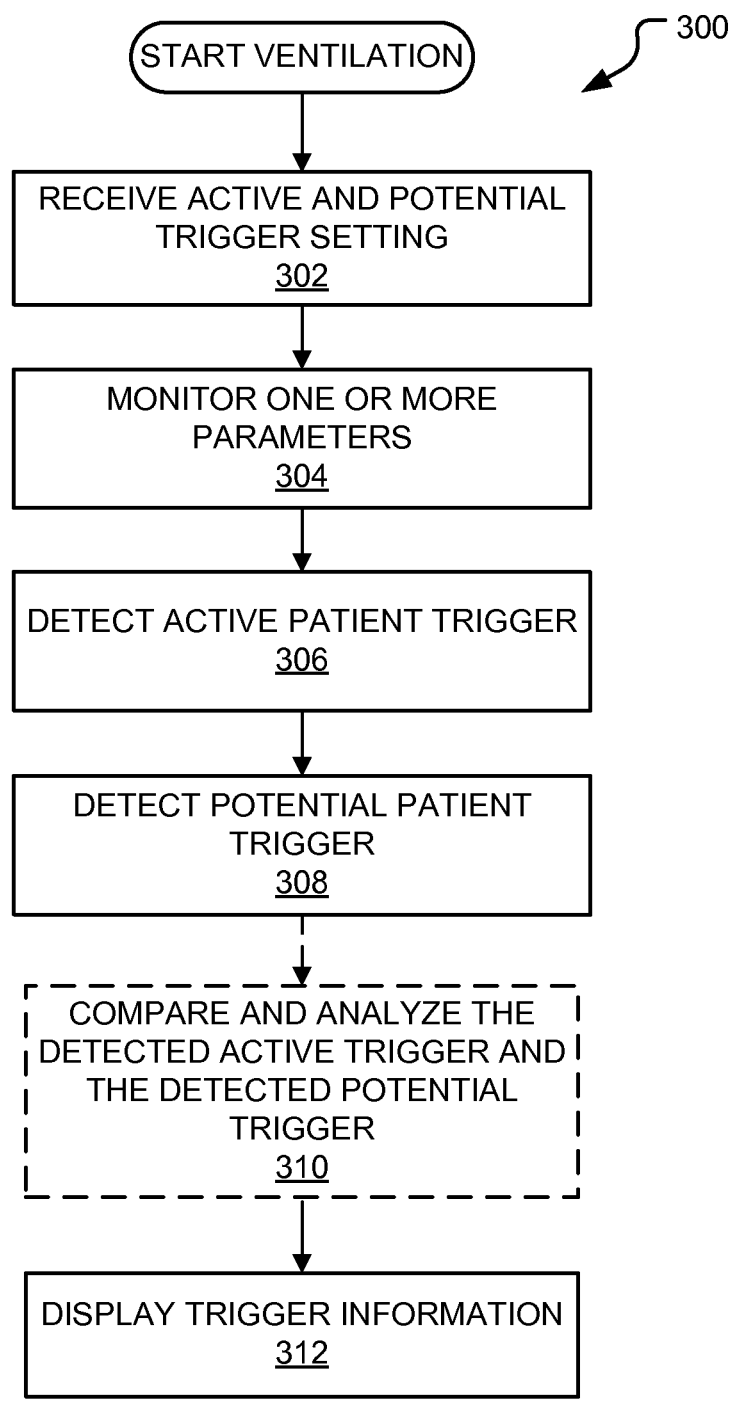
FIG. 3 illustrates an embodiment of a method for analyzing and/or displaying potential trigger information for a delivered breath type during ventilation of a patient on a ventilator.

FIG. 3 illustrates an embodiment of a method 300 for analyzing potential trigger sensitivities and/or displaying potential trigger information during ventilation of a patient on a ventilator. Providing the operator with information about a potential trigger for a delivered breath type allows the operator to quickly and easily determine if a change to the trigger sensitivity would be beneficial to the patient. In some embodiments, the ventilator during method 300 is activated by user input or selection. For example, the operator of the ventilator may turn on or activate a potential trigger application, which in turn activates or turns on method 300.

Method 300 begins at the start of exhalation. As illustrated in FIG. 3 method 300 includes a receiving operation 302. The ventilator during receiving operation 302 receives one or more potential trigger settings. The one or more potential trigger settings are received from user input or selection. In some embodiments, ventilator during receiving operation 302 receives a potential trigger setting from user input only after a potential trigger application has been activated by the operator.

Further, method 300 includes a monitoring operation 304 as illustrated in FIG. 3. The ventilator during monitoring operation 304 monitors respiratory data (including one or more parameter signals). In some embodiments the ventilator during monitoring operation 304 monitors respiratory data with one or more sensors. The respiratory data may be any monitored parameter signal or parameters derived therefrom. The ventilator during monitoring operation 304 monitors the same respiratory data for the active trigger setting and the passive trigger setting. In further embodiments, the monitoring operation 304 stores the monitored respiratory data to form past respiratory data. The past respiratory data is any stored respiratory data from one or more previous or past computation cycles.

Additionally, method 300 includes an active detecting operation 306 as illustrated in FIG. 3. The ventilator during active detecting operation 306 detects active patient triggers based on the active trigger setting and the monitored respiratory data. In some embodiments, the ventilator during active detecting operation 306 delivers inspiration in response to a detected active patient trigger. In further embodiments, the ventilator during active detecting operation 306 stores the detected active patient triggers to form past active patient trigger. The past active patient triggers are any stored active patient triggers from one or more previous or past computation cycles.

As illustrated in FIG. 3, method 300 includes a potential detecting operation 308. The ventilator during the potential detecting operation 308 detects potential patient triggers based on each received potential trigger setting and the monitored respiratory data. In some embodiments, the ventilator during the potential detecting operation 308 detects a potential patient trigger when the respiratory data breaches the one or more potential trigger setting. However, the ventilator during the potential detecting operation 308 does not deliver or trigger inspiration based on any detected potential patient trigger. In some embodiments, the ventilator during potential detecting operation 308 retrieves the stored respiratory data and determines one or more past potential patient triggers based on the stored respiratory data. In further embodiments, the ventilator during potential detecting operation 308 retrieves the stored respiratory data in response to the activation of the potential trigger application and/or the receipt of a potential trigger. The past potential patient triggers are any determined past potential patient triggers from one or more previous or past computation cycles.

In some embodiments, method 300 includes an analyzing operation 310. The ventilator during the analyzing operation 310 compares one or more active patient triggers to the corresponding one or more potential patient trigger. Based on this comparison, the ventilator during the analyzing operation 310 determines difference statistics. The difference statistics, as discussed above, is data about the difference between the detected active patient trigger and the one or more potential patient triggers. In some embodiments, the difference statistics may include the time difference between the detected active patient trigger and the potential patient trigger, the average time difference between the two different triggers, a calculated standard deviation for the average time difference, and the number of delivered breaths that generated the average time difference. This list is exemplary and is not meant to be limiting. Any useful difference statistics may be determined by the ventilator during operation 310 as would be known by a person of skill in the art. In further embodiments, the ventilator during the analyzing operation 310 may determine or generate a graph of the difference statistics for one or multiple potential trigger settings.

In further embodiments, the ventilator during the analyzing operation 310 compares one or more past active patient triggers to the corresponding one or more past potential patient trigger. In these embodiments, based on this comparison, the ventilator during the analyzing operation 310 also determines difference statistics for the one or more past active patient triggers and the corresponding past potential patient triggers. In additional embodiments, the ventilator during the analyzing operation 310 may determine or generate a graph of the difference statistics for one or multiple past potential trigger settings and/or past active patient triggers. In other words, the ventilator during analyzing operation 310 post-processes stored respiration data to determine past potential triggers when the potential trigger module is activated and/or when a potential trigger is received.

As illustrated in FIG. 3, method 300 includes a displaying operation 312. The ventilator during the displaying operation 312 displays information based on one or more of the detected active patient triggers and on one or more of the detected potential patient trigger. In some embodiments, the ventilator during the displaying operation 312 displays one or more active indicators on a patient waveform where each active patient trigger is detected. In additional embodiments, the ventilator during the displaying operation 312 displays a potential indicator on the patient waveform where each potential patient trigger is detected for the one or more potential trigger settings. For example, FIGS. 12 and 13 illustrate an embodiment of a patient waveform 1200 (e.g., flow waveform) and 1300 (e.g. pressure waveform) displaying active indicators and potential indicators. In further embodiments, the ventilator during the displaying operation 312 displays difference statistics. For example, some exemplary difference statistics 1306 are displayed in FIG. 13. In some embodiments, the ventilator during the displaying operation 312 displays a graph of the difference statistics for one or multiple potential trigger settings for one or multiple potential trigger settings. For example, FIG. 14 illustrates an example embodiment of a difference graph 1400 showing the potential decrease in triggering times for different potential trigger settings. In further embodiments, the displaying information includes displaying information about one or more past active patient triggers and one or more past potential patient trigger.

In other embodiments, a microprocessor-based ventilator that accesses a computer-readable medium having computer-executable instructions for performing the method of ventilating a patient with a ventilator is disclosed. This method includes performing or repeatedly performing the steps disclosed in method 300 above and/or as illustrated in FIG. 3.

In some embodiments, the ventilator system includes: means for receiving an active trigger setting for a set breath type; means for receiving a potential trigger setting for the set breath type; means for monitoring respiratory data with at least one sensor; means for detecting active patient triggers based on the active trigger setting and the respiratory data; means for detecting at least one potential patient trigger based on the potential trigger setting and the respiratory data; and means for displaying information based on at least one active patient trigger and the at least one potential patient trigger.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present technology as described. Numerous other changes may be made which will readily suggest themselves to those skilled in the art and which are encompassed in the spirit of the disclosure and as defined in the claims.

What is claimed is:

1. A method implemented by a ventilator for analyzing potential trigger sensitivities, the method comprising:
   receiving an active trigger setting for a set breath type;
   receiving a potential trigger setting for the set breath type;
   monitoring respiratory data with at least one sensor;
   detecting an active patient trigger based on the active trigger setting and the respiratory data;
   detecting a potential patient trigger based on the potential trigger setting and the respiratory data;
   in response to detecting the active patient trigger, delivering breathing to a patient;
   determining difference statistics based on a comparison of the active patient trigger to the potential patient trigger; and
   displaying the difference statistics about the active patient trigger and the potential patient trigger, wherein the difference statistics include an average time difference based on at least the active patient trigger and the potential patient trigger.

2. The method of claim 1, further comprising:
   displaying an active indicator on a patient waveform where the active patient trigger is detected; and
   displaying a potential indicator on the patient waveform where the potential patient trigger is detected.

3. The method of claim 1, wherein the set breath type utilizes a flow trigger, wherein the active trigger setting is a first flow trigger threshold and the potential trigger setting is a second flow trigger threshold.

4. The method of claim 1, further comprising:
   storing past respiratory data monitored with the at least one sensor for at least one previous computation cycle;
   storing a past active patient trigger detected for the at least one previous computation cycle;
   wherein the potential trigger setting is received with activation of a potential trigger application by an operator;
   retrieving the stored past respiratory data upon activation of the potential trigger application;
   determining a past potential patient trigger based on the stored past respiratory data; and
   displaying data about the past active patient trigger and the past potential patient trigger.

5. The method of claim 1, further comprising:
   displaying a number of detected false triggers for the potential trigger setting.

6. The method of claim 1, further comprising:
   displaying a number of detected false triggers for the active trigger setting and the potential trigger setting.

7. The method of claim 1, further comprising:
   after the displaying of the difference statistics, receiving a selection to implement the potential trigger setting as an active trigger setting for subsequently delivered breathing.

8. The method of claim 1, further comprises:
   in response to the displaying of the difference statistics, automatically implementing the potential trigger setting as an active trigger setting for subsequently delivered breathing.

9. The method of claim 1, further comprises:
   comparing the active patient trigger to the potential patient trigger;
   determining that the potential trigger setting reduced trigger time and decreased a number of false triggers based on the comparison; and
   in response to the determination, automatically implementing the potential trigger setting as an active trigger setting for subsequently delivered breathing.

10. The method of claim 1, wherein the set breath type utilizes a pressure trigger, wherein the active trigger setting is a first pressure trigger threshold and the potential trigger setting is a second pressure trigger threshold.

11. The method of claim 1, further comprising:
    wherein the difference statistics include a time difference between the active trigger and the potential patient trigger.

12. A method implemented by a ventilator for analyzing potential trigger sensitivities, the method comprising:
    receiving an active trigger setting for a set breath type;
    receiving a selection for activating a potential trigger application;
    in response to the selection, automatically selecting one or more potential trigger settings for the set breath type;
    monitoring respiratory data with at least one sensor;
    detecting an active patient trigger based on the active trigger setting and the respiratory data;
    detecting one or more potential patient triggers based on the one or more potential trigger settings and the respiratory data;
    delivering a breath to the patient in response to the detection of the active patient trigger;
    displaying information about the active patient trigger and the one or more potential patient triggers;
    comparing the active patient trigger to the one or more potential patient triggers;
    determining that one of the one or more potential trigger setting reduced trigger time and decreased a number of false triggers based on the comparison; and
    in response to the determination, automatically implementing the determined potential trigger setting as an active trigger setting for a subsequently delivered breath.

13. The method of claim 12, wherein the displaying information comprises:
    displaying an active indicator on a patient waveform where the active patient trigger is detected; and
    displaying a potential indicator on the patient waveform where each of the one or more potential patient triggers is detected.

14. The method of claim 12, wherein the one or more potential trigger settings includes at least two different potential trigger settings.

15. The method of claim 14, wherein the displaying information comprises:
    displaying an active indicator on a patient waveform in response to detecting the active patient trigger; and
    displaying potential indicators on the patient waveform in response to detecting each of the one or more potential patient triggers for the two different potential patient trigger settings.

16. The method of claim 14, further comprising:
    determining difference statistics based on the comparison of the active patient trigger to the one or more potential patient triggers, wherein the displaying information includes displaying the difference statistics for each potential patient trigger setting.

17. The method of claim 14, wherein the set breath type utilizes a flow trigger, wherein the active trigger setting is a first flow trigger threshold, wherein the at least two different potential trigger settings are a second flow trigger threshold and a third flow trigger threshold, and wherein the first flow trigger threshold, the second flow trigger threshold, and the third flow trigger threshold are different.

18. A ventilator system comprising:

a processor electronically coupled to a memory storing computer-readable instructions that, when executed, cause the processor to:

receive an active trigger setting for a set breath type;

receive a potential trigger setting for the set breath type;

monitor respiratory data with at least one sensor;

detect active patient triggers based on the active trigger setting and respiratory data;

deliver breaths to a patient in response to detection of the active patient triggers;

detect potential patient triggers based on the potential trigger setting and the respiratory data;

compare the active patient triggers to the potential patient triggers;

determine difference statistics based on the comparison of the active patient triggers to the potential patient triggers; and display the difference statistics based on the comparison, wherein the difference statistics include an average time difference between the active patient triggers and the potential patient triggers.

* * * * *